US009738718B2

(12) United States Patent
Liu et al.

(10) Patent No.: US 9,738,718 B2
(45) Date of Patent: Aug. 22, 2017

(54) ICOS BINDING PROTEINS

(71) Applicant: GlaxoSmithKline Intellectual Property Development Limited, Middlesex (GB)

(72) Inventors: Yao-Bin Liu, Collegeville, PA (US); Patrick Mayes, Collegeville, PA (US); Radha Shah Parmar, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/387,161

(22) Filed: Dec. 21, 2016

(65) Prior Publication Data
US 2017/0174767 A1 Jun. 22, 2017

Related U.S. Application Data

(60) Continuation of application No. 15/246,662, filed on Aug. 25, 2016, which is a division of application No. 15/006,560, filed on Jan. 26, 2016.

(60) Provisional application No. 62/247,355, filed on Oct. 28, 2015, provisional application No. 62/192,331, filed on Jul. 14, 2015, provisional application No. 62/108,605, filed on Jan. 28, 2015.

(51) Int. Cl.
C07K 16/28 (2006.01)
A61K 39/395 (2006.01)
A61K 39/00 (2006.01)

(52) U.S. Cl.
CPC ...... *C07K 16/2818* (2013.01); *C07K 16/2803* (2013.01); *A61K 2039/507* (2013.01); *C07K 2317/21* (2013.01); *C07K 2317/24* (2013.01); *C07K 2317/33* (2013.01); *C07K 2317/56* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 6,113,918 | A | 9/2000 | Johnson et al. |
| 6,525,028 | B1 | 2/2003 | Johnson et al. |
| 6,803,039 | B2 | 10/2004 | Tsuji et al. |
| 6,911,434 | B2 | 6/2005 | Baldridge et al. |
| 6,984,720 | B1 | 1/2006 | Korman et al. |
| 7,030,225 | B1 | 4/2006 | Tamatani et al. |
| 7,129,219 | B2 | 10/2006 | Johnson et al. |
| 7,259,247 | B1 | 8/2007 | Kroczek |
| 7,368,531 | B2 | 5/2008 | Rosen et al. |
| 7,465,444 | B2 | 12/2008 | Watanabe |
| 7,465,445 | B2 | 12/2008 | Tezuka et al. |
| 7,504,101 | B2 | 3/2009 | Weinberg |
| 7,550,140 | B2 | 6/2009 | Bakker et al. |
| 7,605,238 | B2 | 10/2009 | Korman et al. |
| 7,708,993 | B2 | 5/2010 | Yoshinaga et al. |
| 7,754,208 | B2 | 7/2010 | Ledbetter et al. |
| 7,758,852 | B2 | 7/2010 | Soto-Jara et al. |
| 7,928,074 | B2 | 4/2011 | Khare |
| 7,943,743 | B2 | 5/2011 | Korman et al. |
| 7,960,515 | B2 | 6/2011 | Min et al. |
| 8,008,449 | B2 | 8/2011 | Korman et al. |
| 8,168,179 | B2 | 5/2012 | Honjo et al. |
| 8,168,757 | B2 | 5/2012 | Finnefrock et al. |
| 8,536,672 | B2 | 9/2013 | Chang et al. |
| 8,586,386 | B2 | 11/2013 | Hunig et al. |
| 8,779,108 | B2 | 7/2014 | Queva et al. |
| 8,840,889 | B2 | 9/2014 | Chen |
| 9,163,085 | B2 | 10/2015 | Liu et al. |
| 9,193,789 | B2 | 11/2015 | Coyle et al. |
| 2002/0164697 | A1 | 11/2002 | Coyle et al. |
| 2004/0001831 | A1 | 1/2004 | Rottman et al. |
| 2004/0029226 | A1 | 2/2004 | Alsobrook et al. |
| 2005/0202442 | A1 | 9/2005 | Morris et al. |

(Continued)

FOREIGN PATENT DOCUMENTS

| EP | 1 125 585 A1 | 8/2001 |
| EP | 1 374 901 A1 | 1/2004 |

(Continued)

OTHER PUBLICATIONS

Aalberse, et al., *Immunology*, 105(1):9-19 (2002).
Ara, et al., "Potent activity of soluble B7RP-1-Fc in therapy of murine tumors in syngeneic hosts", *Int. J. Cancer*, 103(4): 501-7 (2003).
Baldan, et al., *Br. J. Cancer*,112:1510-1518 (2015).
Barouch, et al., "Immunologic strategies for HIV-1 remission and eradication", *Science*, 345(6193): 169-174 (2014).
Bartholomaeus, et al., "Cell contact-dependent priming and Fc interaction with CD32+ immune cells contribute to the TGN1412-triggered cytokine response", *J. Immunol.*, 192(5): 2091-8 (2014).
Bartholomew, et al., *Immunology*, 85(1):41-48 (1995).
Bentebibel, et al., *Sci. Transl. Med.*, 5(176):176ra32 (2013).
Bogunovic, et al., "Immune profile and mitotic index of metastatic melanoma lesions enhance clinical staging in predicting patient survival", *Proc. Natl. Acad. Sci.*, 106(48): 20429-34 (2009).
Boomer, et al., "Immunosuppression in patients who die of sepsis and multiple organ failure", *JAMA*, 306(23): 2594-2605 (2011).

(Continued)

Primary Examiner — Ilia Ouspenski
(74) Attorney, Agent, or Firm — Leah M. Octavio; Andrea V. Lockenour

(57) ABSTRACT

The present invention relates to an ICOS binding protein or antigen binding portion thereof that is an agonist to human ICOS and does not induce complement, ADCC, or CDC when placed in contact with a T cell in vivo and methods of treating cancer, infectious disease and/or sepsis with said ICOS binding protein or antigen binding portion thereof. Further the ICOS binding proteins or antigen binding portions thereof of the present invention are capable of activating a T cell when placed in contact with said T cell; stimulating T cell proliferation when placed in contact with said T cell and/or inducing cytokine production when placed in contact with said T cell. The present invention relates to ICOS binding proteins or antigen binding portions thereof comprising one or more of: SEQ ID NO:1; SEQ ID NO:2; SEQ ID NO:3; SEQ ID NO:4; SEQ ID NO:5; and/or SEQ ID NO:6.

20 Claims, 25 Drawing Sheets

(56) References Cited

U.S. PATENT DOCUMENTS

| | | |
|---|---|---|
| 2007/0048301 A1 | 3/2007 | Bodary-Winter et al. |
| 2007/0099251 A1 | 5/2007 | Zhang et al. |
| 2007/0184444 A1 | 8/2007 | Abbas et al. |
| 2007/0185017 A1 | 8/2007 | Aggarwal et al. |
| 2010/0303811 A1 | 12/2010 | Ochi |
| 2011/0243929 A1 | 10/2011 | Coyle et al. |
| 2011/0293605 A1 | 12/2011 | Sathish et al. |
| 2012/0121633 A1 | 5/2012 | Paul et al. |
| 2014/0010861 A1 | 1/2014 | Bancel et al. |
| 2015/0274835 A1 | 10/2015 | Marasco et al. |
| 2016/0215059 A1* | 7/2016 | Liu .................... C07K 16/2896 |

FOREIGN PATENT DOCUMENTS

| | | |
|---|---|---|
| EP | 1 374 902 A1 | 1/2004 |
| WO | WO 98/38216 A1 | 9/1998 |
| WO | WO 02/074803 A2 | 9/2002 |
| WO | WO 02/076504 A1 | 10/2002 |
| WO | WO 2008/137915 A2 | 11/2008 |
| WO | WO 2010/056804 A1 | 5/2010 |
| WO | WO 2011/041613 A2 | 4/2011 |
| WO | WO 2012/131004 A2 | 10/2012 |
| WO | WO 2014/033327 A1 | 3/2014 |
| WO | WO 2014/089113 A1 | 6/2014 |

OTHER PUBLICATIONS

Botturi, et al, "Differences in Allergen-induced T cell Activation between Allergic Asthma and Rhinitis: Role of CD28, ICOS and CTLA-4", *Respiratory Research*, 12:25 (2011).

Burmeister, et al., *J. Immunol.*, 180:774-782 (2008).

Carthon, et al., "Preoperative CTLA-4 blockade: tolerability and immune monitoring in the setting of a presurgical clinical trial", *Clin. Cancer Res.*, 16(10): 2861-71 (2010).

Chen, et al., "Anti-CTLA-4 therapy results in higher CD4+ICOS$^{hi}$ T cell frequency and IFN-gamma levels in both nonmalignant and malignant prostate tissues", *Proc. Natl. Acad. Sci.*, 106(8): 2729-34 (2009).

Deng, et al. "An agonist human ICOS monoclonal antibody that induces T cell activation and inhibits proliferation of a myeloma cell line", *Hybridoma and Hybridomics*, 23(3): 176-182 (2004).

Di Giacomo, et al., "Long-term survival and immunological parameters in metastatic melanoma patients who responded to ipilimumab 10 mg/kg within an expanded access programme", *Cancer Immunol. Immunother*, 62(6):1021-8 (2013).

Dong, et al., "ICOS co-stimulatory receptor is essential for T-cell activation and function", *Nature*, 409: 97-101 (2001).

Feito, et al., "Mechanisms of H4/ICOS costimulation: effects on proximal TCR signals and MAP kinase pathways", *Eur. J. Immunol.*, 33: 204-14 (2003).

Frey, et al. "Inducible costimulaltor (ICOS) blockade inhibitors accumulation of polyfuncitonal T helper 1/T helper 17 cells and mitigates autoimmune arthritis", *Ann. Rheum. Dis.*, 69: 1495-1501 (2010).

Fu, et al., "The ICOS/ICOSL pathway is required for optimal antitumor responses mediated by anti-CTLA-4 therapy", *Cancer Res.*, 71(16): 1-10 (2011).

Guo, et al "Simultaneous blockade of co-stimulatory signals, CD28 and ICOS, induced a stable tolerance in rat heart transplantation", *Transplant Immunology*, 12(1): 41-48 (2003).

Hall, et al., Immunoparalysis and nosocomial infection in children with multiple organ dysfunction syndrome, *Intensive Care Med.*, 37:525-532 (2011).

Hutloff, et al., "ICOS is an inducible T-cell co-stimulator structurally and functionally related to CD28", *Nature*, 397(6716): 263-266 (1999).

Izawa, et al., "A Novel alloantigen-specific CD8$^+$PD1$^+$ Regulatory T cell Induced by ICOS-B7h Blockade *in vivo*", *Journal of Immunology*, 179(2): 786-796 (2007).

Katsumata, et al., "Attenuation of experimental autoimmune myositis by blocking ICOS-ICOS ligand interaction", *Journal of Immunology*, 179(6): 3772-3779 (2007).

Kawamoto, et al., "Expression and function of inducible co-stimulator in patients with systemic lupus erythematosus: possible involvement in excessive interferon-gamma and anti-double-stranded DNA antibody production", *Arthritis Research & Therapy*, 8(3): R62.1-R62.14 (2006).

Kimura, et al., "IL-6 Regulator of Treg/Th17 balance", *Eur. J. Immunol.*, 40: 1830-1835 (2010).

Korn, et al., "IL-6 controls Th17 immunity in vivo by inhibiting the conversion of conventional T cells into Foxp3+ regulatory T cells", *PNAS*,105: 18460-18465 (2008).

Lee, et al., "Peripheral blood gene expression of B7 and CD28 family members associated with tumor progression and microscopic lymphovascular invasion in colon cancer patients", *J. Cancer Res. Clin. Oncol.*, 136(9): 1445-52 (2010).

Liakou, et al., "CTLA-4 blockade increases IFNgamma-producing CD4+ICOS$^{hi}$ cells to shift the ratio of effector to regulatory T cells in cancer patients", *Proc. Natl. Acad. Sci.*, 105(39): 14987-92 (2008).

Luhder, et al., "Topological Requirements and Signaling Properties of T Cell-activating, Anti-CD28 Antibody Superagonists", *J. Exp. Med*: 197(8): 955-966 (2003).

McAdam, et al., "ICOS is critical for CD40-mediated antibody class switching", *Nature*, 409(6816): 102-5 (2001).

Meisel, et al., "Granulocyte-macrophage colony-stimulating factor to reverse sepsis-associated immunosuppression: a double-blind, randomized, placebo-controlled multicenter trial", *Am. J. Respir. Crit. Care Med.*, 180: 640-648 (2009).

Nanji, et al. "Multiple combination therapies involving blockade of ICOS/B7RP-1 costimulation facilitate long-term islet allograft survival", *American Journal of Transplantation*, 4: 526-536 (2004).

Nelson, et al., "The inducible costimulator augments Tc17 cell responses to self and tumor tissue", *J. Immunol.*, 194: 1737-1747 (2015).

Nunez, S., et al., "T helper type 17 cells contribute to anti-tumour immunity and promote the recruitment of T helper type 1 cells to the tumour", *Immunology*, 139(1): 61-71 (2013).

Paulos, et al., "The inducible costimulator (ICOS) is critical for the development of human $T_H17$ cells", *Sci. Transl. Med*, 2(55); 55ra78 (2010).

Peng, et al. Transient blockade of the inducible costimulator pathway generates long-term tolerance to factor VIII after nonviral gene transfer into hemophilia A mice. *Blood*, 112(5): 1662-1672 (2008).

Rogers, et al., "CD28, OX-40, LFA-1, and CD4 Modulation of Th1/Th2 Differentiation Is Directly Dependent on the Dose of Antigen", *J. Immunol.*, 164:2955-2963, doi: 10.4049/jimmunol.164.6.2955 (2000).

Rutitzky, et al. "Disruption of the ICOS-B7RP-1 costimulatory pathway leads to enhanced hepatic immunopathology and increased gamma interferon production by CD4 T cells in murine schistomiasis", *Infection and Immunity*, 71(7): 4040-4044 (2003).

Sharpe, et al., "The B7-CD28 Superfamily", *Nat. Rev. Immunol.*, 2(2): 116-26 (2002).

Stebbings, et al., "Cytokine Storm" in the Phase I Trial of Monoclonal Antibody TGN1412: Better Understanding the Causes to Improve PreClinical Testing of Immunotherapeutics, *J. Immunol.*, 179: 3325-3331 (2007).

Strauss, et al., "Expression of ICOS on human melanoma-infiltrating CD4+CD25$^{high}$Foxp3$^+$T regulatory cells: implications and impact on tumor-mediated immune suppression", *J. Immunol.*, 180(5): 2967-80 (2008).

Tajima, et al "JTA-009, a fully human antibody against human AILIM/ICOS, ameliorates graft-vs-host reaction in SCID mice grafted with human PBMCs", *Experimental Hematology*, 36(11): 1514-1523 (2008).

Tezuka, et al., "Identification and characterization of rat AILIM/ICOS, a novel T-cell costimulatory molecule, related to the CD28/CTLA4 family", *Biochem. Biophys. Res. Commun.*, 276: 335-345 (2000).

(56) References Cited

OTHER PUBLICATIONS

Totsuka, et al., "Amerliorating effect of anti-inducible costimulator monoclonal antibody in a murine model of chronic colitis", *Gastroenterology*, 124(2): 410-421 (2003).

Vonderheide, et al., "Tremelimumab in combination with exemestane in patients with advanced breast cancer and treatment-associated modulation of inducible costimulator expression on patient T cells", *Clin. Cancer Res.* 16(13): 3485-94 (2010).

Wakamatsu, et al., "Convergent and divergent effects of costimulatory molecules in conventional and regulatory CD4+ T cells", *Proc. Natl. Acad. Sci.*, 110(3); 1023-8 (2013).

White, et al., "Conformation of the Human Immunoglobulin G2 Hinge Imparts Superagonistic Properties to Immunostimulatory Anticancer Antibodies", *Cancer Cell*, , 27: 138-148 (2015).

Wilely, et al. "Evaluation of inducible costimulatory/B7-related protein-1 as a therapeutic target in a murine model of allergic airway inflammation", *American Journal of Respiratory Cell and Molecular Biology*, 28(6): 722-730 (2003).

Yao, et al., "B7-H2 is a costimulatory ligand for CD28 in human", *Immunity*, 34(5); 729-40 (2011).

Yoshinaga, et al., T-cell co-stimulation through B7RP-1 and ICOS, *Nature*, 402:827-832 (1999).

\* cited by examiner

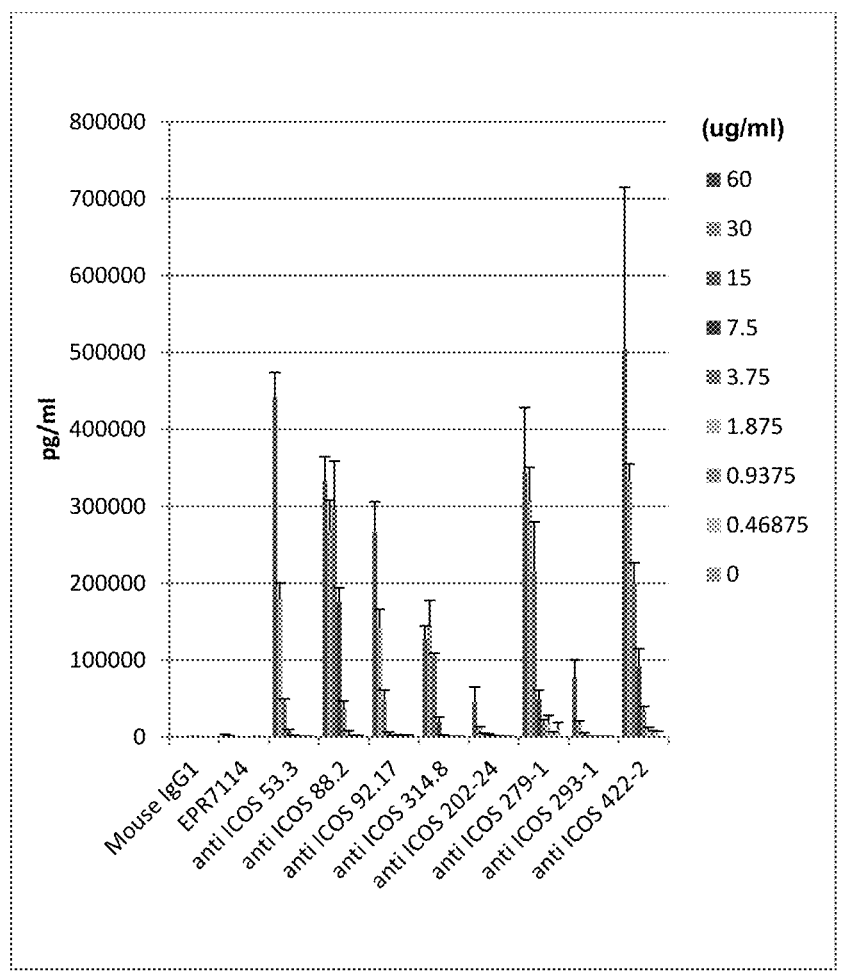
Figure 1: IFN-γ production from CD4+CD25- T cells

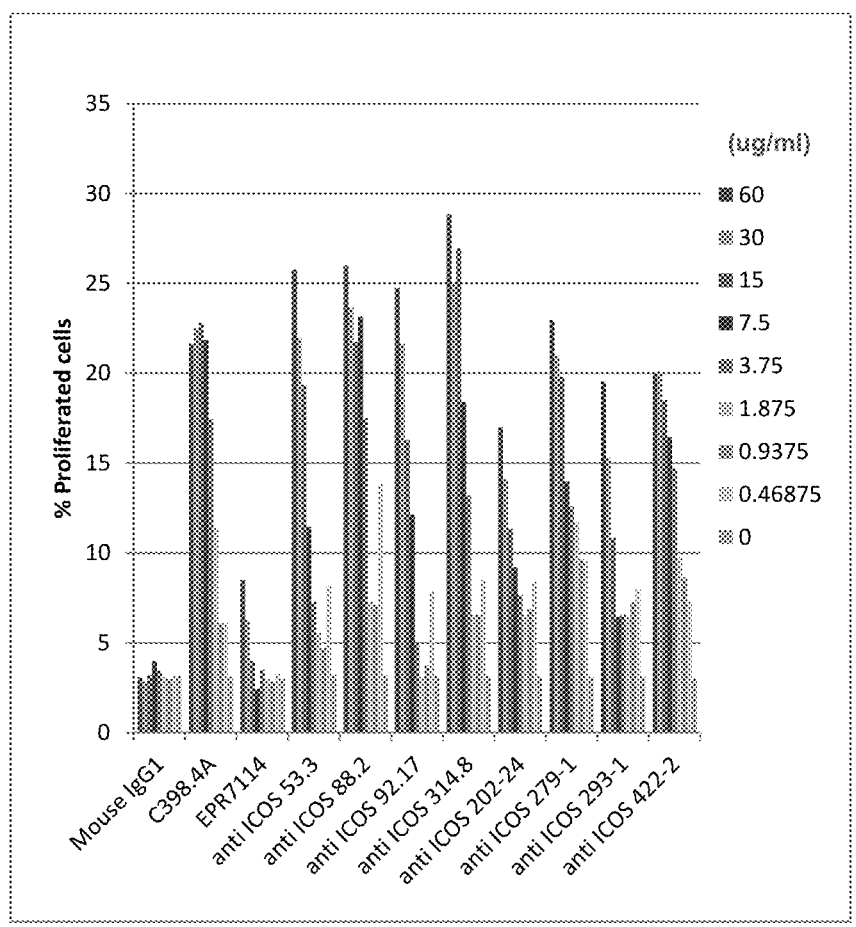
Figure 2: Proliferation in CD4+CD25- T cells

Figure 3: H2L5 humanized variant of anti-ICOS 422.2 shows better cytokine production in PBMC cells
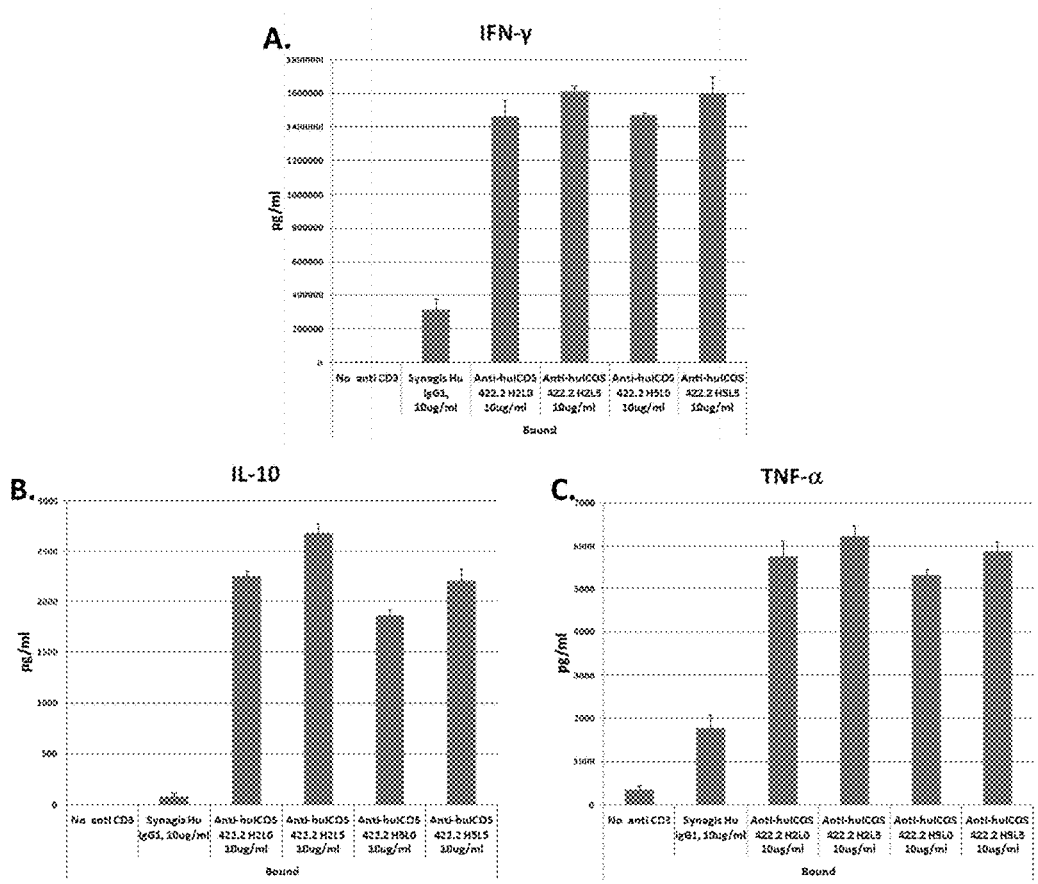
Human PBMCs were freshly isolated from healthy human donor and activated on plates pre-coated with anti-CD3 (OKT3) and each of the four soluble anti ICOS 422.2 humanized variants. After treatment for 2.5 days, the amounts of IFN-☐ (A), IL-10 (B) and TFN-☐ (C) in supernatant were measured by MSD.

Figure 4:  422 H2L5 IgG1 induced decreased T cell viability which was not apparent with Fc-disabled or hIgG4PE isotypes.
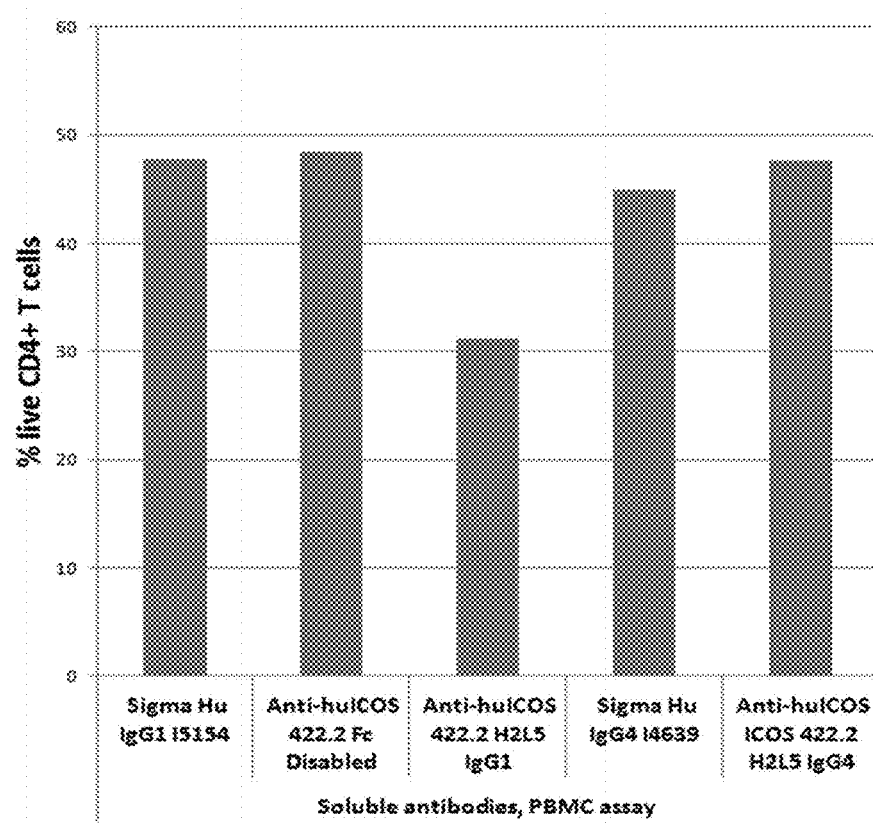
Human PBMCs were freshly activated on plates pre-coated with anti-CD3 (OKT3) and soluble humanized anti ICOS 422.2 with different Fc isotype. After treatment for 2.5 days, the percentages of live CD4+ T cells were measured by Flow cytometry.

Figure 5: Dose response of H2L5 hIgG4PE induced proinflammatory cytokine induction in human CD4+ T cells.

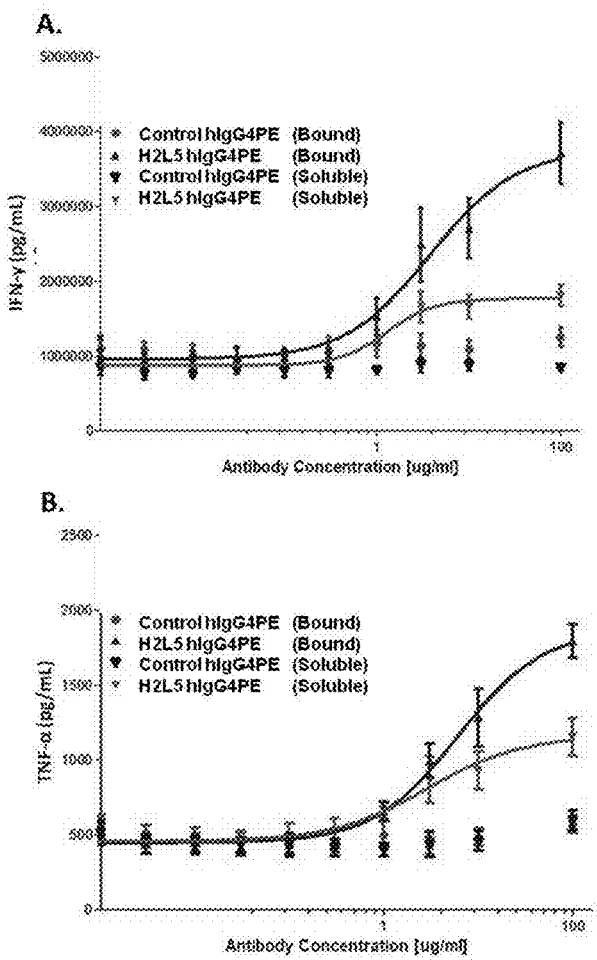

Human healthy donor CD4+ T cells pre-stimulated with anti-CD3/CD28 for 2 days were re-stimulated by anti-CD3 (OKT3) plus serial concentrations of isotype control (Synagis IgG4PE) or H2L5 hIgG4PE mAb as plate bound or soluble format. The concentration of (A) IFN-γ and (B) TFN-α was measured in the supernatants by MSD after 3.5 days of treatment.

Figure 6: H2L5 hIgG4PE induces proliferation, cytokine production and increased cytotoxic potential in activated PBMCs from healthy human donors

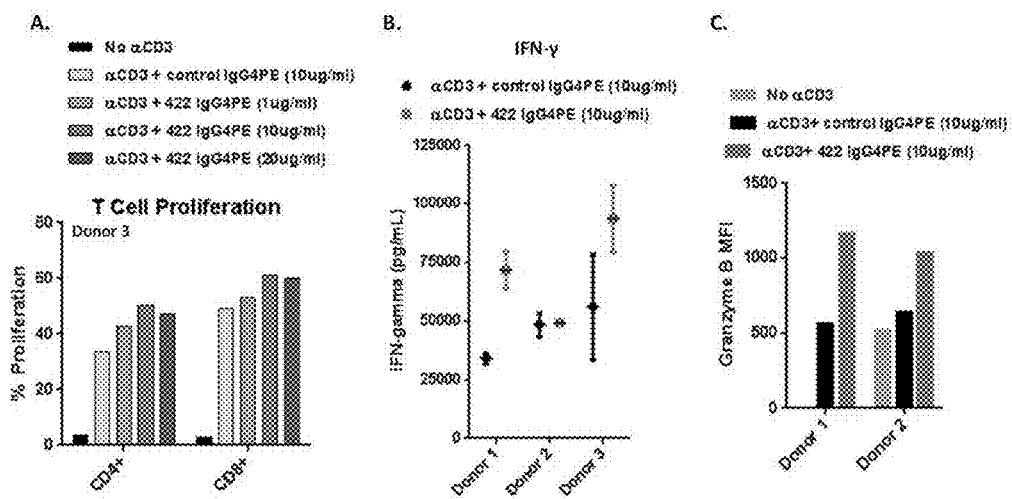

Human PBMC cells pre-stimulated with anti-CD3/CD28 for 2 days were re-stimulated by anti-CD3 (OKT3) plus soluble H2L5 hIgG4PE mAb or isotype control. After 2.5 days of treatment, T cell proliferation was measured by CFSE FACS assay (A). IFN-γ concentration in the supernatants was measured by MSD (B). Intracelluar Granzyme B expression of CD4+ T cells was measured by flow cytometry.

Figure 7: Meso Scale Discovery (MSD) assay showing the inhibition of ICOS-L binding to ICOS by H2L5 hIgG4PE, indicating that it binds to the same epitope on ICOS as ICOS-L and competes for binding
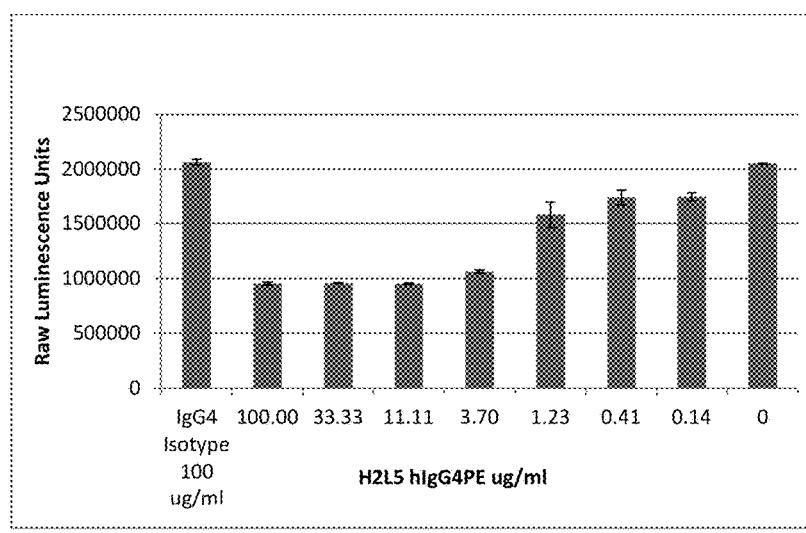

Figure 8: Recovered antibody $V_H$ and $V_L$ genes from RNA of hybridoma clone 422.2

422 HC

QVQLQQSGPELVRPGESVKISCMGSGYTFTDYAMHWVKQSHAKSLEWIGLISIYSDH
TNYNQKFQGKATMTVDKSSSTAYMELARLTSEDSAIYYCGRNNYGNYGWYFDVW
GAGTTVTVSS (SEQ ID NO:19)

422 LC

ENVLTQSPAIMSASPGEKVTMTCSASSSVSYMHWYQQKSITSPKLWIYDTSKLASGV
PGRFSGSGSGNSYSLTISSMEAEDVATYYCFQGSGYPYTFGGGTKLEIKR (SEQ ID
NO:20)

Figure 9: Protein sequences of heavy and light chains of H2L5 hIgG4PE with signal sequence Heavy chain MGWSCIILFLVATATGVHSQVQLVQSGAEVKKPGSSVKVSCKASGYTFTDYAMHW
VRQAPGQGLEWMGLISIYSDHTNYNQKFQGRVTITADKSTSTAYMELSSLRSEDTAV
YYCGRNNYGNYGWYFDVWGQGTTVTVSSASTKGPSVFPLAPCSRSTSESTAALGCL
VKDYFPEPVTVSWNSGALTSGVHTFPAVLQSSGLYSLSSVVTVPSSSLGTKTYTCNV
DHKPSNTKVDKRVESKYGPPCPPCPAPEFEGGPSVFLFPPKPKDTLMISRTPEVTCVV
VDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEAL
HNHYTQKSLSLSLGK (SEQ ID NO:9)

Light chain

MGWSCIILFLVATATGVHSEIVLTQSPATLSLSPGERATLSCSASSSVSYMHWYQQKP
GQAPRLLIYDTSKLASGIPARFSGSGSGTDYTLTISSLEPEDFAVYYCFQGSGYPYTFG
QGTKLEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGE
C (SEQ ID NO:12)

Signal Sequence is double underlined

CDR sequences are underlined

S228P, L235E (EU numbering) Substitutions in IgG4

Murine residues incorporated in variable heavy chain framework (Kabat numbering G27Y, S30T, A93G)

Murine residue incorporated in variable light chain framework (Kabat numbering F71Y)

Figure 10: DNA sequence of coding region of H2L5 hIgG4PE heavy chain with signal sequence Heavy Chain <u><u>ATGGGCTGGTCCTGCATCATCCTGTTTCTGGTGGCCACCGCCACCGGCGTGCACA</u></u>
<u><u>GCC</u></u>AGGTGCAGCTGGTGCAGAGCGGAGCCGAGGTGAAAAAGCCCGGCTCAAGC
GTGAAGGTGAGCTGCAAGGCCAGCGGCTACACCTTCACCGACTACGCTATGCAC
TGGGTGAGGCAGGCCCCCGGCCAGGGCCTGGAGTGGATGGGCCTGATCAGCATC
TACAGCGACCACACCAACTACAACCAGAAGTTCCAGGGCAGGGTGACCATCACC
GCCGATAAGAGCACCAGCACAGCCTACATGGAGCTGAGCAGCCTGAGGAGCGA
AGACACCGCCGTGTACTATTGCGGCAGGAACAACTACGGCAACTACGGCTGGTA
CTTCGACGTGTGGGGCCAGGGAACCACTGTCACCGTGAGCAGCGCCAGCACCAA
GGGCCCCAGCGTGTTCCCCCTGGCCCCCTGCAGCAGAAGCACCAGCGAGAGCAC
AGCCGCCCTGGGCTGCCTGGTGAAGGACTACTTCCCCGAGCCCGTGACCGTGAG
CTGGAACAGCGGAGCCCTGACCAGCGGCGTGCACACCTTCCCCGCCGTGCTGCA
GAGCAGCGGCCTGTACAGCCTGAGCAGCGTGGTGACCGTGCCCAGCAGCAGCCT
GGGCACCAAGACCTACACCTGCAACGTGGACCACAAGCCCAGCAACACCAAGGT
GGACAAGCGGGTGGAGAGCAAGTACGGCCCTCCCTGCCCCCCTGCCCTGCCCC
CGAGTTCGAGGGCGGACCCTCCGTGTTCCTGTTCCCCCCCAAGCCCAAGGACACC
CTGATGATCAGCCGGACCCCCGAGGTGACCTGCGTGGTGGTGGACGTGAGCCAG
GAAGATCCCGAGGTCCAGTTCAATTGGTACGTGGACGGCGTGGAGGTGCACAAC
GCCAAGACCAAGCCCCGGGAGGAACAGTTCAACAGCACCTACCGGGTGGTGTCC
GTGCTGACCGTGCTGCACCAGGACTGGCTGAACGGCAAAGAATACAAGTGCAAG
GTGTCCAACAAGGGCCTGCCCAGCTCCATCGAGAAAACCATCAGCAAGGCCAAG
GGCCAGCCTCGGGAGCCCCAGGTGTACACCCTGCCCCCATCCCAGGAAGAGATG
ACCAAGAACCAGGTGTCCCTGACCTGTCTGGTGAAGGGCTTCTACCCCAGCGAC
ATCGCCGTGGAGTGGGAGAGCAACGGCCAGCCCGAGAACAACTACAAGACCAC
CCCCCCTGTGCTGGACAGCGACGGCAGCTTCTTCCTGTACAGCAGGCTGACCGTG
GACAAGAGCCGGTGGCAGGAAGGCAACGTCTTTAGCTGCAGCGTGATGCACGAG
GCCCTGCACAACCACTACACCCAGAAGAGCCTGAGCCTGTCCCTGGGCAAG
(SEQ ID NO:21)

Leader sequence indicated by double underline

Figure 11: DNA sequence of coding region of H2L5 hIGg4PE light chain with signal sequence Light Chain <u>ATGGGCTGGTCCTGCATCATCCTGTTTCTGGTGGCCACCGCCACCGGCGTGCACA</u>
<u>GC</u>GAGATTGTGCTGACCCAGAGCCCCGCCACCCTGAGCCTGAGCCCCGGCGAAA
GGGCAACCCTCAGCTGCAGCGCCAGCAGCAGCGTGAGCTACATGCACTGGTACC
AGCAGAAGCCCGGCCAGGCCCCTAGGCTGCTGATCTACGACACCTCCAAGCTGG
CCAGCGGCATCCCAGCCAGGTTCTCAGGCAGCGGCAGCGGCACCGACTATACTC
TGACCATCAGCAGCCTGGAGCCCGAGGACTTCGCCGTGTACTACTGCTTCCAGGG
AAGCGGCTACCCCTACACCTTCGGCCAGGGCACCAAGCTGGAGATCAAGCGTAC
GGTGGCCGCCCCCAGCGTGTTCATCTTCCCCCCCAGCGATGAGCAGCTGAAGAGC
GGCACCGCCAGCGTGGTGTGTCTGCTGAACAACTTCTACCCCGGGAGGCCAAG
GTGCAGTGGAAGGTGGACAATGCCCTGCAGAGCGGCAACAGCCAGGAGAGCGT
GACCGAGCAGGACAGCAAGGACTCCACCTACAGCCTGAGCAGCACCCTGACCCT
GAGCAAGGCCGACTACGAGAAGCACAAGGTGTACGCCTGTGAGGTGACCCACCA
GGGCCTGTCCAGCCCCGTGACCAAGAGCTTCAACCGGGGCGAGTGC (SEQ ID
NO:22)

Leader sequence indicated by double underline

Figure 12: Plasma concentrations of H2L5 hIgG4PE in cynomolgus monkeys. Concentrations were determined after the (A) first or (B) second dose (day 15) of H2L5 hIgG4PE. Animals were sacrificed 48 hours post second dose for tissue sample collection and histopath analysis
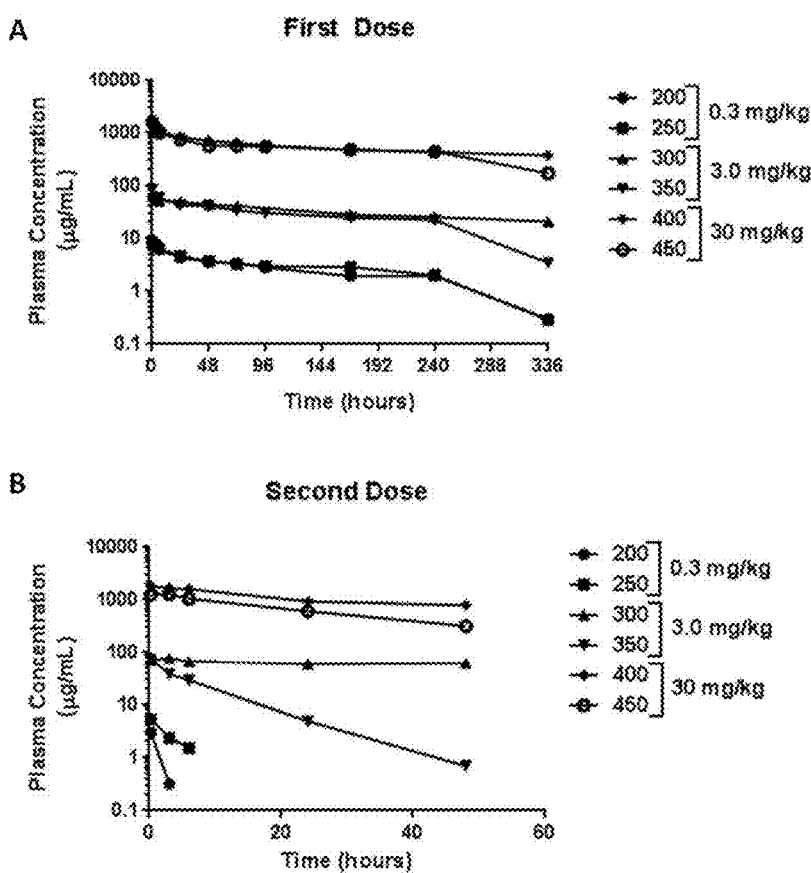

Figure 13: Detection of H2L5 hIgG4PE binding to CD4+ T cells from the spleen and axillary lymph nodes of monkeys. Tissue was collected 48 hours post-second dose (Day 17).
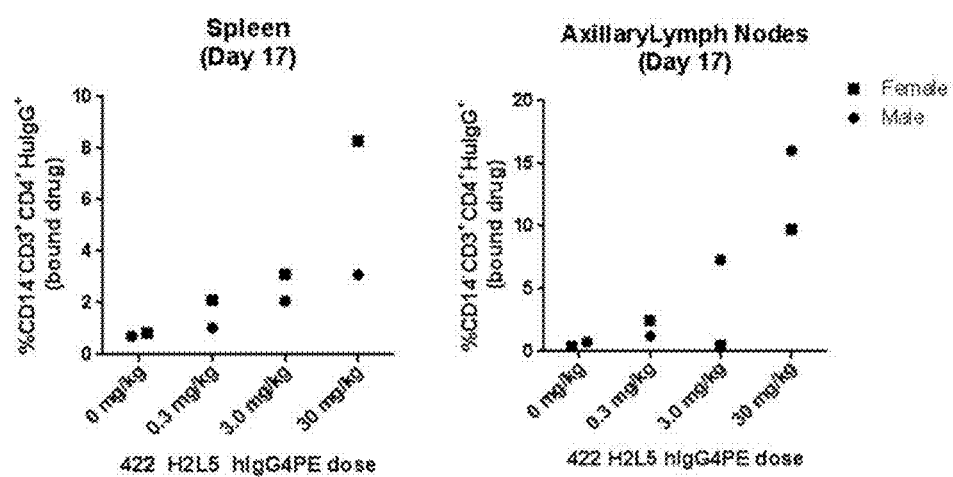

Figure 14: Receptor Occupancy of H2L5 hIgG4PE in blood CD4+ T cells from cyno monkeys.

(A) ICOS "free receptor" as measured by positive binding of the anti-ICOS fluorescently labeled antibody used for flow cytometry, which binds only when H2L5 hIgG4PE is not present.

(B) Receptor bound H2L5 hIgG4PE on peripheral blood CD4+ cells as measured by fluorescently labeled anti-Human IgG.

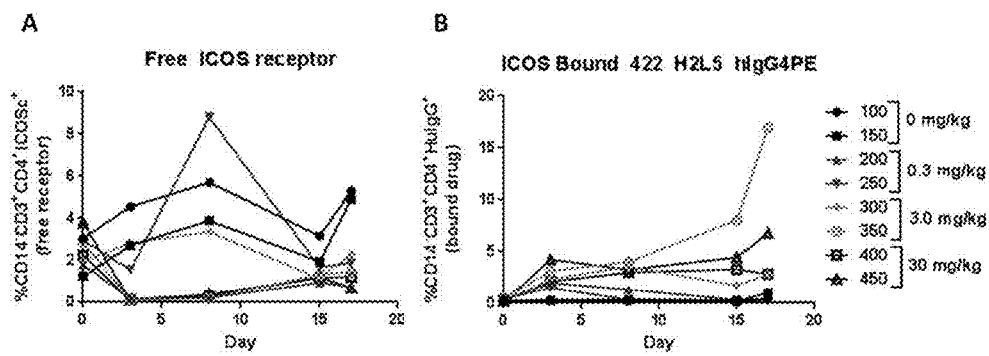

Figure 15(a) Phospho-AKT (T308) expression levels in Ba/F3-ICOS cells treated with H2L5 hIgG4PE - Intracellular signalling antibody array
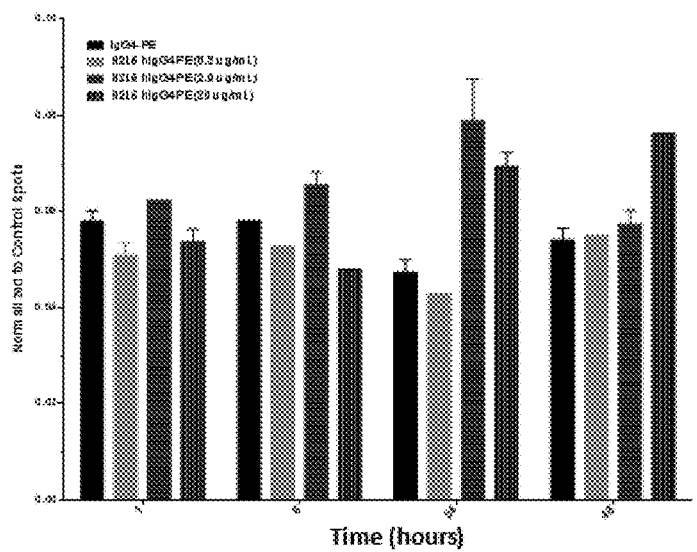
Figure 15 (b) Phospho-AKT (S473) expression levels in Ba/F3-ICOS cells treated with H2L5 hIgG4PE - Intracellular signalling antibody array
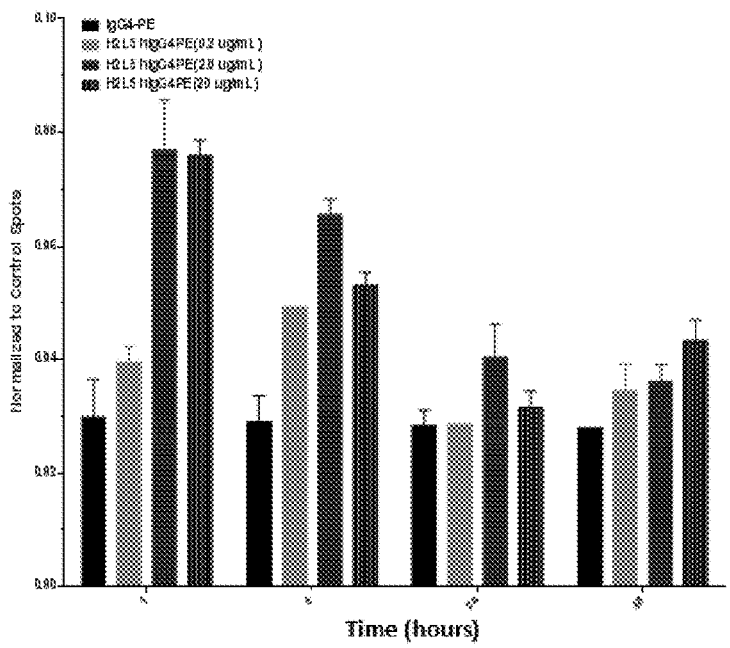

Figure 16: H2L5 hIgG4PE in combination with ipilimumab results increased proinflammatory cytokine production as compared to single antibody treatment in PBMC pre-stimulation assay
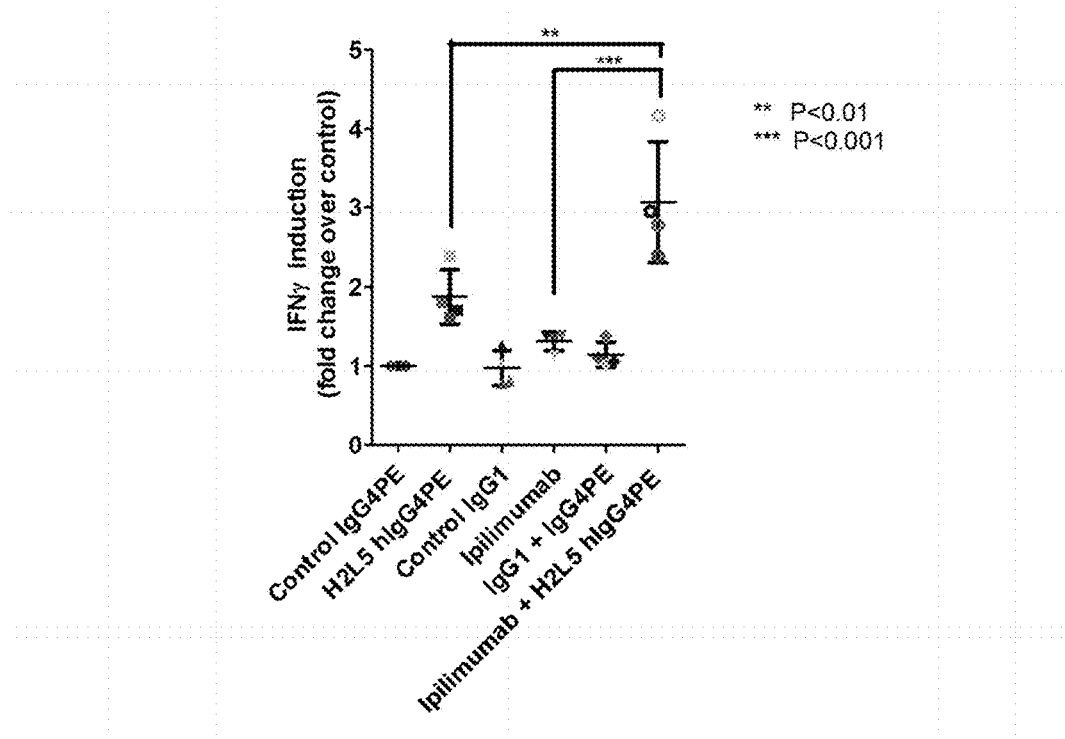

Figure 17: H2L5 hIgG4PE in combination with pembrolizumab results increased proinflammatory cytokine production as compared to single antibody treatment in PBMC pre-stimulation assay
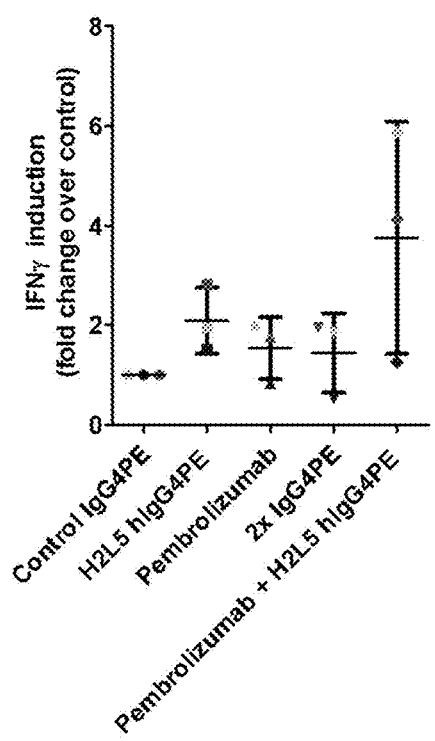

Figure 18    H2L5 hIgG4PE plus ipilimumab combination induces increased proinflamatory cytokine production in a modified MLR assay with CEFT peptide and pre-incubation
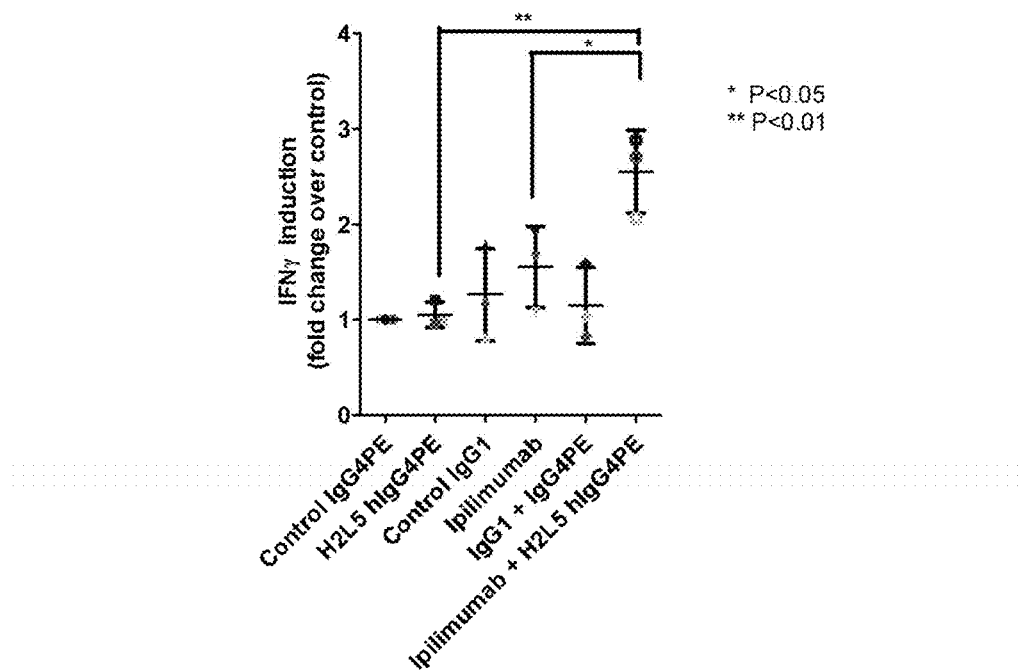

Figure 19     H2L5 hIgG4PE plus pembrolizumab combination induces increased proinflamatory cytokine production in a modified MLR assay with CEFT peptide and pre-incubation
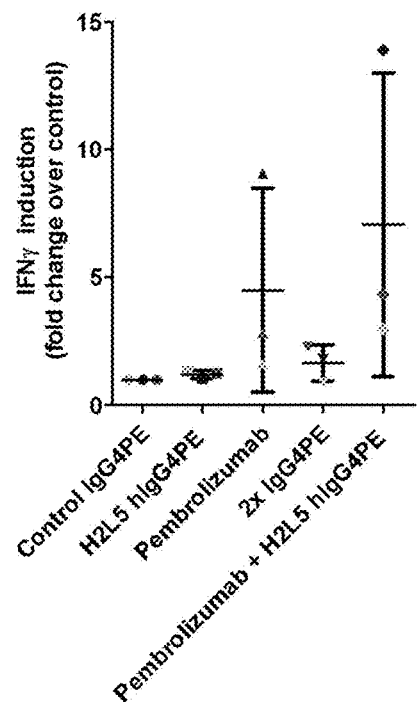

Figure 20: H2L5 hIgG4PE anti-ICOS agonist mAb alone and in combination with pembrolizumab results in tumor growth inhibition in a human PBMC A2058 Melanoma mouse tumor model
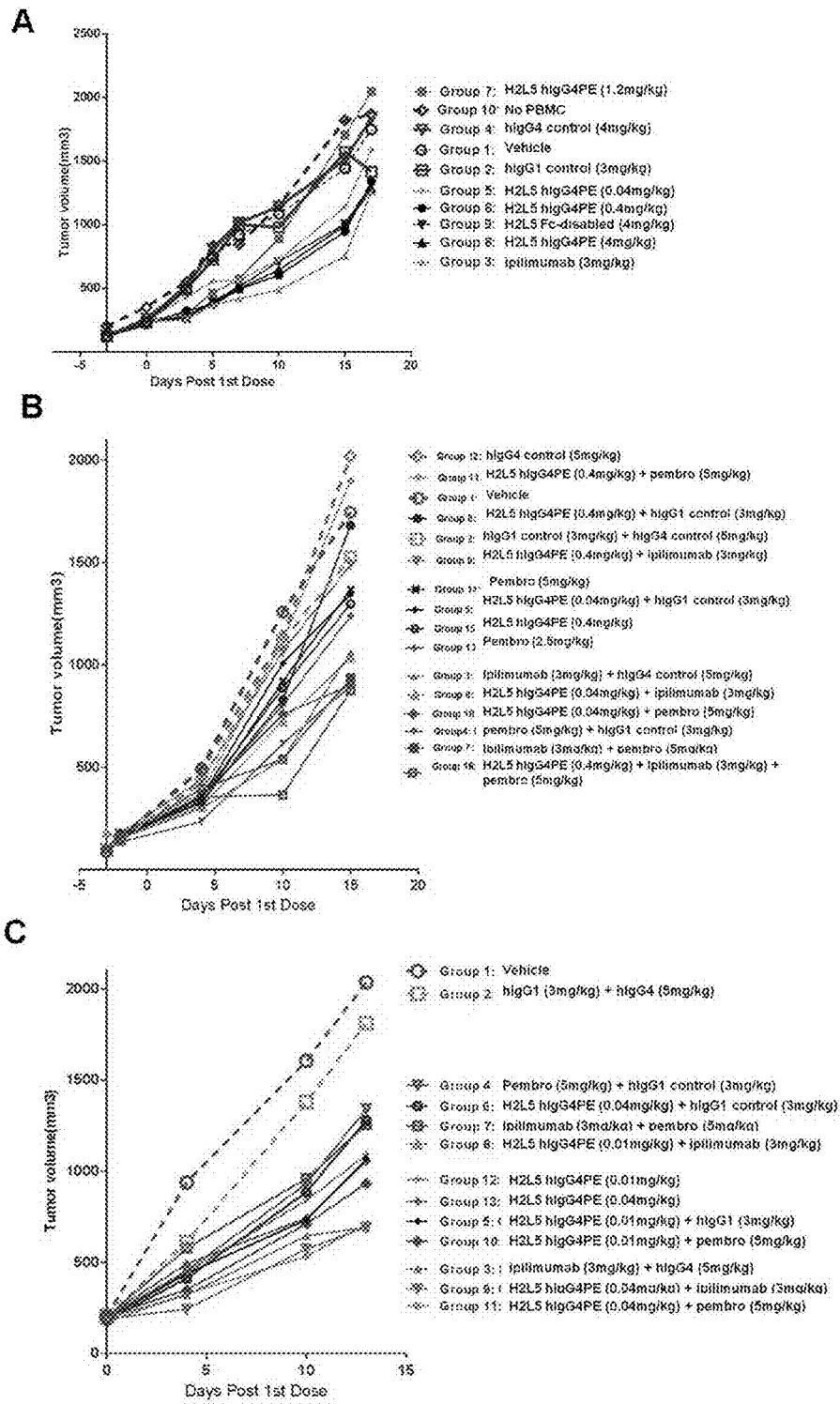

Figure 21A: anti-ICOS murine surrogate mAb results in significant tumor growth inhibition and increased survival in combination with an anti-PD1 murine surrogate mAb in the CT26 mouse tumor model
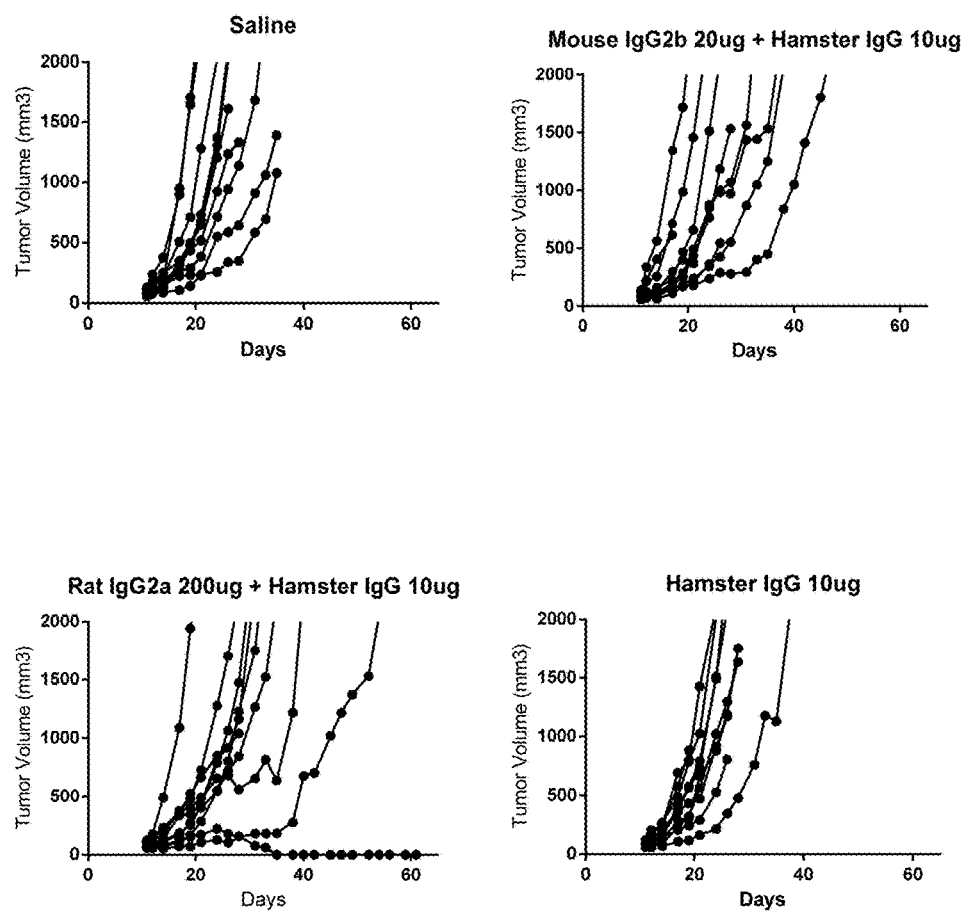

Figure 22A: anti-ICOS murine surrogate mAb results in significant tumor growth inhibition and increased survival in combination with an anti-PD1 murine surrogate mAb in the EMT6 mouse tumor model
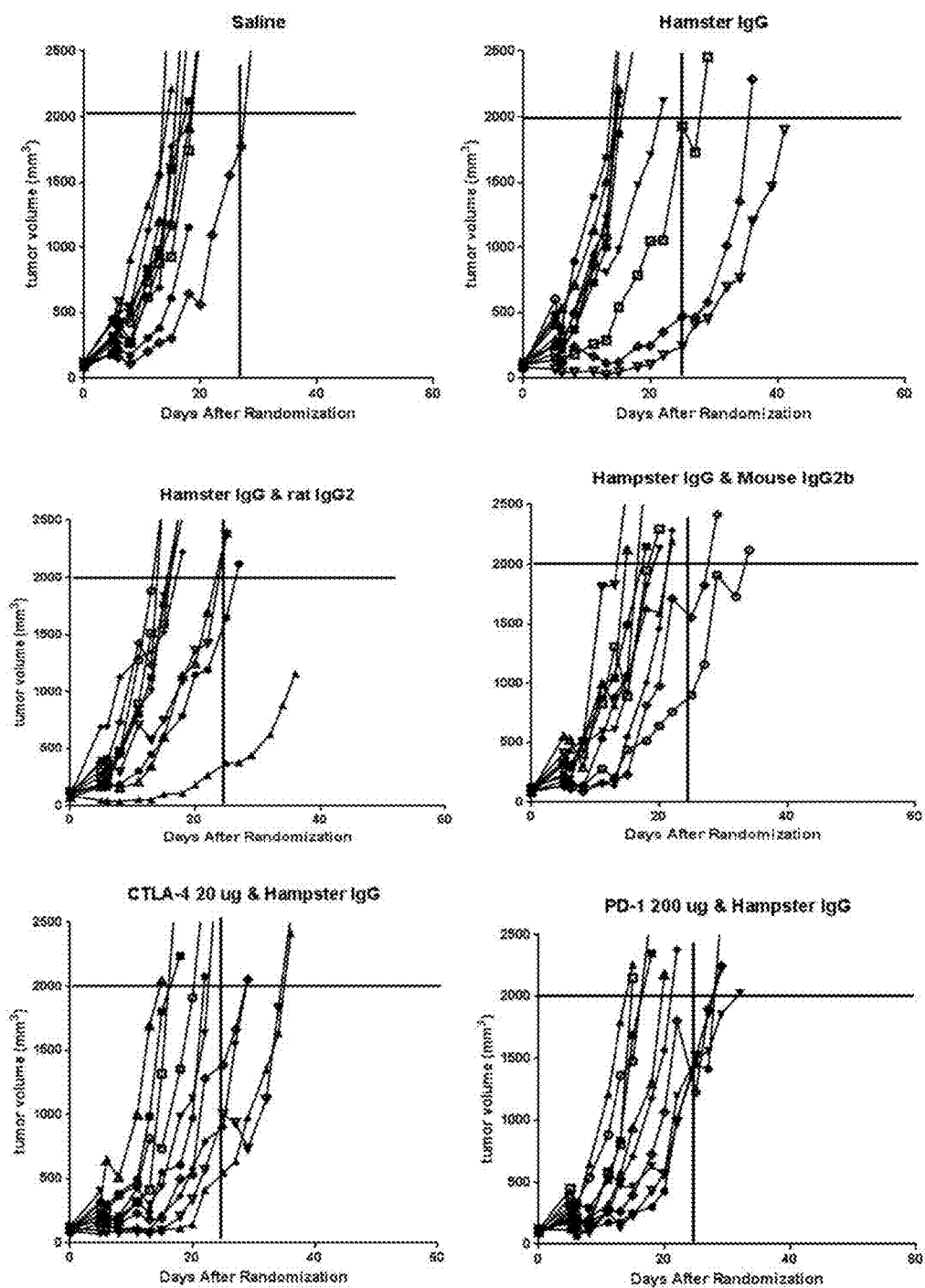

ICOS BINDING PROTEINS

This application is a continuation of U.S. application Ser. No. 15/246,662 filed 25 Aug. 2016, which is a divisional of U.S. application Ser. No. 15/006,560 filed 26 Jan. 2016, which is a 111a application which claims benefit of U.S. Provisional 62/247,355 filed 28 Oct. 2015, U.S. Provisional 62/192,331 filed 14 Jul. 2015, and U.S. Provisional 62/108,605 filed 28 Jan. 2015. The entire teachings of the above applications are incorporated herein by reference.

FIELD OF THE INVENTION

The present invention relates generally to immunotherapy in the treatment of human disease and reduction of adverse events related thereto. More specifically, the present invention relates to the use of ICOS binding proteins including ICOS agonist antibodies and their use as immunomodulators in the treatment of cancer, infectious disease and/or sepsis.

BACKGROUND OF THE INVENTION

Enhancing anti-tumor T cell function and inducing T cell proliferation is a powerful and new approach for cancer treatment. Three immune-oncology antibodies (e.g., immuno-modulators) are presently marketed. Anti-CTLA-4 (YERVOY/ipilimumab) is thought to augment immune responses at the point of T cell priming and anti-PD-1 antibodies (OPDIVO/nivolumab and KEYTRUDA/pembrolizumab) are thought to act in the local tumor microenvironment, by relieving an inhibitory checkpoint in tumor specific T cells that have already been primed and activated.

ICOS is a co-stimulatory T cell receptor with structural and functional relation to the CD28/CTLA-4-Ig superfamily (Hutloff, et al., "ICOS is an inducible T-cell co-stimulator structurally and functionally related to CD28", Nature, 397: 263-266 (1999)). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao S et al., "B7-H2 is a costimulatory ligand for CD28 in human", Immunity, 34(5); 729-40 (2011)). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naïve $T_H1$ and $T_H2$ effector T cell populations (Paulos C M et al., "The inducible costimulator (ICOS) is critical for the development of human Th17 cells", Sci Transl Med, 2(55); 55ra78 (2010)). ICOS expression is highly induced on CD4+ and CD8+ effector T cells following activation through TCR engagement (Wakamatsu E, et al., "Convergent and divergent effects of costimulatory molecules in conventional and regulatory CD4+ T cells", Proc Natal Acad Sci USA, 110(3); 1023-8 (2013)). Co-stimulatory signalling through ICOS receptor only occurs in T cells receiving a concurrent TCR activation signal (Sharpe A H and Freeman G J. "The B7-CD28 Superfamily", Nat. Rev Immunol, 2(2); 116-26 (2002)). In activated antigen specific T cells, ICOS regulates the production of both $T_H1$ and $T_H2$ cytokines including IFN-γ, TNF-α, IL-10, IL-4, IL-13 and others. ICOS also stimulates effector T cell proliferation, albeit to a lesser extent than CD28 (Sharpe A H and Freeman G J. "The B7-CD28 Superfamily", Nat. Rev Immunol, 2(2); 116-26 (2002))

A growing body of literature supports the idea that activating ICOS on CD4+ and CD8+ effector T cells has anti-tumor potential. An ICOS-L-Fc fusion protein caused tumor growth delay and complete tumor eradication in mice with SA-1 (sarcoma), Meth A (fibrosarcoma), EMT6 (breast) and P815 (mastocytoma) and EL-4 (plasmacytoma) syngeneic tumors, whereas no activity was observed in the B16-F10 (melanoma) tumor model which is known to be poorly immunogenic (Ara G et al., "Potent activity of soluble B7RP-1-Fc in therapy of murine tumors in syngeneic hosts", Int. J Cancer, 103(4); 501-7 (2003)). The anti-tumor activity of ICOS-L-Fc was dependent upon an intact immune response, as the activity was completely lost in tumors grown in nude mice. Analysis of tumors from ICOS-L-Fc treated mice demonstrated a significant increase in CD4+ and CD8+ T cell infiltration in tumors responsive to treatment, supporting the immunostimulatory effect of ICOS-L-Fc in these models.

Another report using $ICOS^{-/-}$ and $ICOS-L^{-/-}$ mice demonstrated the requirement of ICOS signalling in mediating the anti-tumor activity of an anti-CTLA4 antibody in the B16/B16 melanoma syngeneic tumor model (Fu T et al., "The ICOS/ICOSL pathway is required for optimal antitumor responses mediated by anti-CTLA-4 therapy", Cancer Res, 71(16); 5445-54 (2011)). Mice lacking ICOS or ICOS-L had significantly decreased survival rates as compared to wild-type mice after anti-CTLA4 antibody treatment. In a separate study, B16/B16 tumor cells were transduced to overexpress recombinant murine ICOS-L. These tumors were found to be significantly more sensitive to anti-CTLA4 treatment as compared to a B16/B16 tumor cells transduced with a control protein (Allison J et al., "Combination immunotherapy for the treatment of cancer", WO2011/041613 A2 (2009)). These studies provide evidence of the anti-tumor potential of an ICOS agonist, both alone and in combination with other immunomodulatory antibodies.

Emerging data from patients treated with anti-CTLA4 antibodies also point to the positive role of ICOS+ effector T cells in mediating an anti-tumor immune response. Patients with metastatic melanoma (Giacomo A M D et al., "Long-term survival and immunological parameters in metastatic melanoma patients who respond to ipilimumab 10 mg/kg within an expanded access program", Cancer Immunol Immunother., 62(6); 1021-8 (2013)); urothelial (Carthon B C et al., "Preoperative CTLA-4 blockade: Tolerability and immune monitoring in the setting of a presurgical clinical trial" Clin Cancer Res., 16(10); 2861-71 (2010)); breast (Vonderheide R H et al., "Tremelimumab in combination with exemestane in patients with advanced breast cancer and treatment-associated modulation of inducible costimulator expression on patient T cells", Clin Cancer Res., 16(13); 3485-94 (2010)); and prostate cancer which have increased absolute counts of circulating and tumor infiltrating $CD4^+ICOS^+$ and CD8+ICOS+ T cells after ipilimumab treatment have significantly better treatment related outcomes than patients where little or no increases are observed. Importantly, it was shown that ipilimumab changes the $ICOS^+$ T effector:$T_{reg}$ ratio, reversing an abundance of $T_{regs}$ pre-treatment to a significant abundance of T effectors vs. $T_{regs}$ following treatment (Liakou C I et al., "CTLA-4 blockade increases IFN-gamma producing CD4+ICOShi cells to shift the ratio of effector to regulatory T cells in cancer patients", Proc Natl Acad Sci USA. 105(39); 14987-92 (2008)) and (Vonderheide R H et al., Clin Cancer Res., 16(13); 3485-94 (2010)). Therefore, ICOS positive T effector cells are a positive predictive biomarker of ipilimumab response which points to the potential advantage of activating this population of cells with an agonist ICOS antibody.

Thus, there is a need for additional T cell proliferation inducing molecules in the treatment of cancer.

SUMMARY OF THE INVENTION

In one embodiment of the present invention, ICOS binding proteins or antigen binding portions thereof are provided comprising one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR.

In one embodiment of the present invention, ICOS binding proteins or antigen binding portions thereof are provided which specifically binds to human ICOS wherein said ICOS binding protein comprises a $V_H$ domain comprising an amino acid sequence at least 90% identical to the amino acid sequence set forth in SEQ ID NO:7 and/or a $V_L$ domain comprising an amino acid sequence at least 90% identical to the amino acid sequence set forth in SEQ ID NO:8.

In one embodiment, humanized monoclonal antibodies or antigen binding portions thereof are provided comprising heavy chain CDRs having the amino acid sequences set forth in SEQ ID NO:1; SEQ ID NO:2; and SEQ ID NO:3 and light chain CDRs having the amino acid sequences set forth in SEQ ID NO:4; SEQ ID NO:5; and SEQ ID NO:6. In one embodiment, humanized monoclonal antibodies are provided which comprise a hIgG4PE scaffold; a $V_H$ domain comprising an amino acid sequence set forth in SEQ ID NO:7; and a $V_L$ domain comprising an amino acid sequence set forth in SEQ ID NO:8. The antibodies of the present invention may stimulate cytokine production when contacted with a T cell.

In one embodiment, ICOS binding proteins are provided that compete for binding to human ICOS with any one of the ICOS binding proteins or antigen binding portions thereof of the invention.

In one embodiment, methods are provided for treating cancer, infectious disease and/or sepsis with an ICOS binding protein or a pharmaceutical composition comprising at least one ICOS binding protein of the present invention.

BRIEF DESCRIPTION OF THE DRAWINGS

FIG. 1: IFN-γ production from CD4+CD25− T cells.

FIG. 2: Proliferation in CD4+CD25− T cells.

FIG. 3A, FIG. 3B, FIG. 3C: H2L5 humanized variant of anti-ICOS 422.2 shows better cytokine production in PBMC cells.

FIG. 4: 422 H2L5 IgG1 induced decreased T cell viability which was not apparent with Fc-disabled or hIgG4PE isotypes.

FIG. 5A and FIG. 5B: Dose response of H2L5 hIgG4PE induced proinflammatory cytokine induction in human CD4+ T cells.

FIG. 6A, FIG. 6B, FIG. 6C: H2L5 hIgG4PE induces proliferation, cytokine production and increased cytotoxic potential in activated PBMCs from healthy human donors.

FIG. 7: Meso Scale Discovery (MSD) assay showing the inhibition of ICOS-L binding to ICOS by H2L5 hIgG4PE, indicating that it binds to the same epitope on ICOS as ICOS-L and competes for binding.

FIG. 8: Recovered antibody $V_H$ and $V_L$ genes from RNA of hybridoma clone 422.2.

FIG. 9: Protein sequences of heavy and light chains of H2L5 hIgG4PE with signal sequence.

FIG. 10: DNA sequence of coding region of H2L5 hIgG4PE heavy chain with signal sequence.

FIG. 11: DNA sequence of coding region of H2L5 hIgG4PE light chain with signal sequence.

FIG. 12A and FIG. 12B: Plasma concentrations of H2L5 hIgG4PE in cynomolgus monkeys. Concentrations were determined after the (A) first or (B) second dose (day 15) of H2L5 hIgG4PE. Animals were sacrificed 48 hours post second dose for tissue sample collection and histopathology analysis.

FIG. 13: Detection of H2L5 hIgG4PE binding to CD4+ T cells from the spleen and axillary lymph nodes of monkeys. Tissue was collected 48 hours post-second dose (Day 17).

FIG. 14A and FIG. 14B: Receptor Occupancy of H2L5 hIgG4PE in blood CD4+ T cells from cynomolgus monkeys.

FIG. 14A: ICOS "free receptor" as measured by positive binding of the anti-ICOS fluorescently labelled antibody used for flow cytometry, which binds only when H2L5 hIgG4PE is not present.

FIG. 14B: Receptor bound H2L5 hIgG4PE on peripheral blood CD4+ cells as measured by fluorescently labelled anti-Human IgG.

FIG. 15 (a) Phospho-AKT (T308) expression levels in Ba/F3-ICOS cells treated with H2L5 hIgG4PE—Intracellular signalling antibody array; FIG. 15 (b) Phospho-AKT (S473) expression levels in Ba/F3-ICOS cells treated with H2L5 hIgG4PE—Intracellular signalling antibody array.

FIG. 16: H2L5 hIgG4PE in combination with ipilimumab results increased proinflammatory cytokine production as compared to single antibody treatment in PBMC pre-stimulation assay.

FIG. 17: H2L5 hIgG4PE in combination with pembrolizumab results increased proinflammatory cytokine production as compared to single antibody treatment in PBMC pre-stimulation assay.

FIG. 18: H2L5 hIgG4PE plus ipilimumab combination induces increased proinflammatory cytokine production in a modified MLR assay with CEFT peptide and pre-incubation.

FIG. 19: H2L5 hIgG4PE plus pembrolizumab combination induces increased proinflammatory cytokine production in a modified MLR assay with CEFT peptide and pre-incubation.

FIG. 20A, FIG. 20B, FIG. 20C: H2L5 hIgG4PE anti-ICOS agonist mAb alone and in combination with pembrolizumab results in tumor growth inhibition in a human PBMC A2058 Melanoma mouse tumor model.

FIG. 21A and FIG. 21B: anti-ICOS murine surrogate mAb results in significant tumor growth inhibition and increased survival in combination with an anti-PD1 murine surrogate mAb in the CT26 mouse tumor model.

FIG. 22A, FIG. 22B, FIG. 22C: anti-ICOS murine surrogate mAb results in significant tumor growth inhibition and increased survival in combination with an anti-PD1 murine surrogate mAb in the EMT6 mouse tumor model.

DETAILED DESCRIPTION OF THE INVENTION

Definitions

Figure 21B:
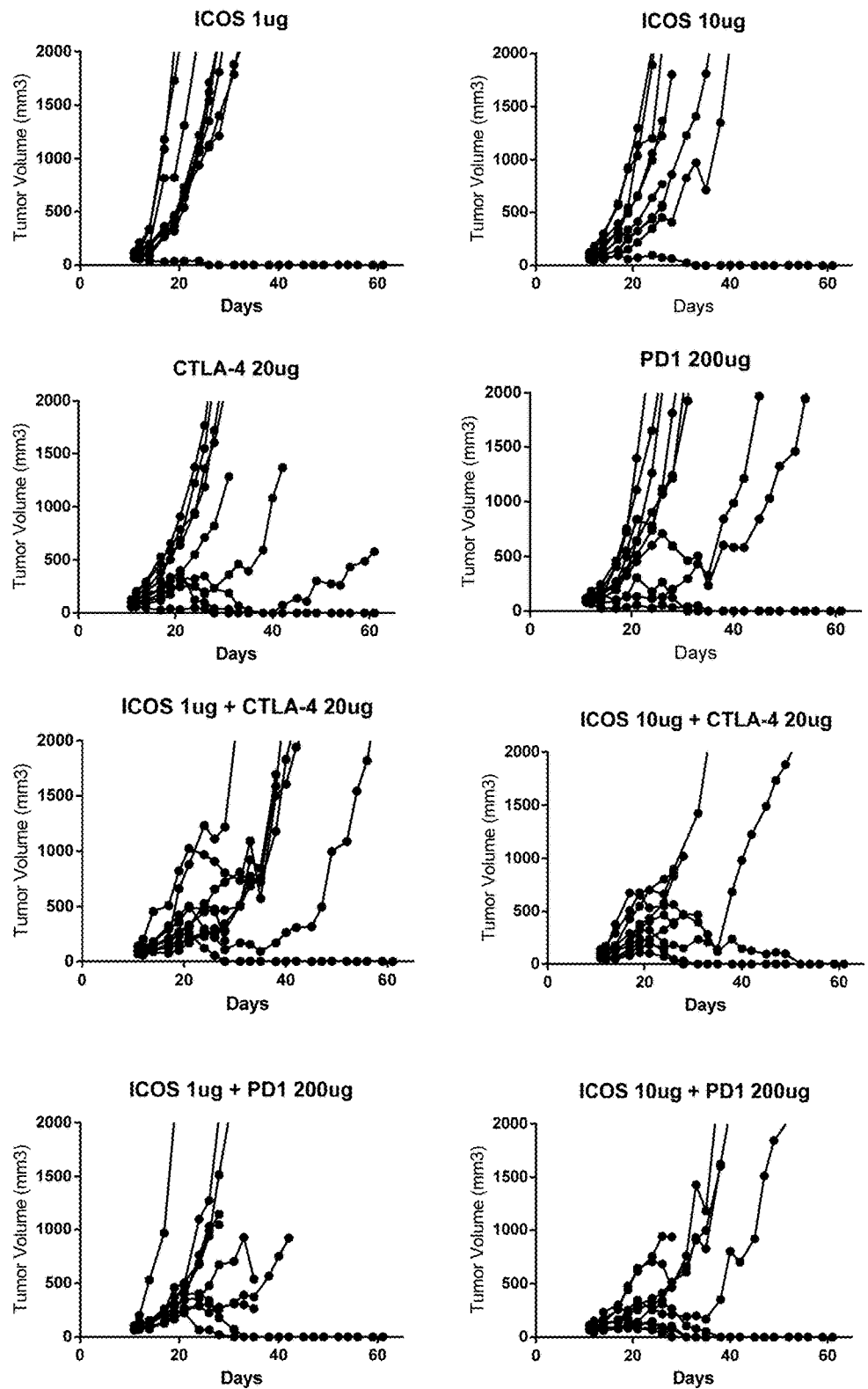

As used herein "ICOS" means any Inducible T-cell costimulator protein. Pseudonyms for ICOS (Inducible'-cell COStimulator) include AILIM; CD278; CVID1; JTT-1 or JTT-2, MGC39850, or 8F4. ICOS is a CD28-superfamily costimulatory molecule that is expressed on activated T cells. The protein encoded by this gene belongs to the CD28 and CTLA-4 cell-surface receptor family. It forms homodimers and plays an important role in cell-cell signaling, immune responses, and regulation of cell proliferation, The amino acid sequence of human ICOS is shown below as SEQ ID NO:10.

(SEQ ID NO: 10)
MKSGLWYFFLFCLRIKVLTGEINGSANYEMFIFHNGGVQILCKYPDIVQQF

KMQLLKGGQILCDLTKTKGSGNTVSIKSLKFCHSQLSNNSVSFFLYNLDHS

HANYYFCNLSIFDPPPFKVTLTGGYLHIYESQLCCQLKFWLPIGCAAFVVV

CILGCILICWLTKKM

As used herein "ICOS-L" and "ICOS Ligand" are used interchangeably and refer to the membrane bound natural ligand of human ICOS. ICOS ligand is a protein that in humans is encoded by the ICOSLG gene. ICOSLG has also been designated as CD275 (cluster of differentiation 275). Pseudonyms for ICOS-L include B7RP-1 and B7-H2.

As used herein the term "agonist" refers to an antigen binding protein, for example an ICOS binding protein, which upon contact with ICOS causes one or more of the following (1) stimulates or activates the ICOS receptor, (2) enhances, increases or promotes, induces or prolongs an activity, function or presence of ICOS and/or (3) enhances, increases, promotes or induces the expression of the ICOS. Agonist activity can be measured in vitro by various assays know in the art such as, but not limited to, measurement of cell signaling, cell proliferation, immune cell activation markers, cytokine production. Agonist activity can also be measured in vivo by various assays that measure surrogate end points such as, but not limited to the measurement of T cell proliferation or cytokine production.

As used herein the term "cross competes for binding" refers to any ICOS binding protein that will compete for binding to ICOS with any of the ICOS binding proteins of the present invention. Competition for binding between two molecules for ICOS can be tested by various methods known in the art including Flow cytometry, Meso Scale Discovery and ELISA. Binding can be measured directly, meaning two or more binding proteins can be put in contact with ICOS and binding may be measured for one or each. Alternatively, binding of molecules or interest can be tested against the binding or natural ligand and quantitatively compared with each other.

The term "ICOS binding protein" as used herein refers to antibodies and other protein constructs, such as domains, which are capable of binding to ICOS. In some instances, the ICOS is human ICOS. The term "ICOS binding protein" can be used interchangeably with "ICOS antigen binding protein." Thus, as is understood in the art, anti-ICOS antibodies and/or ICOS antigen binding proteins would be considered ICOS binding proteins. As used herein, "antigen binding protein" is any protein, including but not limited to antibodies, domains and other constructs described herein, that binds to an antigen, such as ICOS. As used herein "antigen binding portion" of an ICOS binding protein would include any portion of the ICOS binding protein capable of binding to ICOS, including but not limited to, an antigen binding antibody fragment.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanized, multispecific antibodies, including bispecific antibodies, and heteroconjugate antibodies; a single variable domain (e.g., $V_H$, $V_{HH}$, $V_L$, domain antibody (dAb™)), antigen binding antibody fragments, Fab, F(ab')$_2$, Fv, disulphide linked Fv, single chain Fv, disulphide-linked scFv, diabodies, TANDABS™, etc. and modified versions of any of the foregoing.

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer or an EGF domain.

The term "domain" refers to a folded protein structure which retains its tertiary structure independent of the rest of the protein. Generally domains are responsible for discrete functional properties of proteins and in many cases may be added, removed or transferred to other proteins without loss of function of the remainder of the protein and/or of the domain.

The term "single variable domain" refers to a folded polypeptide domain comprising sequences characteristic of antibody variable domains. It therefore includes complete antibody variable domains such as $V_H$, $V_{HH}$ and $V_L$ and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "dAb™" may be considered the same as a "single variable domain". A single variable domain may be a human single variable domain, but also includes single variable domains from other species such as rodent nurse shark and Camelid $V_{HH}$ dAbs™. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "single variable domains". As used herein $V_H$ includes camelid $V_H$ domains.

An antigen binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

The protein scaffold may be an Ig scaffold, for example an IgG, or IgA scaffold. The IgG scaffold may comprise some or all the domains of an antibody (i.e. CH1, CH2, CH3, $V_H$, $V_L$). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin kunitz type domains of human protease inhibitors; and fibronectin/adnectin; which has been subjected to protein engineering in order to obtain binding to an antigen, such as ICOS, other than the natural ligand.

Antigen binding site refers to a site on an antigen binding protein which is capable of specifically binding to an antigen, this may be a single variable domain, or it may be paired $V_H/V_L$ domains as can be found on a standard antibody. Single-chain Fv (ScFv) domains can also provide antigen-binding sites. The term "epitope-binding domain" refers to a domain that specifically binds to a region of an antigen known as the epitope independently of a different domain.

The term multi-specific antigen binding protein refers to antigen binding proteins which comprise at least two different antigen binding sites. Each of these antigen-binding sites will be capable of binding to a different epitope, which may be present on the same antigen or different antigens. The multi-specific antigen binding protein will have specificity for more than one antigen, for example two antigens, or for three antigens, or for four antigens.

Examples of multi-specific antigen binding proteins include those that consist of, or consist essentially of, an Fc region of an antibody, or a part thereof, linked at each end, directly or indirectly (for example, via a linker sequence) to a binding domain. Such an antigen binding protein may comprise two binding domains separated by an Fc region, or part thereof. By separated is meant that the binding domains are not directly linked to one another, and may be located at opposite ends (C and N terminus) of an Fc region, or any other scaffold region.

The antigen binding protein may comprise two scaffold regions each bound to two binding domains, for example at the N and C termini of each scaffold region, either directly or indirectly via a linker. Each binding domain may bind to a different antigen.

As used herein, the term mAbdAb refers to a monoclonal antibody linked to a further binding domain, in particular a single variable domain such as a domain antibody. A mAbdAb has at least two antigen binding sites, at least one of which is from a domain antibody, and at least one is from a paired $V_H$/VL domain.

A "dAb™ conjugate" refers to a composition comprising a dAb to which a drug is chemically conjugated by means of a covalent or noncovalent linkage. Preferably, the dAb and the drug are covalently bonded. Such covalent linkage could be through a peptide bond or other means such as via a modified side chain. The noncovalent bonding may be direct (e.g., electrostatic interaction, hydrophobic interaction) or indirect (e.g., through noncovalent binding of complementary binding partners (e.g., biotin and avidin), wherein one partner is covalently bonded to drug and the complementary binding partner is covalently bonded to the dAb™). When complementary binding partners are employed, one of the binding partners can be covalently bonded to the drug directly or through a suitable linker moiety, and the complementary binding partner can be covalently bonded to the dAb™ directly or through a suitable linker moiety.

As used herein, "dAb™ fusion" refers to a fusion protein that comprises a dAb™ and a polypeptide drug (which could be a dAb™ or mAb). The dAb™ and the polypeptide drug are present as discrete parts (moieties) of a single continuous polypeptide chain.

In one embodiment, antigen binding proteins of the present disclosure show cross-reactivity between human ICOS and ICOS from another species, such as cynomolgus ICOS. In an embodiment, the antigen binding proteins of the invention specifically bind human and cynomolgus ICOS. The provision of a drug that can bind human and monkey species allows one to test results in these system and make side-by-side comparisons of data using the same drug. Cross reactivity between other species used in disease models such as dog or monkey, in particular monkey, is envisaged.

Competition between an ICOS binding protein and a reference ICOS binding protein may be determined by competition MSD, ELISA, FMAT or BIAcore. In one embodiment, the competition assay is carried out by comparison of an ICOS binding protein with ICOS ligand binding. There are several possible reasons for this competition: the two proteins may bind to the same or overlapping epitopes, there may be steric inhibition of binding, or binding of the first protein may induce a conformational change in the antigen that prevents or reduces binding of the second protein.

The term "neutralizes" as used throughout the present specification means that the interaction between ICOS and ICOS-L is reduced in the presence of an antigen binding protein as described herein in comparison to the interaction of ICOS and ICOS-L in the absence of the ICOS binding protein, in vitro or in vivo. Neutralization may be due to one or more of blocking ICOS binding to its ligand, preventing ICOS from being activated by its ligand, down regulating ICOS or its receptor, or affecting effector functionality. For example, the ligand binding competition described in Examples 3 and 5 may be used to assess the neutralizing capability of an ICOS binding protein.

The effect of an ICOS binding protein on the interaction between ICOS and ICOS-L may be partial or total. A neutralising ICOS binding protein may block the interaction of ICOS with ICOS-L by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to ICOS-ICOS-L interactions in the absence of the ICOS binding protein.

Neutralization may be determined or measured using one or more assays known to the skilled person or as described herein.

Affinity is the strength of binding of one molecule, e.g. an antigen binding protein of the invention, to another, e.g. its target antigen, at a single binding site. The binding affinity of an antigen binding protein to its target may be determined by equilibrium methods (e.g. enzyme-linked immunoabsorbent assay (ELISA) or radioimmunoassay (RIA)), or kinetics (e.g. BIACORE™ analysis). For example, the Biacore™ methods described in Example 5 may be used to measure binding affinity.

Avidity is the sum total of the strength of binding of two molecules to one another at multiple sites, e.g. taking into account the valency of the interaction.

In an embodiment, the equilibrium dissociation constant (KD) of the ICOS binding protein-ICOS interaction is 100 nM or less, 10 nM or less, 2 nM or less or 1 nM or less. Alternatively the KD may be between 5 and 10 nM; or between 1 and 2 nM. The KD may be between 1 pM and 500 pM; or between 500 pM and 1 nM. A skilled person will appreciate that the smaller the KD numerical value, the stronger the binding. The reciprocal of KD (i.e. 1/KD) is the equilibrium association constant (KA) having units $M^{-1}$. A skilled person will appreciate that the larger the KA numerical value, the stronger the binding.

The dissociation rate constant (kd) or "off-rate" describes the stability of the ICOS binding protein ICOS complex, i.e. the fraction of complexes that decay per second. For example, a kd of 0.01 $s^{-1}$ equates to 1% of the complexes decaying per second. In an embodiment, the dissociation rate constant (kd) is $1\times10's^{-1}$ or less, $1\times10^{-4}$ $s^{-1}$ or less, $1\times10^{-5}$ $s^{-1}$ or less, or $1\times10^{-6}$ $s^{-1}$ or less. The kd may be between $1\times10^{-5}s^{-1}$ and $1\times10^{-4}$ $s^{-1}$; or between $1\times10^{-4}$ $s^{-1}$ and $1\times10's^{-1}$.

The association rate constant (ka) or "on-rate" describes the rate of ICOS binding protein-ICOS complex formation. In an embodiment, the association rate constant (ka) is about $1.0\times10^5$ $M^{-1}s^{-1}$.

By "isolated" it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass.

The term "expression vector" as used herein means an isolated nucleic acid which can be used to introduce a nucleic acid of interest into a cell, such as a eukaryotic cell or prokaryotic cell, or a cell free expression system where the nucleic acid sequence of interest is expressed as a peptide chain such as a protein. Such expression vectors may be, for example, cosmids, plasmids, viral sequences, transposons, and linear nucleic acids comprising a nucleic acid of interest. Once the expression vector is introduced into a cell or cell free expression system (e.g., reticulocyte lysate) the protein encoded by the nucleic acid of interest is produced by the transcription/translation machinery. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, Drosophila expression vectors, and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors. Those of ordinary skill in the art will recognize many other suitable expression vectors and expression systems.

The term "recombinant host cell" as used herein means a cell that comprises a nucleic acid sequence of interest that was isolated prior to its introduction into the cell. For example, the nucleic acid sequence of interest may be in an expression vector while the cell may be prokaryotic or eukaryotic. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells or any derivative thereof. Most preferably, the eukaryotic cell is a HEK293, NS0, SP2/0, or CHO cell. *E. coli* is an exemplary prokaryotic cell. A recombinant cell according to the disclosure may be generated by transfection, cell fusion, immortalization, or other procedures well known in the art. A nucleic acid sequence of interest, such as an expression vector, transfected into a cell may be extrachromasomal or stably integrated into the chromosome of the cell.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity (see, e.g., Queen et al. Proc. Natl Acad Sci USA, 86:10029-10032 (1989), Hodgson, et al., *Bio/Technology*, 9:421 (1991)). A suitable human acceptor antibody may be one selected from a conventional database, e.g., the KABAT™ database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see, for example, EP-A-0239400 and EP-A-054951.

The term "fully human antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). Fully human antibodies comprise amino acid sequences encoded only by polynucleotides that are ultimately of human origin or amino acid sequences that are identical to such sequences. As meant herein, antibodies encoded by human immunoglobulin-encoding DNA inserted into a mouse genome produced in a transgenic mouse are fully human antibodies since they are encoded by DNA that is ultimately of human origin. In this situation, human immunoglobulin-encoding DNA can be rearranged (to encode an antibody) within the mouse, and somatic mutations may also occur. Antibodies encoded by originally human DNA that has undergone such changes in a mouse are fully human antibodies as meant herein. The use of such transgenic mice makes it possible to select fully human antibodies against a human antigen. As is understood in the art, fully human antibodies can be made using phage display technology wherein a human DNA library is inserted in phage for generation of antibodies comprising human germline DNA sequence.

The term "donor antibody" refers to an antibody that contributes the amino acid sequences of its variable regions, CDRs, or other functional fragments or analogs thereof to a first immunoglobulin partner. The donor, therefore, provides the altered immunoglobulin coding region and resulting expressed altered antibody with the antigenic specificity and neutralising activity characteristic of the donor antibody.

The term "acceptor antibody" refers to an antibody that is heterologous to the donor antibody, which contributes all (or any portion) of the amino acid sequences encoding its heavy and/or light chain framework regions and/or its heavy and/or light chain constant regions to the first immunoglobulin partner. A human antibody may be the acceptor antibody.

The terms "V$_H$" and "V$_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 5th Ed., U.S. Department of Health and Human Services, National Institutes of Health (1991).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

|    | Kabat CDR | Chothia CDR | AbM CDR | Contact CDR | Minimum binding unit |
|----|-----------|-------------|---------|-------------|----------------------|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Accordingly, ICOS binding proteins are provided, which comprises any one or a combination of the following CDRs:

```
CDRH1:    DYAMH (SEQ ID NO: 1)
CDRH2:    LISIYSDHTNYNQKFQG (SEQ ID NO: 2)
CDRH3:    NNYGNYGWYFDV (SEQ ID NO: 3)
CDRL1:    SASSSVSYMH (SEQ ID NO: 4)
CDRL2:    DTSKLAS (SEQ ID NO: 5)
CDRL3:    FQGSGYPYT (SEQ ID NO: 6)
```

In one embodiment of the present invention the ICOS binding protein comprises CDRH1 (SEQ ID NO:1), CDRH2 (SEQ ID NO:2), and CDRH3 (SEQ ID NO:3) in the heavy chain variable region having the amino acid sequence set forth in SEQ ID NO:7. ICOS binding proteins of the present invention comprising the humanized heavy chain variable region set forth in SEQ ID NO:7 are designated as "H2." In some embodiments, the ICOS binding proteins of the present invention comprise a heavy chain variable region having at least 90% sequence identity to SEQ ID NO:7. Suitably, the ICOS binding proteins of the present invention may comprise a heavy chain variable region having about 85%, 86%, 87%, 88%, 89%, 90%, 91%, 92%, 93%, 94%, 95%, 96%, 97%, 98%, 99%, or 100% sequence identity to SEQ ID NO:7.

Humanized Heavy Chain (V$_H$) Variable Region (H2):

(SEQ ID NO:7)
QVQLVQSGAEVKKPGSSVKVSCKASGYTFT<u>DYAMH</u>WVRQAPGQGLEWMG<u>LI
SIYSDHTNYNQKFQG</u>RVTITADKSTSTAYMELSSLRSEDTAVYYCGR<u>NNYG
NYGWYFDV</u>WGQGTTVTVSS

In one embodiment of the present invention the ICOS binding protein comprises CDRL1 (SEQ ID NO:4), CDRL2 (SEQ ID NO:5), and CDRL3 (SEQ ID NO:6) in the light chain variable region having the amino acid sequence set forth in SEQ ID NO:8. ICOS binding proteins of the present invention comprising the humanized light chain variable region set forth in SEQ ID NO:8 are designated as "L5." Thus, an ICOS binding protein of the present invention comprising the heavy chain variable region of SEQ ID NO:7 and the light chain variable region of SEQ ID NO:8 can be designated as H2L5 herein.

Suitably a leader sequence for the variable heavy chain and light chain constructs is show in FIG. 9 and includes, but is not limited to: MGWSCIILFLVATATGVHS (SEQ ID NO:11)

In some embodiments, the ICOS binding proteins of the present invention comprise a light chain variable region having at least 90% sequence identity to the amino acid sequence set forth in SEQ ID NO:8. Suitably, the ICOS binding proteins of the present invention may comprise a light chain variable region having about 85%, 86%, 87%, 88%, 89%, 90%, 91%, 92%, 93%, 94%, 95%, 96%, 97%, 98%, 99%, or 100% sequence identity to SEQ ID NO:8.

Humanized Light Chain (V$_L$) Variable Region (L5)

(SEQ ID NO:8)
EIVLTQSPATLSLSPGERATLSC<u>SASSSVSYMH</u>WYQQKPGQAPRLLIY<u>DTS
KLAS</u>GIPARFSGSGSGTDYTLTISSLEPEDFAVYYC<u>FQGSGYPYT</u>FGQGTK
LEIK

CDRs or minimum binding units may be modified by at least one amino acid substitution, deletion or addition, wherein the variant antigen binding protein substantially retains the biological characteristics of the unmodified protein, such as a murine antibody produced from clone 422.2 or an antibody comprising SEQ ID NO:7 and SEQ ID NO:8.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in Table 2 below.

TABLE 2

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the amino acid residues of the minimum binding unit may remain the same, but the flanking residues that comprise the CDR as part of the Kabat or Chothia definition(s) may be substituted with a conservative amino acid residue.

Such antigen binding proteins comprising modified CDRs or minimum binding units as described above may be referred to herein as "functional CDR variants" or "functional binding unit variants". Suitably, in one embodiment ICOS binding proteins are provided comprising one or more CDRs having the amino acid sequences set forth in SEQ ID NOs:1, 2, 3, 4, 5, and/or 6 and/or a function CDR variant thereof.

The term "epitope" as used herein refers to that portion of the antigen that makes contact with a particular binding domain of the antigen binding protein. An epitope may be linear or conformational/discontinuous. A conformational or discontinuous epitope comprises amino acid residues that are separated by other sequences, i.e. not in a continuous sequence in the antigen's primary sequence. Although the residues may be from different regions of the peptide chain, they are in close proximity in the three dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography.

The CDRs L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

There may be multiple variant CDR canonical positions per CDR, per corresponding CDR, per binding unit, per heavy or light chain variable region, per heavy or light chain, and per antigen binding protein, and therefore any combination of substitution may be present in the antigen binding protein of the invention, provided that the canonical structure of the CDR is maintained such that the antigen binding protein is capable of specifically binding ICOS.

As discussed above, the particular canonical structure class of a CDR is defined by both the length of the CDR and by the loop packing, determined by residues located at key positions in both the CDRs and the framework regions.

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

The % identity may be determined across the entire length of the query sequence, including the CDR(s). Alternatively, the % identity may exclude the CDR(s), for example the CDR(s) is 100% identical to the subject sequence and the % identity variation is in the remaining portion of the query sequence, so that the CDR sequence is fixed/intact.

The variant sequence substantially retains the biological characteristics of the unmodified protein, such as SEQ ID NO:7 or SEQ ID NO:8.

The $V_H$ or $V_L$ sequence may be a variant sequence with up to 15 amino acid substitutions, additions or deletions. For example, the variant sequence may have up to 15, 14, 13, 12, 11, 10, 9, 8, 7, 6, 5, 4, 3, 2 or 1 amino acid substitution(s), addition(s) or deletion(s).

The sequence variation may exclude the CDR(s), for example the CDR(s) is the same as the $V_H$ or $V_L$ (or HC or LC) sequence and the variation is in the remaining portion of the $V_H$ or $V_L$ (or HC or LC) sequence, so that the CDR sequence is fixed/intact.

The skilled person will appreciate that, upon production of an antigen binding protein such as an antibody, in particular depending on the cell line used and particular amino acid sequence of the antigen binding protein, post-translational modifications may occur. For example, this may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of antigen binding proteins which have been subjected to, or have undergone, one or more post-translational modifications. Thus an "antigen binding protein" or "antibody" of the invention includes an "antigen binding protein" or "antibody", respectively, as defined earlier which has undergone a post-translational modification such as described herein.

Deamidation is an enzymatic reaction primarily converting asparagine (N) to isoaspartic acid and aspartic acid (D) at approximately 3:1 ratio. To a much lesser degree, deamidation can occur with glutamine residues in a similar manner. Deamidation in a CDR results in a change in charge of the molecule, but typically does not result in a change in antigen binding, nor does it impact on PK/PD.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but occasionally can occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

Isomerization typically occurs during production, purification, and storage (at acidic pH) and usually occurs when aspartic acid is converted to isoaspartic acid through a chemical process.

N-terminal glutamine in the heavy chain and/or light chain is likely to form pyroglutamate (pGlu). Most pGlu formation happens in the production bioreactor, but it can be formed non-enzymatically, depending on pH and temperature of processing and storage conditions. pGlu formation is considered as one of the principal degradation pathways for recombinant mAbs.

C-terminal lysine clipping is an enzymatic reaction catalyzed by carboxypeptidases, and is commonly observed in recombinant mAbs. Variants of this process include removal of lysine from one or both heavy chains. Lysine clipping does not appear to impact bioactivity and has no effect on mAb effector function.

Naturally occurring autoantibodies exist in humans that can bind to proteins. Autoantibodies can thus bind to endogenous proteins (present in naïve subjects) as well as to proteins or peptides which are administered to a subject for treatment. Therapeutic protein-binding autoantibodies and antibodies that are newly formed in response to drug treatment are collectively termed anti-drug antibodies (ADAs). Pre-existing antibodies against molecules such as therapeutic proteins and peptides, administered to a subject can affect their efficacy and could result in administration reactions, hypersensitivity, altered clinical response in treated patients and altered bioavailability by sustaining, eliminating or neutralizing the molecule. It could be advantageous to provide molecules for therapy which comprise human immunoglobulin (antibody) single variable domains or dAbs™ which have reduced immunogenicity (i.e. reduced ability to bind to pre-existing ADAs when administered to a subject, in particular a human subject.

Thus, in one embodiment of the present invention there is provided a modified dAb™ which has reduced ability to bind to pre-existing antibodies (ADAs) as compared to the equivalent unmodified molecule. By reduced ability to bind it is meant that the modified molecule binds with a reduced affinity or reduced avidity to a pre-existing ADA. Said modified dAb™ comprise one or more modifications selected from: (a) a C-terminal addition, extension, deletion or tag, and/or (b) one or more amino acid framework substitutions.

Polypeptides and dAbs™ of the disclosure and agonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides dAbs™ and agonists may be formatted as a larger antigen-binding fragment of an antibody or as an antibody (e.g., formatted as a Fab, Fab', F(ab)$_2$, F(ab')2, IgG, scFv).

As used herein, "hydrodynamic size" refers to the apparent size of a molecule (e.g., an antigen binding protein) based on the diffusion of the molecule through an aqueous solution. The diffusion or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation and charge of the protein. An increase in hydrodynamic size can give an associated decrease in renal clearance leading to an observed increase in half life ($t_{1/2}$).

Hydrodynamic size of the antigen binding proteins (e.g., domain antibody monomers and multimers) of the disclosure may be determined using methods which are well known in the art. For example, gel filtration chromatography may be used to determine the hydrodynamic size of an antigen binding protein. Suitable gel filtration matrices for determining the hydrodynamic sizes of antigen binding proteins, such as cross-linked agarose matrices, are well known and readily available.

The size of an antigen binding protein format (e.g., the size of a PEG moiety attached to a domain antibody monomer), can be varied depending on the desired application. For example, where antigen binding protein is intended to leave the circulation and enter into peripheral tissues, it is desirable to keep the hydrodynamic size of the ICOS binding protein low to facilitate extravazation from the blood stream. Alternatively, where it is desired to have the antigen binding protein remain in the systemic circulation for a longer period of time the size of the antigen binding protein can be increased, for example by formatting as an Ig like protein.

Pharmaceutical Compositions

Antigen binding protein as described herein may be incorporated into pharmaceutical compositions for use in the treatment of the human diseases described herein. In one embodiment, the pharmaceutical composition comprises an antigen binding protein optionally in combination with one or more pharmaceutically acceptable carriers and/or excipients.

Such compositions comprise a pharmaceutically acceptable carrier as known and called for by acceptable pharmaceutical practice.

Pharmaceutical compositions may be administered by injection or continuous infusion (examples include, but are not limited to, intravenous, intraperitoneal, intradermal, subcutaneous, intramuscular and intraportal). In one embodiment, the composition is suitable for intravenous administration. Pharmaceutical compositions may be suitable for topical administration (which includes, but is not limited to, epicutaneous, inhaled, intranasal or ocular administration) or enteral administration (which includes, but is not limited to, oral or rectal administration).

Pharmaceutical compositions may comprise between 0.5 mg to 10 g of ICOS binding protein, for example between 5 mg and 1 g of antigen binding protein. Alternatively, the composition may comprise between 5 mg and 500 mg, for example between 5 mg and 50 mg. Methods for the preparation of such pharmaceutical compositions are well known to those skilled in the art. Other excipients may be added to the composition as appropriate for the mode of administration and the particular protein used. Examples of different excipients and their uses are described in Lowe et al., (2011).

Effective doses and treatment regimes for administering the antigen binding protein may be dependent on factors such as the age, weight and health status of the patient and disease to be treated. Such factors are within the purview of the attending physician. Guidance in selecting appropriate doses may be found in e.g Bai et al., (2012).

The pharmaceutical composition may comprise a kit of parts of the antigen binding protein together with other medicaments, optionally with instructions for use. For convenience, the kit may comprise the reagents in predetermined amounts with instructions for use.

The terms "individual", "subject" and "patient" are used herein interchangeably. In one embodiment, the subject is a mammal, such as a primate, for example a marmoset or monkey. In another embodiment, the subject is a human.

The antigen binding protein described herein may also be used in methods of treatment. Treatment can be therapeutic, prophylactic or preventative. Treatment encompasses alleviation, reduction, or prevention of at least one aspect or symptom of a disease and encompasses prevention or cure of the diseases described herein.

The ICOS binding protein or antigen binding portion thereof described herein is used in an effective amount for therapeutic, prophylactic or preventative treatment. A therapeutically effective amount of the ICOS binding protein or antigen binding portion thereof described herein is an amount effective to ameliorate or reduce one or more symptoms of, or to prevent or cure, the disease.

Thus, in one embodiment ICOS binding proteins or antigen binding portions thereof of the present invention are provided for use in therapy. In one embodiment, ICOS binding proteins or antigen binding portions thereof of the present invention are provided for use in the treatment of cancer, infectious disease and/or sepsis. The present invention also provides the use of an ICOS binding protein or antigen binding portion thereof of the present invention in the manufacture of a medicament for the treatment of cancer, infectious disease and/or sepsis.

Thus, provided herein are isolated ICOS binding proteins or antigen binding portions thereof or the pharmaceutical compositions comprising said isolated ICOS binding proteins or antigen binding portions thereof for use in the treatment of cancer, infectious disease and/or sepsis.

Production Methods

Antigen binding proteins may be prepared by any of a number of conventional techniques. For example, antigen binding proteins may purified from cells that naturally express them (e.g., an antibody can be purified from a hybridoma that produces it), or produced in recombinant expression systems.

A number of different expression systems and purification regimes can be used to generate the antigen binding protein of the invention. Generally, host cells are transformed with a recombinant expression vector encoding the desired antigen binding protein. A wide range of host cells can be employed, including Prokaryotes (including Gram negative or Gram positive bacteria, for example *Escherichia coli*, Bacilli sp., *Pseudomonas* sp., *Corynebacterium* sp.), Eukaryotes including yeast (for example *Saccharomyces cerevisiae, Pichia pastoris*), fungi (for example *Aspergillus* sp.), or higher Eukaryotes including insect cells and cell lines of mammalian origin (for example, CHO, Perc6, HEK293, HeLa).

The host cell may be an isolated host cell. The host cell is usually not part of a multicellular organism (e.g., plant or animal). The host cell may be a non-human host cell.

Appropriate cloning and expression vectors for use with bacterial, fungal, yeast, and mammalian cellular hosts and methods of cloning are known in the art.

The cells can be cultured under conditions that promote expression of the antigen binding protein, and the polypeptide recovered by conventional protein purification procedures. The antigen binding proteins contemplated for use herein include substantially homogeneous antigen binding proteins substantially free of contaminating materials.

The skilled person will appreciate that, upon production of the antigen binding protein, in particular depending on the cell line used and particular amino acid sequence of the antigen binding protein, post-translational modifications may occur. This may include the cleavage of certain leader sequences, the addition of various sugar moieties in various glycosylation patterns, deamidation (for example at an asparagine or glutamine residue), oxidation (for example at a methionine, tryptophan or free cysteine residue), disulfide bond scrambling, isomerisation (for example at an aspartic acid residue), C-terminal lysine clipping (for example from one or both heavy chains), and N-terminal glutamine cyclisation (for example in the heavy and/or light chain). The present invention encompasses the use of antibodies which have been subjected to, or have undergone, one or more post-translational modifications. The modification may occur in a CDR, the variable framework region, or the constant region. The modification may result in a change in charge of the molecule. The modification typically does not result in a change in antigen binding, function, bioactivity, nor does it impact the pharmacokinetic (PK) or pharmacodynamic (PD) characteristics of the ICOS binding protein.

The term "Effector Function" as used herein is meant to refer to one or more of Antibody dependant cell mediated cytotoxic activity (ADCC), Complement-dependant cytotoxic activity (CDC) mediated responses, Fc-mediated phagocytosis or antibody dependant cellular phagocytosis (ADCP) and antibody recycling via the FcRn receptor.

The interaction between the constant region of an antigen binding protein and various Fc receptors (FcR) including FcγRI (CD64), FcγRII (CD32) and FcγRIII (CD16) is believed to mediate the effector functions of the antigen binding protein. Significant biological effects can be a consequence of effector functionality. Usually, the ability to mediate effector function requires binding of the antigen binding protein to an antigen and not all antigen binding proteins will mediate every effector function.

Effector function can be measured in a number of ways including for example via binding of the FcγRIII on Natural Killer cells or via FcγRI on monocytes/macrophages to measure for ADCC/ADCP effector function. For example an antigen binding protein of the present invention can be assessed for ADCC effector function in a Natural Killer cell assay. Practical approaches to evaluate ADCC and/or CDC function can be found in (Kellner C et al., "Boosting ADCC and CDC activity by Fc engineering and evaluation of antibody effector functions", Methods, 1; 65(1):105-13 (2014))

Some isotypes of human constant regions, in particular IgG4 and IgG2 isotypes, have reduced function of a) activation of complement by the classical pathway; and b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC. (Kellner C et al., "Boosting ADCC and CDC activity by Fc engineering and evaluation of antibody effector functions", Methods, 1; 65(1):105-13 (2014))

In one embodiment of the present invention there is provided an antigen binding protein comprising a constant region such that the antigen binding protein has reduced ADCC and/or complement activation or effector functionality. In one such embodiment the heavy chain constant region may comprise a naturally disabled constant region of IgG2 or IgG4 isotype or a mutated IgG1 constant region. One example comprises the substitutions of alanine residues at positions 235 and 237 (EU index numbering).

The subclass of an antibody in part determines secondary effector functions, such as complement activation or Fc receptor (FcR) binding and antibody dependent cell cytotoxicity (ADCC) (Huber, et al., Nature 229(5284): 419-20 (1971); Brunhouse, et al., Mol Immunol 16(11): 907-17 (1979)). In identifying the optimal type of antibody for a particular application, the effector functions of the antibodies can be taken into account. For example, hIgG1 antibodies have a relatively long half life, are very effective at fixing complement, and they bind to both FcγRI and FcγRII. In contrast, human IgG4 antibodies have a shorter half life, do not fix complement and have a lower affinity for the FcRs. Replacement of serine 228 with a proline (S228P) in the Fc region of IgG4 reduces heterogeneity observed with hIgG4 and extends the serum half life (Kabat, et al., "Sequences of proteins of immunological interest" 5.sup.th Edition (1991); Angal, et al., Mol Immunol 30(1): 105-8 (1993)). A second mutation that replaces leucine 235 with a glutamic acid (L235E) eliminates the residual FcR binding and complement binding activities (Alegre, et al., J Immunol 148(11): 3461-8 (1992)). The resulting antibody with both mutations is referred to as IgG4PE. The numbering of the hIgG4 amino acids was derived from EU numbering reference: Edelman, G. M. et al., Proc. Natl. Acad. USA, 63, 78-85 (1969). PMID: 5257969. In one embodiment of the present invention ICOS antigen binding proteins comprising an IgG4 Fc region comprising the replacement S228P and L235E may have the designation IgG4PE. Thus, an ICOS binding protein having the heavy chain variable region H2 and the light chain variable region L5 and an IgG4PE Fc region will be designated as H2L5 IgG4PE or synonymously as H2L5 hIgG4PE.

Enhanced ADCC/CDC

As is understood in the art various techniques are known which will increase the ADCC and/or the CDC activity of an antibody. These include, but are not limited to, various mutation in the Fc region, Complegent and Potelligent technologies. In one aspect of the present invention one or more ADCC/CDC enhancing techniques may be applied to the ICOS binding proteins of the present invention.

Mutation

Human IgG1 constant regions containing specific mutations or altered glycosylation on residue Asn297 have also been described to enhance binding to Fc receptors. In some cases these mutations have also been shown to enhance ADCC and CDC, see for example, Kellner (2013).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment the antigen binding protein of the invention herein described is mutated at positions 239 and 332, for example S239D and I332E or in a further embodiment it is mutated at three or more positions selected from 239 and 332 and 330, for example S239D and I332E and A330L (EU index numbering).

Complegent

In one embodiment of the present invention there is provided an antigen binding protein comprising a chimeric heavy chain constant region for example an antigen binding protein comprising a chimeric heavy chain constant region with at least one CH2 domain from IgG3 such that the antigen binding protein has enhanced effector function, for example wherein it has enhanced ADCC or enhanced CDC, or enhanced ADCC and CDC functions. In one such embodiment, the antigen binding protein may comprise one CH2 domain from IgG3 or both CH2 domains may be from IgG3.

Also provided is a method of producing an antigen binding protein according to the invention comprising the steps of:

a) culturing a recombinant host cell comprising an expression vector comprising an isolated nucleic acid as described herein wherein the expression vector comprises a nucleic acid sequence encoding an Fc domain having both IgG1 and IgG3 Fc domain amino acid residues; and b) recovering the antigen binding protein.

Such methods for the production of antigen binding proteins can be performed, for example, using the COMPLEGENT™ technology system available from BioWa, Inc. (Princeton, N.J.) and Kyowa Hakko Kogyo (now, Kyowa Hakko Kirin Co., Ltd.) Co., Ltd. In which a recombinant host cell comprising an expression vector in which a nucleic acid sequence encoding a chimeric Fc domain having both IgG1 and IgG3 Fc domain amino acid residues is expressed to produce an antigen binding protein having enhanced complement dependent cytotoxicity (CDC) activity that is increased relative to an otherwise identical antigen binding protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

Potelligent

The present invention also provides a method for the production of an antigen binding protein according to the invention comprising the steps of:

a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein.

Such methods for the production of antigen binding proteins can be performed, for example, using the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. No. 7,214,775, U.S. Pat. No. 6,946,292, WO0061739 and WO0231240 all of which are incorporated herein by reference. Those of ordinary skill in the art will also recognize other appropriate systems.

It will be apparent to those skilled in the art that such modifications may not only be used alone but may be used in combination with each other in order to further enhance effector function.

In one such embodiment of the present invention there is provided an antigen binding protein comprising a heavy chain constant region which comprises a mutated and chimaeric heavy chain constant region for example wherein an antigen binding protein comprising at least one CH2 domain from IgG3 and one CH2 domain from IgG1, wherein the IgG1 CH2 domain has one or more mutations at positions selected from 239 and 332 and 330 (for example the mutations may be selected from S239D and I332E and A330L) such that the antigen binding protein has enhanced effector function, for example wherein it has one or more of the following functions, enhanced ADCC or enhanced CDC, for example wherein it has enhanced ADCC and enhanced CDC. In one embodiment the IgG1 CH2 domain has the mutations S239D and I332E.

In an alternative embodiment of the present invention there is provided an antigen binding protein comprising a chimaeric heavy chain constant region and which has an altered glycosylation profile. In one such embodiment the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC In an alternative embodiment the antigen binding protein has at least one IgG3 CH2 domain and at least one heavy chain constant domain from IgG1 wherein both IgG CH2 domains are mutated in accordance with the limitations described herein.

In one aspect of the invention there is provided a method of producing an antigen binding protein according to the invention described herein comprising the steps of:

a) culturing a recombinant host cell containing an expression vector containing an isolated nucleic acid as described herein, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and b) recovering the antigen binding protein.

Such methods for the production of antigen binding proteins can be performed, for example, using the ACCRETAMAB™ technology system available from BioWa, Inc. (Princeton, N.J.) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide In yet another embodiment of the present invention there is provided an antigen binding protein comprising a mutated and chimeric heavy chain constant region wherein said antigen binding protein has an altered glycosylation profile such that the antigen binding protein has enhanced effector function, for example wherein it has one or more of the following functions, enhanced ADCC or enhanced CDC. In one embodiment the mutations are selected from positions 239 and 332 and 330, for example the mutations are selected from S239D and I332E and A330L. In a further embodiment the heavy chain constant region comprises at least one CH2 domain from IgG3 and one Ch2 domain from IgG1. In one embodiment the heavy chain constant region has an altered glycosylation profile such that the ratio of fucose to mannose is 0.8:3 or less for example the antigen binding protein is defucosylated, so that said antigen binding protein has an enhanced effector function in comparison with an equivalent non-chimaeric antigen binding protein or with an immunoglobulin heavy chain constant region lacking said mutations and altered glycosylation profile.

The long half-life of IgG antibodies is reported to be dependent on its binding to FcRn. Therefore, substitutions that increase the binding affinity of IgG to FcRn at pH 6.0 while maintaining the pH dependence of the interaction by engineering the constant region have been extensively studied Kuo and Aveson (2011).

Another means of modifying antigen binding proteins of the present invention involves increasing the in-vivo half life of such proteins by modification of the immunoglobulin constant domain or FcRn (Fc receptor neonate) binding domain.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells, and if they bind to FcRn, are recycled out into circulation. In contrast, IgG molecules that do not bind to FcRn enter the cells and are targeted to the lysosomal pathway where they are degraded.

The neonatal FcRn receptor is believed to be involved in both antibody clearance and the transcytosis across tissues, Kuo and Aveson, (2011). Human IgG1 residues determined to interact directly with human FcRn includes Ile253, Ser254, Lys288, Thr307, Gln311, Asn434 and His435. Switches at any of these positions described in this section may enable increased serum half-life and/or altered effector properties of antigen binding proteins of the invention.

Mutations to Increase Half Life by Increasing Affinity to FcRn

Antigen binding proteins of the present invention may have one or more amino acid modifications that increase the affinity of the constant domain or fragment thereof for FcRn.

These may result in increased half-life of these proteins Kuo and Aveson (2011) Increasing the half-life of therapeutic and diagnostic IgG's and other bioactive molecules has many benefits including reducing the amount and/or frequency of dosing of these molecules. In one embodiment there is therefore provided an antigen binding according to the invention provided herein or a fusion protein comprising all or a portion (an FcRn binding portion) of an IgG constant domain having one or more of these amino acid modifications and a non-IgG protein or non-protein molecule conjugated to such a modified IgG constant domain, wherein the presence of the modified IgG constant domain increases the in vivo half life of the antigen binding protein.

A number of methods are known that can result in increased half-life (Kuo and Aveson, (2011)), including amino acid modifications may be generated through techniques including alanine scanning mutagenesis, random mutagenesis and screening to assess the binding to FcRn and/or the in vivo behaviour. Computational strategies followed by mutagenesis may also be used to select one of amino acid mutations to mutate.

The present invention therefore provides a variant of an antigen binding protein with optimized binding to FcRn. In a preferred embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat.

In a further aspect of the invention the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

pH Switch Technology to Increase Half Life

Although substitutions in the constant region are able to significantly improve the functions of therapeutic IgG antibodies, substitutions in the strictly conserved constant region have the risk of immunogenicity in human and substitution in the highly diverse variable region sequence might be less immunogenic. Reports concerned with the variable region include engineering the CDR residues to improve binding affinity to the antigen and engineering, the CDR and framework residues to improve stability and decrease immunogenicity risk. As is known, improved affinity to the antigen can be achieved by affinity maturation using the phage or ribosome display of a randomized library.

Improved stability can be rationally obtained from sequence- and structure-based rational design. Decreased immunogenicity risk (deimmunization) can be accomplished by various humanization methodologies and the removal of T-cell epitopes, which can be predicted using in silico technologies or determined by in vitro assays. Additionally, variable regions have been engineered to lower pI. A longer half life was observed for these antibodies as compared to wild type antibodies despite comparable FcRn binding. Engineering or selecting antibodies with pH dependent antigen binding to modify antibody and/or antigen half life eg IgG2 antibody half life can be shortened if antigen-mediated clearance mechanisms normally degrade the antibody when bound to the antigen. Similarly, the antigen: antibody complex can impact the half-life of the antigen, either extending half-life by protecting the antigen from the typical degradation processes, or shortening the half-life via antibody-mediated degradation. One embodiment relates to antibodies with higher affinity for antigen at pH 7.4 as compared to endosomal pH (i.e., pH 5.5-6.0) such that the KD ratio at pH5.5/pH 7.4 or at pH 6.0/pH 7.4 is 2 or more. For example to enhance the pharmacokinetic (PK) and pharmacodynamic (PD) properties of the antibody, it is possible to engineer pH-sensitive binding to the antibody by introducing histidines into CDR residues.

Additionally, methods of producing an antigen binding protein with a decreased biological half-life are also provided. A variant IgG in which His435 is mutated to alanine results in the selective loss of FcRn binding and a significantly reduced serum half-life (see for example U.S. Pat. No. 6,165,745 discloses a method of producing an antigen binding protein with a decreased biological half-life by introducing a mutation into the DNA segment encoding the antigen binding protein. The mutation includes an amino acid substitution at position 253, 310, 311, 433, or 434 of the Fc-hinge domain.

Linkers

Protein scaffolds may be the same as naturally occurring sequences, such as Ig sequences, or be fragments of naturally occurring sequences, and may contain additional sequences which may be naturally occurring, from a difference source or synthetic, and which may be added at the N or C terminus of the scaffold. Such additional sequences may be considered to be linkers when they link an epitope binding domain and protein scaffold, such as those defined herein.

In another aspect the antigen binding construct consists of, or consists essentially of, an Fc region of an antibody, or a part thereof, linked at each end, directly or indirectly (for example, via a linker sequence) to an epitope binding domain. Such an antigen binding construct may comprise 2 epitope-binding domains separated by an Fc region, or part thereof. By separated is meant that the epitope-binding domains are not directly linked to one another, and in one aspect are located at opposite ends (C and N terminus) of an Fc region, or any other scaffold region.

In one aspect the antigen binding construct comprises 2 scaffold regions each bound to 2 epitope binding domains, for example at the N and C termini of each scaffold region, either directly or indirectly via a linker.

Protein scaffolds of the present invention may be linked to epitope-binding domains by the use of linkers. Examples of suitable linkers include amino acid sequences which may be from 1 amino acid to 150 amino acids in length, or from 1 amino acid to 140 amino acids, for example, from 1 amino acid to 130 amino acids, or from 1 to 120 amino acids, or from 1 to 80 amino acids, or from 1 to 50 amino acids, or from 1 to 20 amino acids, or from 1 to 10 amino acids, or from 5 to 18 amino acids. Such sequences may have their own tertiary structure, for example, a linker of the present invention may comprise a single variable domain. The size of a linker in one embodiment is equivalent to a single variable domain. Suitable linkers may be of a size from 1 to 100 angstroms, for example may be of a size from 20 to 80 angstroms or for example may be of a size from 20 to 60 angstroms or for example less than 40 angstroms, or less than 20 angstroms, or less than 5 angstroms in length.

In one embodiment of the present invention, ICOS binding proteins are provided comprising one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR.

In one embodiment of the present invention, ICOS binding proteins are provided which specifically binds to human ICOS comprising a $V_H$ domain comprising an amino acid sequence at least 90% identical to the amino acid sequence set forth in SEQ ID NO:7 and/or a $V_L$ domain comprising an amino acid sequence at least 90% identical to the amino acid sequence set forth in SEQ ID NO:8. In one aspect, the ICOS binding proteins of the present invention, also bind to cynomolgus ICOS. In one aspect, they do not bind to murine ICOS.

In one embodiment, the ICOS binding proteins of the invention are ICOS agonists. In one aspect, the ICOS binding proteins increase IFN-gamma production in the presence of Tcells. In another aspect, the ICOS binding proteins of the present invention stimulate Tcell proliferation.

In one embodiment, the ICOS binding protein of the invention bind to human ICOS with
an association rate constant (kon) of at least 1×10⁵ M-1s-1; and a dissociation rate constant (koff) of less than 6×10-5 s-1; or
a dissociation constant (Kd) of less than 100 nM
wherein the high affinity is measured by Biacore.

In one embodiment the ICOS binding protein comprises CDRH3 (SEQ ID NO:3) or a variant of SEQ ID NO. 3. In another embodiment the ICOS binding proteins comprise one or more of: CDRH1 (SEQ ID NO:1); CDRH2 (SEQ ID NO:2); CDRH3 (SEQ ID NO:3); CDRL1 (SEQ ID NO:4); CDRL2 (SEQ ID NO:5); and/or CDRL3 (SEQ ID NO:6). In one embodiment, the ICOS binding proteins comprise heavy chain CDRs as set forth in SEQ ID NO:1; SEQ ID NO:2; and SEQ ID NO:3 and light chain CDRs as set forth in SEQ ID NO:4; SEQ ID NO:5; and SEQ ID NO:6.

In one embodiment, the ICOS binding proteins comprise a $V_H$ domain having 90% sequence identity to the amino acid sequence set forth in SEQ ID NO:7; and a $V_L$ domain having 90% sequence identity to the amino acid sequence shown in the amino acid sequence set forth in SEQ ID NO:8. In one aspect, the ICOS binding proteins comprise a $V_H$ domain having the amino acid sequence set forth in SEQ ID NO.7 and the $V_L$ domain comprising the amino acid sequence as set forth in SEQ ID NO:8. In one aspect, the ICOS binding proteins comprise a heavy chain variable domain consisting of SEQ ID NO:7. In one aspect, the ICOS binding protein comprises a light chain variable domain consisting of SEQ ID NO:8.

In one embodiment, the invention provides an ICOS binding protein or antigen binding portion thereof comprising a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8 wherein said ICOS binding protein or antigen binding portion thereof specifically binds to human ICOS. In one embodiment, the ICOS binding protein or antigen binding portion thereof comprising a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8 wherein said ICOS binding protein or antigen binding portion thereof specifically binds to human ICOS further comprises heavy chain CDRs having the amino acid sequences set forth in SEQ ID NO:1; SEQ ID NO:2; and SEQ ID NO:3 and light chain CDRs having the amino acid sequences set forth in SEQ ID NO:4; SEQ ID NO:5; and SEQ ID NO:6. In one aspect, the ICOS binding protein or antigen binding portion thereof comprises a $V_H$ domain comprising an amino acid sequence set forth in SEQ ID NO:7; and a $V_L$ domain comprises the amino acid sequence set forth in SEQ ID NO:8. In one embodiment, the ICOS binding protein or antigen binding portion thereof is an agonist to human ICOS. In one embodiment the ICOS binding protein or antigen binding portion thereof further comprising an IgG4 isotype scaffold or a variant thereof. In one embodiment, the ICOS binding protein or antigen binding portion thereof comprises a hIgG4PE scaffold.

In one embodiment, the ICOS binding protein of the present invention is a humanized monoclonal antibody comprising a heavy chain amino acid sequence having at least 90%, 91%, 92,%, 93%, 94%, 95%, 96%, 97%, 98%, 99% or 100% sequence identity to the amino acid sequence set forth in SEQ ID NO:23.

(SEQ ID NO: 23)
QVQLVQSGAEVKKPGSSVKVSCKASGYTFT<u>DYAMH</u>WVRQAPGQGLEWMG<u>LI

SIYSDHTNYNQKFQG</u>RVTITADKSTSTAYMELSSLRSEDTAVYYCGR<u>NNYG

NYGWYFDV</u>WGQGTTVTVSSASTKGPSVFPLAPCSRSTSESTAALGCLVKDY

FPEPVTVSWNSGALTSGVHTFPAVLQSSGLYSLSSVVTVPSSSLGTKTYTC

NVDHKPSNTKVDKRVESKYGPPCPPCPAPEFEGGPSVFLFPPKPKDTLMIS

RTPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQE

EMTKNQVSLTCLVKGFYPSDIAVEWESNGQPENNYKTTPPVLDSDGSFFLY

SRLTVDKSRWQEGNVFSCSVMHEALHNHYTQKSLSLSLGK

In one embodiment, the ICOS binding protein of the present invention is a humanized monoclonal antibody comprising a light chain amino acid sequence having at least 90%, 91%, 92,%, 93%, 94%, 95%, 96%, 97%, 98%, 99% or 100% sequence identity to the amino acid sequence set forth in SEQ ID NO:24.

(SEQ ID NO:24)
EIVLTQSPATLSLSPGERATLSC<u>SASSSVSYMH</u>WYQQKPGQAPRLLIY<u>DTS

KLAS</u>GIPARFSGSGSGTDYTLTISSLEPEDFAVYYC<u>FQGSGYPYT</u>FGQGTK

LEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPV

TKSFNRGEC

In one embodiment, the ICOS binding protein of the present invention is a humanized monoclonal antibody comprising the heavy chain amino acid sequence set forth in SEQ ID NO:23 and the light chain amino acid sequence set forth in SEQ ID NO:24. In one embodiment, the ICOS binding protein of the present invention further comprises an hIgGPE scaffold.

In one embodiment, the ICOS binding protein or antigen binding portion thereof wherein said ICOS binding protein is a humanized monoclonal antibody. Also provided by the present invention are pharmaceutical compositions comprising the ICOS binding protein or antigen binding portion thereof of claim and a pharmaceutically acceptable carrier.

The present invention provides methods of treating a disease selected from cancer, infectious disease, and/or sepsis in a human in need thereof which method comprises the step of administering a pharmaceutical composition of the present invention said human. In one aspect, the method further comprises administering at least one anti-neoplastic agent, at least one second immune-modulatory agent, and/or at least one immunostimulatory adjuvant to said human. In one aspect, the second immuno-modulatory agent is selected from: an anti-CTLA4 antibody, and anti-PD-1 antibody, an anti-PDL1 antibody and an anti OX40 antibody. In one aspect the anti-CTLA4 antibody is ipilimumab. In one aspect the anti-PD-1 antibody is selected from pembrolizumab and/or nivolumab.

In one embodiment of the present invention, methods are provided for treating cancer in a human comprising administering a therapeutically acceptable amount of the ICOS binding protein or antigen binding portion thereof to a human. In some aspects the cancer is selected from colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer.

In one embodiment, methods are provided for treating infectious disease in a human comprising administering a therapeutically acceptable amount of the ICOS binding protein or antigen binding portion thereof to a human. In one aspect, the infectious diseases is HIV.

In one embodiment, methods are provided for treating sepsis in a human comprising administering a therapeutically acceptable amount of the ICOS binding protein or antigen binding portion thereof to a human.

In one embodiment, methods are provided for stimulating T cell proliferation, inducing T cell activation and/or inducing cytokine production in a human comprising administering a pharmaceutical composition of the invention to said human.

The present invention also provides polynucleotides encoding the ICOS binding protein or antigen binding portion thereof of the present invention. In one embodiment, host cells are provided comprising polynucleotides encoding the ICOS binding proteins or antigen binding portions thereof of the present invention. The present invention also provides methods of making an ICOS binding protein or antigen binding portion thereof comprising the steps of a) culturing host cell comprising a polynucleotide encoding an ICOS binding protein or antigen binding portion thereof of the present invention under suitable conditions to express said ICOS binding protein or antigen binding portion thereof and b) isolating said ICOS binding protein or antigen binding portion thereof.

The present invention provides an isolated humanized monoclonal antibody comprising a $V_H$ domain comprising an amino acid sequence set forth in SEQ ID NO:7; a $V_L$ domain comprising an amino acid sequence set forth in SEQ ID NO:8; and a hIgG4 scaffold or a variant thereof. In one aspect, the hIgG4 scaffold is hIgG4PE.

In one embodiment, ICOS binding proteins or antigen binding portions thereof are provided, wherein the ICOS binding protein or antigen binding portion thereof cross-competes for binding for human ICOS with a reference antibody or antigen binding portion thereof comprising a $V_H$ domain comprising an amino acid sequence set forth in SEQ ID NO:7; and a $V_L$ domain comprising the amino acid sequence set forth in SEQ ID NO:8.

In one embodiment, the ICOS binding proteins of the invention stimulate T cell proliferation when placed in contact with a T cell. In one embodiment, the ICOS binding proteins of the invention induce T cell activation when placed in contact with a T cell. T cell activation can be measured by an increase in percent expression levels of certain activation markers such as, but not limited to, CD69, CD25, and/or OX40. In one embodiment, the ICOS binding proteins of the present invention stimulate cytokine production when placed in contact with a T cell. The ICOS binding proteins bind to human FcγRIIb but do not bind to human FcγRIIa or human FcγRIIIa. Additionally, the ICOS binding proteins suitably do not deplete ICOS expressing T cells when contacted with ICOS expressing T cells. In some aspects, the ICOS binding proteins cross-link a T cell with a second cell when contacted with said T cell in the presence of a second cell. This cross-linking can occur through engagement of the ICOS binding protein with a FcγR on the second cell. FcγR expressing cells include, but are not limited to monocytes, B lymphocytes, follicular dendritic cells, natural killer cells, macrophages, neutrophils, eosinophils, basophils, and mast cells. Thus, in one embodiment the ICOS binding proteins can be administered to a mammal wherein the ICOS binding protein will act as an agonist to ICOS on a T cell and will also engage an FcγR on a second cell.

In one embodiment, the ICOS binding proteins comprise a scaffold selected from human IgG1 isotype or variant thereof and human IgG4 isotype or variant thereof. Suitably, the scaffold comprises a human IgG4 isotype scaffold or variant thereof. In one aspect, the scaffold comprises a hIgG4PE scaffold.

In one embodiment, the ICOS binding protein is a monoclonal antibody. Suitably the ICOS binding protein is a humanized monoclonal antibody. In one aspect the monoclonal antibodies of the present invention can be fully human.

In another aspect, the ICOS binding protein is a fragment which is a Fab, Fab', F(ab')$_2$, Fv, diabody, triabody, tetrabody, miniantibody, minibody, isolated $V_H$ or isolated $V_L$. In one embodiment, the ICOS binding protein is an antigen binding portion thereof.

In some aspects the ICOS binding protein binds to human ICOS with an affinity of stronger than 0.6 nM. In one aspect, the affinity is 100 nM or stronger. In one embodiment the ICOS binding protein has a KD of 100 nM for ICOS. Suitably, the KD of the ICOS binding protein for ICOS is 100 nM or less, 50 nM or less, 25 nM or less, 10 nM or less, 2 nM or less or 1 nM or less.

In one embodiment, the present invention provides humanized monoclonal antibodies that are agonists to human ICOS. In one embodiment, the present invention provides humanized monoclonal antibodies comprising heavy chain variable region CDRs having the amino acid sequences set forth in SEQ ID NO:1; SEQ ID NO:2; and SEQ ID NO:3 and light chain variable region CDRS having the amino acid sequences set forth in SEQ ID NO:4; SEQ ID NO:5; and SEQ ID NO:6. In one aspect, the humanized monoclonal antibody is able to stimulate cytokine production and/or T cell proliferation when contacted with a T cell while not inducing complement, ADCC or CDC. In one embodiment, the humanized monoclonal antibody has variant human IgG1 Fc region. In one embodiment, the humanized monoclonal antibody has a human IgG4 Fc region or variant thereof. In one embodiment, the humanized monoclonal antibody has a hIgG4PE Fc region. In one aspect, the humanized monoclonal antibody comprises a $V_H$ domain comprising an amino acid sequence at least 90% identical to the amino acid sequence as set forth in SEQ ID NO:7; and a $V_L$ domain comprising an amino acid sequence at least 90% identical to the amino acid sequence as set forth in SEQ ID NO:8. In one aspect the humanized monoclonal antibody comprises a $V_H$ domain comprising an amino acid sequence set forth in SEQ ID NO:7; and a $V_L$ domain comprising the amino acid sequence as set forth in SEQ ID NO:8. In one aspect the humanized monoclonal antibody comprises and hIgG4PE scaffold. Furthermore, humanized monoclonal antibodies of the present invention are shown to stimulate T cell proliferation when contacted with a CD4+ or a CD8+ T cell. Humanized monoclonal antibodies of the present invention are shown to induce T cell activation and stimulate cytokine production.

In one embodiment, the humanized monoclonal antibody comprises an hIgG4PE scaffold and comprises a $V_H$ domain comprising an amino acid sequence set forth in SEQ ID NO:7 and a $V_L$ domain comprising an amino acid sequence set forth in SEQ ID NO:8. The antibodies of the present invention may stimulate cytokine production when contacted with a T cell.

In one embodiment, an ICOS binding protein is provided that competes for ICOS binding with any one of the ICOS binding proteins of the invention. As is understood in the art and described herein, binding competition can be measured by comparing competition for ligand binding to ICOS in the presence of one or more ICOS binding proteins. As is also understood in the art, ICOS is expressed on CD4+ and CD8+ T cells as well as Treg cells. The ICOS binding proteins of the present invention act as agonist to ICOS on T cells. They also act to block the interaction between ICOS-L and ICOS expressed on both T cells and Treg cells. Thus, in one embodiment, methods are provided to block the interaction of ICOS-L with ICOS on Treg cells. ICOS expressing Treg cells can be found in various types of tumors including liquid tumors such as lymphoma. Thus, in one aspect of the present invention, methods of treating a cancer are provided comprising administering an ICOS binding protein of the invention wherein the ICOS binding protein blocks the interaction of ICOS-L with ICOS on Treg cells.

Further to the invention, are pharmaceutical compositions comprising an ICOS binding protein or a monoclonal antibody described herein. In one aspect the pharmaceutical composition of the present invention further comprise at least one anti-neoplastic agent. In one aspect the pharmaceutical composition of the present invention further comprise at least one second immunomodulatory agent. In one aspect, the pharmaceutical composition of the present invention further comprising at least one immunostimulatory adjuvant.

In one embodiment, methods are provided for treating cancer and/or infectious disease in a human in need thereof wherein said method comprises the step of administering a pharmaceutical composition of the invention to said human. In one embodiment the human has cancer. In one embodiment the human has an infectious disease. In one embodiment the human has HIV. In one aspect the method further comprises administering at least one anti-neoplastic agent to said human. In another aspect the method further comprises administering at least one second immune-modulatory agent to said human. In yet another aspect the method further comprises administering an immunostimulatory adjuvant to said human.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

By the term "treating" and grammatical variations thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, (4) to slow the progression of the condition or one or more of the biological manifestations of the condition and/or (5) to cure said condition or one or more of the biological manifestations of the condition by eliminating or reducing to undetectable levels one or more of the biological manifestations of the condition for a period of time considered to be a state of remission for that manifestation without additional treatment over the period of remission. One skilled in the art will understand the duration of time considered to be remission for a particular disease or condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The ICOS binding proteins, antibodies and antigen binding fragments of the invention can also be used to cure, prevent or treat infections and infectious disease. The ICOS binding proteins can be used alone, or in combination with vaccines, to stimulate the immune response to pathogens, toxins, and self-antigens. The ICOS binding proteins of the present invention can be used to stimulate immune response to viruses infectious to humans, such as, but not limited to, human immunodeficiency viruses, hepatitis viruses class A, B and C, Eppstein Barr virus, human cytomegalovirus, human papilloma viruses, herpes viruses. The ICOS binding proteins of the present invention can be used to stimulate immune response to infection with bacterial or fungal parasites, and other pathogens. Suitably, the present invention provides methods for treating humans that have been exposed to particular toxins or pathogens. Accordingly, another aspect of the invention provides a method of treating an infectious disease in a subject comprising administering to the subject ICOS binding protein, or antigen-binding portion thereof.

Examples of infectious disease for which the ICOS binding proteins of the present invention may be useful include, but are not limited to, HIV, Hepatitis (A, B, & C), Influenza, Herpes, *Giardia*, Malaria, *Leishmania, Staphylococcus aureus, Pseudomonas Aeruginosa*. Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Sepsis is a potentially deadly medical condition that is characterized by a whole-body inflammatory state (called a systemic inflammatory response syndrome or SIRS) and the presence of a known or suspected infection. The body may develop this inflammatory response by the immune system to microbes in the blood, urine, lungs, skin, or other tissues. A lay term for sepsis is blood poisoning, more aptly applied to septicemia, below. Severe sepsis is the systemic inflammatory response, plus infection, plus the presence of organ dysfunction.

Septicemia is a related medical term referring to the presence of pathogenic organisms in the bloodstream, leading to sepsis. The term has not been sharply defined.

Sepsis and cancer share similar immunosuppressive mechanisms including increased T regulatory cells, increased myeloid derived suppressor cells, increased expression of negative co-stimulatory molecules, decreased monocyte/macrophage HLA-DR expression. Sepsis and cancer are prototypical disorders of chronic inflammation. Chronic inflammation stimulates potent and sustained immunoregulatory responses, including expansion of T regulatory cells and up-regulation of PD-1 and other negative regulators on effector cells. Barouch D. H. and Deeks S. G.; Immunologic strategies for HIV-1 remission and eradication. *Science* 345:169-174 2014. Thus, in one aspect of the present inventions methods are provided for treating sepsis in a human in need thereof comprising administering a therapeutically effective amount of an ICOS antigen binding protein of the present invention to said human. Boomer, et al. *JAMA* 306:2594-2605 (2011); Meisel, et al. Granulocyte-macrophage colony-stimulating factor to reverse sepsis-associated immunosuppression: a double-blind, randomized, placebo-controlled multicenter trial. *Am J Respir Crit Care Med* 180:640-648 (2009); and Hall, et al. Immunoparalysis and nosocomial infection in children with multiple organ dysfunction syndrome. Intensive *Care Med* 37:525-532 (2011).

The ICOS binding proteins of the invention can be used in conjunction with other recombinant proteins and/or peptides (such as tumor antigens or cancer cells) in order to increase an immune response to these proteins (i.e., in a vaccination protocol).

For example, ICOS binding proteins thereof may be used to stimulate antigen-specific immune responses by co-administration of at least one ICOS binding protein with an antigen of interest (e.g., a vaccine). Accordingly, in another aspect the invention provides a method of enhancing an immune response to an antigen in a subject, comprising administering to the subject: (i) the antigen; and (ii) an ICOS binding protein of the invention, such that an immune response to the antigen in the subject is enhanced. The antigen can be, for example, a tumor antigen, a viral antigen, a bacterial antigen or an antigen from a pathogen. Non-limiting examples of such antigens include, without limitation, tumor antigens, or antigens from the viruses, bacteria or other pathogens.

A major hurdle to HIV eradication is the maintenance of latently infected cells that do not express viral antigens, and escape immune surveillance. Current strategies to eliminate the latent viral reservoir referred to as the "kick and kill" strategy, aims to reactivate HIV gene expression ("kick") as cellular activation leads to HIV reactivation, and clear reactivated cells ("kill"). Cellular activation is governed by a balance of positive and negative regulators expressed on the surface of T cells. Altering this balance by agonising positive regulators and antagonising negative ones may facilitate HIV reactivation.

Inducible T cell Co-Stimulator (ICOS) is a positive regulator whose expression increases on CD4 T cells following stimulation. ICOS functions to promote T cell proliferation, cytokine production and differentiation. One important T cell subset that expresses high levels of PD-1 and ICOS is T follicular helper cells (Tfh). Tfh cells help B cells undergo differentiation, class switching, somatic hypermutation and are necessary for germinal center formation. Tfh cells are significantly expanded following HIV/SIV infection and their dysregulation during chronic lentiviral infection contributes to impaired B cell immunity. Sorted Tfh cells have been shown to contain higher levels of HIV DNA than other lymphoid CD4 subsets and virus outgrowth is observed following stimulation. Tfh cells reside in germinal centers and are exposed to HIV virions trapped on follicular dendritic cells that may facilitate their infection. In addition, CD8 T cells have limited access to germinal centers and follicular CD8 cells often demonstrate reduced cytotoxicity, thus sparing Tfh cells from antiviral surveillance. Thus, Tfh cells are an important protected HIV reservoir and strategies that target PD-1 and ICOS may selectively target Tfh cells and have utility as part of an HIV cure regimen. Suitably, methods are provided for treating a human infected with HIV comprising administering an ICOS binding protein or the antigen binding portion thereof of the present invention.

As used herein "tumor antigens" are proteins that are produced by tumor cells that elicit an immune response, particularly T-cell mediated immune responses. The term "tumor antigen" as used herein includes both tumor-specific antigens and tumor-associated antigens. Tumor-specific antigens are unique to tumor cells and do not occur on other cells in the body. Tumor-associated antigens are not unique to a tumor cell and instead is also expressed on a normal cell under conditions that fail to induce a state of immunologic tolerance to the antigen. The expression of the antigen on the tumor may occur under conditions that enable the immune system to respond to the antigen. Tumor-associated antigens may be antigens that are expressed on normal cells during fetal development when the immune system is immature and unable to respond or they may be antigens that are normally present at extremely low levels on normal cells but which are expressed at much higher levels on tumor cells.

Non-limiting examples of tumor antigens include the following: differentiation antigens such as MART-1/MelanA (MART-I), gp100 (Pmel 17), tyrosinase, TRP-1, TRP-2 and tumor-specific multilineage antigens such, MAGE family antigens including but not limited to MAGE1, MAGE3, MAGE10, MAGE11, MAGE12, MAGEA2, MAGEA3, MAGEA4, MAGEA6, MAGEA8, MAGEA9, MAGEB18, MAGEB6, MABEC1, MAGED2, MAGEE1, MAGEH1, MAGEL2, BAGE, GAGE-1, GAGE-2, p15; MEL4, melanoma associated antigen 100+, melanoma gp100, NRIP3, NYS48, OCIAD1, OFA-iLRP, OIP5, ovarian carcinoma-associated antigen (OV632), PAGE4, PARP9, PATE, plastin L, PRAME, prostate-specific antigen, proteinase 3, prostein, Reg3a, RHAMM, ROPN1, SART2, SDCCAG8, SEL1L, SEPT1, SLC45A2, SPANX, SSX5, STXGALNAC1, STEAP4, survivin, TBC1D2, TEM1, TRP1, tumor antigens of epithelial origin, XAGE1, XAGE2, WT-1; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7.

Other tumor antigens include, but are not limited to, TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, TPS, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), ELF2M, neutrophil elastase, ephrinB2, CD19, CD20, CD22, ROR1, CD33/ IL3Ra, c-Met, PSMA, Glycolipid F77, EGFRvIII, GD-2, insulin growth factor (IGF)-I, IGF-II, IGF-I receptor and mesothelin.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signalling inhibitors.

Examples of a further active ingredient or ingredients for use in combination or co-administered with the present ICOS binding protein are anti-neoplastic agents including any chemotherapeutic agents, immuno-modulatory agents or immune-modulators and immunostimulatory adjuvants.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G2/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. lntem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994, lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloID Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethy)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-1(3-amino-2,3,6-trideoxy-α-L-lyxo-hexopyranosyl)oxyl-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia CLL; a type of cancer of the white blood cells) in adults who are refractory to treatment with fludarabine (Fludara) and alemtuzumab Campath).

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl) ethenyl] benzoic acID Bexarotene is used to treat cutaneous T-cell lymphoma CTCL, a type of skin cancer) in people whose disease could not be treated successfully with at least one other medication.

Sorafenib marketed as Nexavar® is in a class of medications called multikinase inhibitors. Its chemical name is 4-[4-[[4-chloro-3-(trifluoromethyl)phenyl]carbamoylamino] phenoxy]-N-methyl-pyridine-2-carboxamide. Sorafenib is used to treat advanced renal cell carcinoma (a type of cancer that begins in the kidneys). Sorafenib is also used to treat unresectable hepatocellular carcinoma (a type of liver cancer that cannot be treated with surgery).

Examples of erbB inhibitors include lapatinib, erlotinib, and gefitinib. Lapatinib, N-(3-chloro-4-{[(3-fluorophenyl) methyl]oxy}phenyl)-6-[5-({[2-(methylsulfonyl)ethyl] amino}methyl)-2-furanyl]-4-quinazolinamine (represented by formula II, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

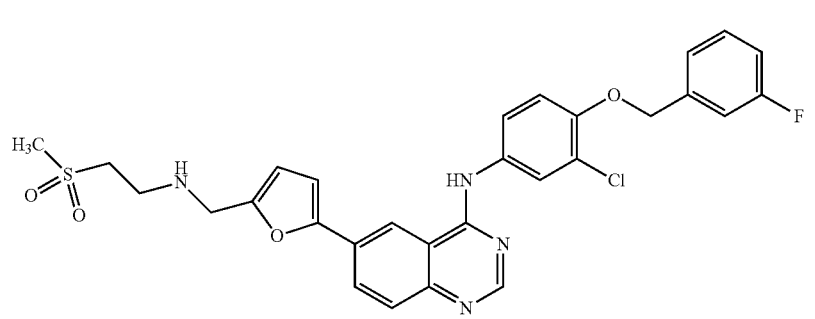

II

The free base, HCl salts, and ditosylate salts of the compound of formula (II) may be prepared according to the procedures disclosed in WO 99/35146, published Jul. 15, 1999; and WO 02/02552 published Jan. 10, 2002.

Erlotinib, N-(3-ethynylphenyl)-6,7-bis{[2-(methyloxy)ethyl]oxy}-4-quinazolinamine Commercially available under the tradename Tarceva) is represented by formula III, as illustrated:

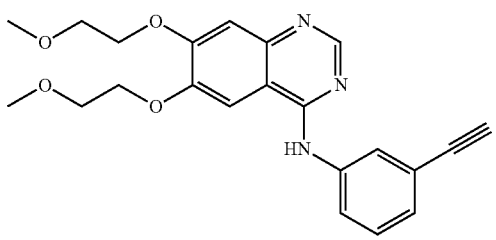

III

The free base and HCl salt of erlotinib may be prepared, for example, according to U.S. Pat. No. 5,747,498, Example 20.

Gefitinib, 4-quinazolinamine,N-(3-chloro-4-fluorophenyl)-7-methoxy-6-[3-4-morpholin)propoxy] is represented by formula IV, as illustrated:

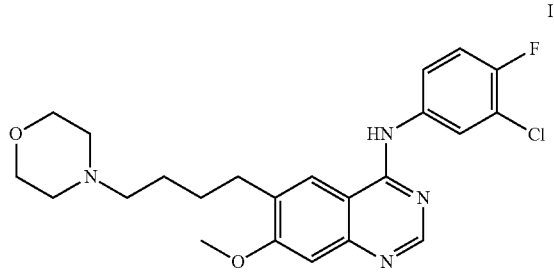

IV

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of gefitinib may be prepared according to the procedures of International Patent Application No. PCT/GB96/00961, filed Apr. 23, 1996, and published as WO 96/33980 on Oct. 31, 1996.

Also of interest, is the camptothecin derivative of formula A following, currently under development, including the racemic mixture (R,S) form as well as the R and S enantiomers:

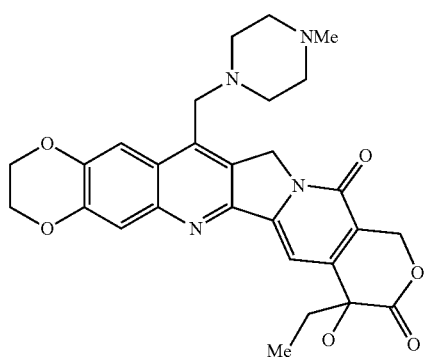

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signalling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor Cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signalling inhibitors such as phospholipase C blockers and Myoinositol analogues. Such signal inhibitors are described in Powis, G., and Kozikowski A., (1994 New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4 292-8; Ashby, M. N. (1998), Current Opinion in Lipidology. 9 (2) 99-102; and Bennett, C. F. and Cowsert, L. M. BioChim. Biophys. Acta, (1999) 1489(1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4, 269-286); Herceptin® erbB2 antibody (see Tyrosine Kinase Signalling in Breast cancer: erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124.

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha beta3) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994, Antisense Res. Dev. 4: 71-79.

Trastuzumab (HEREPTIN®) is a humanized monoclonal antibody that binds to the HER2 receptor. It original indication is HER2 positive breast cancer.

Trastuzumab emtansine (trade name Kadcyla) is anantibody-drug conjugate consisting of the monoclonal antibody trastuzumab (Herceptin) linked to the cytotoxic agent mertansine (DM1). Trastuzumab alone stops growth of cancer cells by binding to the HER2/neu receptor, whereas mertansine enters cells and destroys them by binding to tubulin. Because the monoclonal antibody targets HER2, and HER2 is only overexpressed in cancer cells, the conjugate delivers the toxin specifically to tumor cells. The conjugate is abbreviated T-DM1.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Cell cycle signalling inhibitors inhibit molecules involved in the control of the cell cycle. A family of protein kinases called cyclin dependent kinases CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

As used herein "immuno-modulators" refer to any substance including monoclonal antibodies that effects the immune system. The ICOS binding proteins of the present invention can be considered immune-modulators. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, OX-40 antibodies, PD-L1 antibodies, LAG3 antibodies, TIM-3 antibodies, 41BB antibodies and GITR antibodies.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3k/Akt pathway activation. Other names for nivolumab include: BMS-936558, MDX-1106, and ONO-4538. The amino acid sequence for nivolumab and methods of using and making are disclosed in U.S. Pat. No. 8,008,449.

KEYTRUDA/pembrolizumab is an anti-PD-1 antibodies marketed for the treatment of lung cancer by Merck. The amino acid sequence of pembrolizumab and methods of using are disclosed in U.S. Pat. No. 8,168,757.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in US Patent Nos: U.S. Pat. No. 7,504,101; U.S. Pat. No. 7,758,852; U.S. Pat. No. 7,858,765; U.S. Pat. No. 7,550,140; U.S. Pat. No. 7,960,515; WO2012027328; WO2013028231.

Antibodies to PD-L1 (also referred to as CD274 or B7-H1) and methods for use are disclosed in U.S. Pat. No. 7,943,743; U.S. Pat. No. 8,383,796; US20130034559, WO2014055897, U.S. Pat. No. 8,168,179; and U.S. Pat. No. 7,595,048. PD-L1 antibodies are in development as immuno-modulatory agents for the treatment of cancer.

As used herein "immunostimulatory agent" refers to any agent that can stimulate the immune system. As used herein immunostimulatory agents include, but are not limited to, vaccine adjuvants.

Aminoalkyl glucosaminide phosphates (AGPs) are known to be useful as vaccine adjuvants and immunostimulatory agents for stimulating cytokine production, activating macrophages, promoting innate immune response, and augmenting antibody production in immunized animals. Aminoalkyl glucosaminide phosphates (AGPs) are synthetic ligands of the Toll-like Receptor 4 (TLR4). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. No. 7,129,219, U.S. Pat. No. 6,525,028 and U.S. Pat. No. 6,911,434. Certain AGPs act as agonists of TLR4, while others are recognized as TLR4 antagonists.

Aminoalkyl glucosaminide phosphate compounds employed in the present invention have the structure set forth in Formula 1 as follows:

(Formula 1)

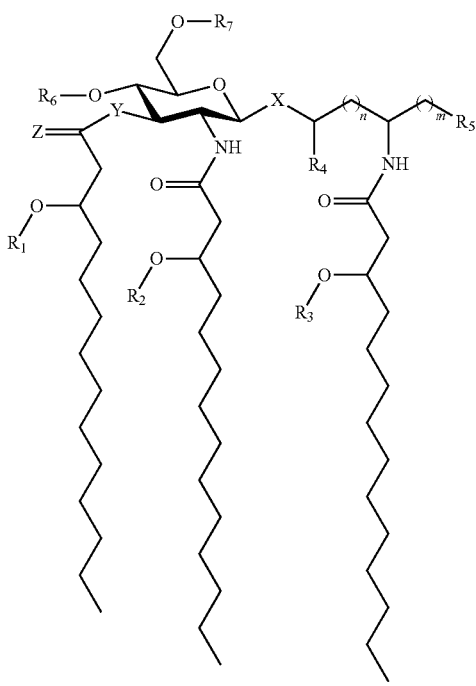

wherein m is 0 to 6 n is 0 to 4;

X is O or S, preferably O;

Y is O or NH;

Z is O or H;

each $R_1$, $R_2$, $R_3$ is selected independently from the group consisting of a $C_{1-20}$ acyl and a $C_{1-20}$ alkyl;

$R_4$ is H or Me;

$R_5$ is selected independently from the group consisting of —H, —OH, —($C_1$-$C_4$) alkoxy, —$PO_3R_8R_9$, —$OPO_3R_8R_9$, —$SO_3R_8$, —$OSO_3R_8$, —$NR_8R_9$, —$SR_8$, —CN, —$NO_2$, —CHO, —$CO_2R_8$, and —$CONR_8R_9$, wherein $R_8$ and $R_9$ are each independently selected from H and ($C_1$-$C_4$) alkyl; and each $R_6$ and $R_7$ is independently H or $PO_3H_2$.

In Formula 1 the configuration of the 3' stereogenic centers to which the normal fatty acyl residues (that is, the secondary acyloxy or alkoxy residues, e.g., $R_1O$, $R_2O$, and $R_3O$) are attached is R or S, preferably R (as designated by Cahn-Ingold-Prelog priority rules). Configuration of aglycon stereogenic centers to which $R_4$ and $R_5$ are attached can be R or S. All stereoisomers, both enantiomers and diastereomers, and mixtures thereof, are considered to fall within the scope of the present invention.

The number of carbon atoms between heteroatom X and the aglycon nitrogen atom is determined by the variable "n", which can be an integer from 0 to 4, preferably an integer from 0 to 2.

The chain length of normal fatty acids $R_1$, $R_2$, and $R_3$ can be from about 6 to about 16 carbons, preferably from about 9 to about 14 carbons. The chain lengths can be the same or different. Some preferred embodiments include chain lengths where $R_1$, $R_2$ and $R_3$ are 6 or 10 or 12 or 14.

Formula 1 encompasses L/D-seryl, -threonyl, -cysteinyl ether and ester lipid AGPs, both agonists and antagonists and their homologs (n=1-4), as well as various carboxylic acid bioisosteres (i.e, $R_5$ is an acidic group capable of salt formation; the phosphate can be either on 4- or 6-position of the glucosamine unit, but preferably is in the 4-position).

In a preferred embodiment of the invention employing an AGP compound of Formula 1, n is 0, $R_5$ is $CO_2H$, $R_6$ is $PO_3H_2$, and $R_7$ is H. This preferred AGP compound is set forth as the structure in Formula 1a as follows:

(Formula 1a)

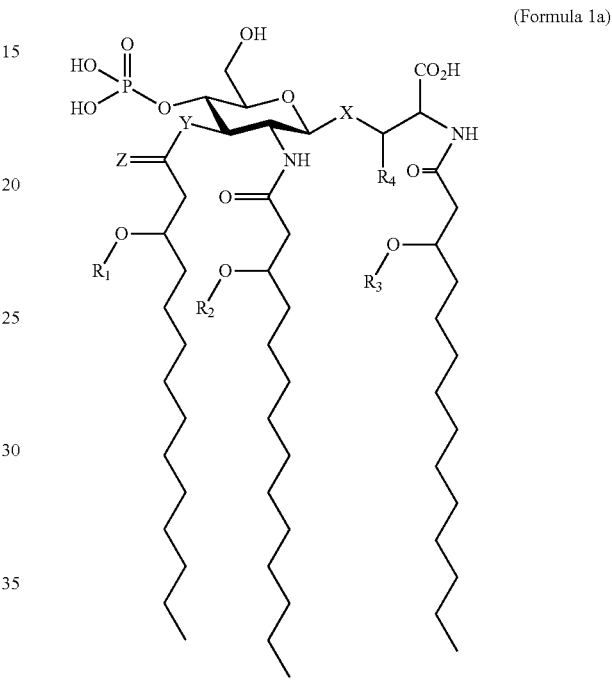

wherein X is O or S; Y is O or NH; Z is O or H; each $R_1$, $R_2$, $R_3$ is selected independently from the group consisting of a $C_{1-20}$ acyl and a $C_{1-20}$ alkyl; and $R_4$ is H or methyl.

In Formula 1a the configuration of the 3' stereogenic centers to which the normal fatty acyl residues (that is, the secondary acyloxy or alkoxy residues, e.g., $R_1O$, $R_2O$, and $R_3O$) are attached as R or S, preferably R (as designated by Cahn-Ingold-Prelog priority rules). Configuration of aglycon stereogenic centers to which $R_4$ and $CO_2H$ are attached can be R or S. All stereoisomers, both enantiomers and diastereomers, and mixtures thereof, are considered to fall within the scope of the present invention.

Formula 1a encompasses L/D-seryl, -threonyl, -cysteinyl ether or ester lipid AGPs, both agonists and antagonists.

In both Formula 1 and Formula 1a, Z is O attached by a double bond or two hydrogen atoms which are each attached by a single bond. That is, the compound is ester-linked when Z=Y=O; amide-linked when Z=O and Y=NH; and ether-linked when Z=H/H and Y=O.

Especially preferred compounds of Formula 1 are referred to as CRX-601 and CRX-527. Their structures are set forth as follows:

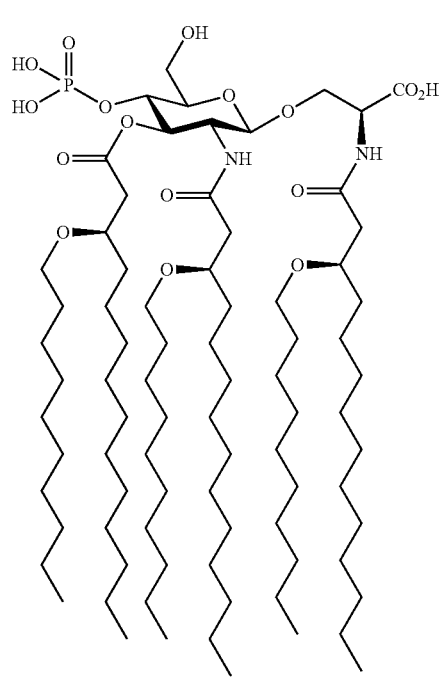
(CRX-601)
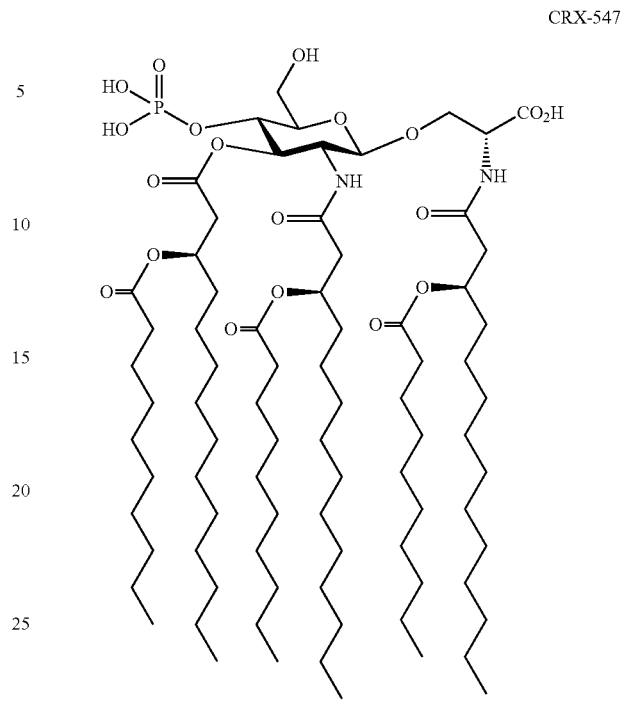
CRX-547
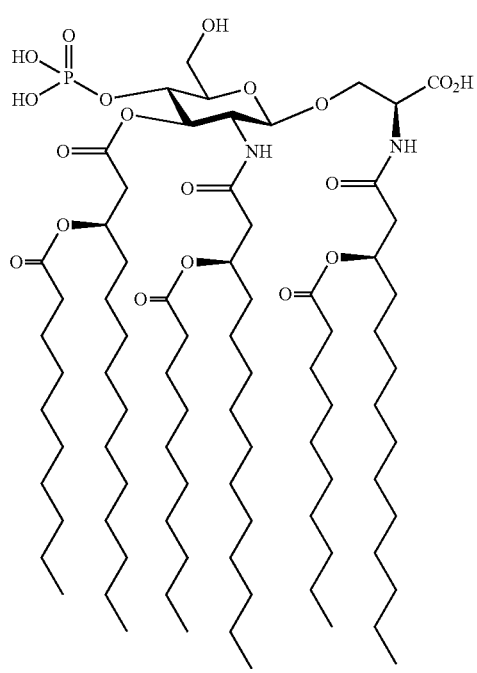
(CRX-527)
Still other embodiments include AGPs such as CRX 602 or CRX 526 providing increased stability to AGPs having shorter secondary acyl or alkyl chains.
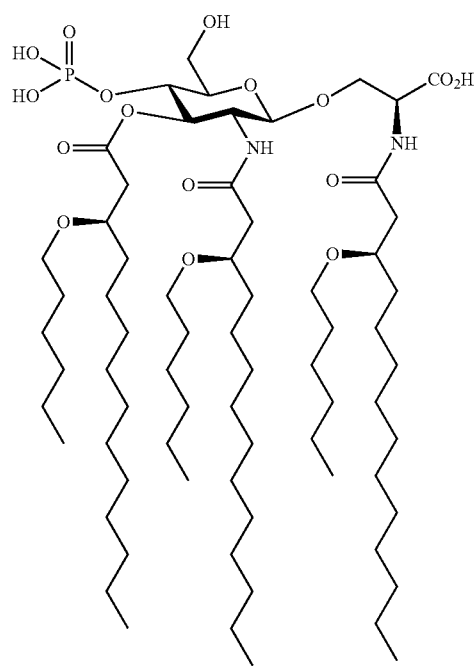
CRX 602
Additionally, another preferred embodiment employs CRX 547 having the structure shown.

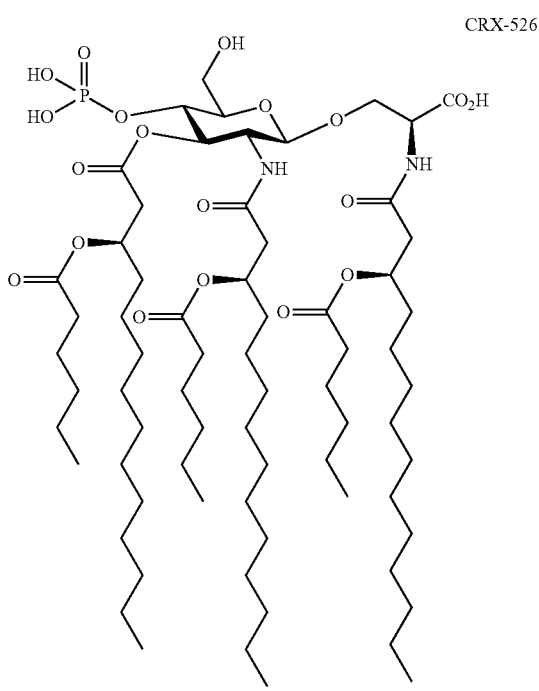

CRX-526

In one embodiment methods are provided for treating cancer in a mammal in need thereof, which comprises: administering to such mammal a therapeutically effective amount of:
an ICOS binding protein of the present invention,
and b) at least one anti-neoplastic agent.

In one embodiment methods are provided for treating cancer in a mammal in need thereof, which comprises: administering to such mammal a therapeutically effective amount of:
an ICOS binding protein of the present invention,
and b) at least one second immuno-modulatory agent.

In one embodiment said second immune-modulatory agent is selected from the group of: an anti-CTLA4 antibody, an anti-PD-1 antibody, an anti-PD-L1 antibody, an anti-OX40 antibody, an anti-GITR antibody, and anti-41BB antibody, an anti-LAG3 antibody and an anti-TIM3 antibody.

In one embodiment methods are provided for treating cancer in a mammal in need thereof, which comprises: administering to such mammal a therapeutically effective amount of:
an ICOS binding protein or the present invention,
and b) at least one immuno-stimulatory agent.

In one embodiment, the immune-stimulatory agent is a TLR4 agonist. In one embodiment the immune-stimulatory agent is an AGP. In one aspect, the immune-stimulatory agent is a compound of Formula I. In one aspect, it is a compound of Formula 1a. In one aspect, the immune-stimulatory agent is selected from the group consisting of: CRX-601, CRX-547, CRX-602, CRX-527, and CRX-526.

EXAMPLES

The following examples illustrate various non-limiting aspects of this invention.

Example 1: ICOS Expression in Cancer

In general, solid tumors appear to have low levels of infiltrating ICOS$^+$ T cells, consistent with the theory that ICOS mediates anti-tumor immune responses. ICOS expression analyses across various tumor histologies was generated using publically available mRNA expression datasets from The Cancer Genome Atlas (TCGA) and other databases. Table 3 shows the relative percentage of tumors from each histology that showed some detectable level of ICOS mRNA expression. This analysis identifies tumor histologies known to be sensitive to other cancer immunotherapy approaches (melanoma, RCC, NSCLC) as having a relatively higher percentage of tumors (>10%) which have detectable ICOS$^+$ tumor infiltrating lymphocytes (TILs), whereas tumor types known to be poorly immunogenic (prostate, ovarian, and pancreatic) having relatively lower percentage of tumors which have ICOS$^+$ TILs (<10%) (Table 3). Interestingly, tumor types known to be associated with viral infection and/or chronic inflammation (H&N, Gastric, Esophageal, and Cervical) were among the tumor types showing the highest percentage of ICOS$^+$ TILs. What is not clear from these mRNA expression analyses is the subpopulation of TILs which express ICOS in each respective tumor type. In some instances ICOS may be predominantly expressed on tumor infiltrating T$_{regs}$, while in others it may indicate level of ICOS$^+$ T effector cell infiltration.

TABLE 3

ICOS mRNA expression across different tumor types

| Tumor Type | Total N | ICOS+ (N) | ICOS+ (Per.) |
|---|---|---|---|
| H&N | 426 | 157 | 36.9% |
| Gastric | 285 | 75 | 26.3% |
| Esophageal | 70 | 17 | 24.3% |
| Melanoma (M) | 295 | 69 | 23.4% |
| NSCLC (AD) | 501 | 112 | 22.4% |
| NSCLC (SCC) | 489 | 35 | 17.4% |
| Cervical | 185 | 32 | 17.3% |
| Breast | 1048 | 162 | 15.5% |
| Bladder | 244 | 35 | 14.3% |
| RCC | 522 | 64 | 12.3% |
| Melanoma (P) | 82 | 7 | 8.5% |
| Pancreas | 85 | 7 | 8.2% |
| Colon | 446 | 34 | 7.6% |
| Thyroid | 498 | 34 | 6.8% |
| HCC | 191 | 11 | 5.8% |
| Sarcoma | 103 | 4 | 3.9% |
| Ovarian | 412 | 13 | 3.2% |
| Prostate | 336 | 10 | 3.0% |
| Endometrial | 532 | 15 | 2.8% |
| Rectal | 163 | 4 | 2.5% |
| GBM | 156 | 0 | 0.0% |

Analysis of ICOS expression by immunohistochemistry (IHC) in primary human non-small cell lung carcinoma (NSCLC), triple-negative breast cancer (TNBC), colo-rectal cancer (CRC), prostate, pancreatic, ovarian, renal cell cancer (RCC) and melanoma was performed to better understand which subsets of TILs are associated with ICOS expression in different tumor types (Table A). Similar to what was observed in the mRNA expression analysis, the abundance of ICOS$^+$ TILs were relatively low, even in individual tumors where large numbers of CD4$^+$, CD8$^+$ and/or FoxP3$^+$ TILs were otherwise present. Again, melanoma, renal cell carcinoma (RCC) and non-small cell lung carcinoma (NSCLC) histologies had the highest percentage of tumors with some level of detectable ICOS$^+$ infiltrate (Table A, Column 2). Conversely, prostate, ovarian and pancreatic tumors showed almost no ICOS$^+$ TILs (Table A). These analyses clearly show that solid tumors have low basal levels of ICOS$^+$ TILs and may benefit from the expansion and functional induction of this population of cells. Future studies using flow cytometry and dual-color immunohistochemistry to analyze primary human tumors will help determine which specific T cells subsets express ICOS.

TABLE 4

| Entity | No. of samples | ICOS | Average number of positive cells (range) | | | | |
|---|---|---|---|---|---|---|---|
| | | | ICOS | CD3 | CD4 | CD8 | FOXp3 |
| NSCLC | n = 17 | − | 0 | 11 (0-74) | 2 (0-9) | 20 (0-147) | 10 (0-28) |
| (squamous) | n = 23 | + | 3 (0-25) | 38 (2-143) | 8 (0-26) | 39 (5-188) | 18 (0-75) |
| NSC LC | n = 15 | − | 0 | 36 (0-157) | 4 (0-20) | 71 (5-238) | 10 (1-41) |
| (adenocarcinoma) | n = 25 | + | 2 (0-7) | 56 (0-181) | 8 (0-39) | 69 (10-201) | 19 (0-55) |
| TNBC | n = 24 | − | 0 | 14 (0-91) | 9 (0-132) | 17 (0-95) | 6 (0-25) |
| | n = 11 | + | 5 (0-20) | 85 (3-259) | 13 (0-45) | 113 (2-393) | 30 (2-81) |
| CRC | n = 22 | − | 0 | 12 (0-47) | 14 (0-44) | 20 (0-83) | 14 (2-52) |
| | n = 23 | + | 2 (0-13) | 31 (5-101) | 22 (5-48) | 53 (4-151) | 24 (5-43) |
| Prostate Cancer | n = 29 | − | 0 | 10 (0-78) | 17 (1-96) | 23 (1-176) | 5 (0-25) |
| | n = 1 | + | 1 | 30 | 48 | 55 | 11 |
| Pancreatic Cancer | n = 11 | − | 0 | 15 (1-32) | 17 (3-71) | 20 (3-81) | 6 (0-21) |
| | n = 4 | + | 0 (0-1) | 31 (7-85) | 17 (6-31) | 17 (2-51) | 4 (0-9) |
| Ovarian Cancer | n = 15 | − | 0 | 13 (0-105) | 14 (1-78) | 13 (0-83) | 2 (0-12) |
| | n = 5 | + | 1 (0-3) | 19 (6-35) | 13 (6-19) | 32 (10-76) | 7 (4-13) |
| RCC | n = 3 | − | 0 | 50 (14-104) | 58 (38-85) | 56 (24-119) | 4 (0-9) |
| | n = 7 | + | 5 (1-16) | 45 (10-130) | 85 (26-164) | 71 (12-232) | 15 (3-28) |
| Melanoma | n = 7 | − | 0 | 42 (1-155) | 12 (1-31) | 35 (0-156) | 5 (0-10) |
| | n = 12 | + | 7 (0-21) | 84 (13-222) | 32 (13-70) | 89 (28-179) | 19 (6-40) |

Example 2: Screening of ICOS Antibody Agonist

Isolation of Primary Human PBMC

Fresh blood was obtained from blood donors and was diluted 1:1 with Phenol red free-10% RPMI1640 media. Diluted blood was layered on top of the density medium in a Uni-Sep Max 50 ml conical tube and centrifuge at 400×g for 20 minutes at room temperature with BREAK OFF. The resulted white mononuclear layer (buffy coat) was carefully extracted into a new 50 mL conical tube through a 100 μM cell strainer. An equal volume of Phenol red free-10% RPMI1640 media was added to the buffy coat and centrifuged at 300×g for 10 minutes at room temperature. The cell pellet was resuspended in 10 ml of red blood cell lysis solution (Sigma Aldrich) and incubated for 5 minutes at room temperature. Cells were washed once with media and centrifuged as previously described. Volume was brought to 40 ml with Phenol red free-10% RPMI1640 media and cells were counted using Vicell cell counter and viability analyzer (Beckman Coulter).

Isolation of Primary Human CD4+CD25− T Effector Cells

Human CD4+CD25 cells were further purified from PBMC via two-step magnetic beads based isolation procedure using human CD4+CD25+ Regulatory T Cell Isolation kit (Miltenyi Biotec). First, PBMC cells were incubated with biotin-antibody cocktail at 4° C. for 5 minutes and subsequently incubated anti-Biotin microbeads for 10 minutes. This step was to label the non-CD4+ T cells. Cells were then passed through a LD column in the magnetic field of a MidiMACS separator. The effluent which is the unlabeled pre-enriched CD4+ cell fraction was collected and incubated with CD25 MicroBeads at 4° C. for 15 minutes. The labelled cells were passed through a MS column in the magnetic field of a MiniMACS Separator. The flow-through containing the unlabeled CD4-CD25− T effector cells was collected for downstream activation assays.

Isolation of Primary Human CD4+ T Cells Directly from Blood

Human CD4+ T cells were isolated directly from fresh human blood using Human CD4+ T cells Enrichment Cocktail (Stem Cell Technologies). RosetteSep Human CD4+ T Cell Enrichment Cocktail (50 μL/mL) was added to whole blood and mixed well. After 20 minutes of incubation at room temperature, an equal volume of PBS+2% FBS was added with gentle mixing. The diluted sample was layered on top of the density medium and centrifuged for 20 minutes at 1200×g at room temperature with the brake off. The enriched cells from the density medium: plasma interface were carefully poured into a new conical tube. Next the red blood cells were lysed with Red Blood Cell Lying Buffer (Sigma Aldrich) and the enriched cells were washed with PBS+2% FBS twice. The CD4+ T cells were resuspended in 40 ml of with PBS+2% FBS and counted with Vi-Cell cell counter.

Experimental Protocols

Human CD4+CD25− T Effector Cell In Vitro Activation Assay—Bound Assay.

Non tissue culture treated 96 well flat bottom plates were coated with 100 μl/well of coating buffer (Biolegend) containing 1 μg/ml anti human CD3 antibody (eBioscience) and various testing antibodies overnight. On the next day, the pre-coated plates were washed three times with 10% FBS containing RPMI-1640 medium. Human CD4+CD25− T effectors cells were isolated and labelled with CFSE as described and seeded onto the plates. After incubating at 37° C. for 2.5 days, cells were harvested and analyzed by flow cytometry for proliferation and activation marker expression. Cell culture supernatants were also collected for multiplex cytokines measurement by Meso Scale Discovery (MSD).

CFSE Proliferation Assay

Cells to be labelled were resuspended in 1 ml of pre-warmed PBS at a final concentration of up to 1E7 cells/mL in a 15 ml of conical tube. One microliter of 2 mM stock CFSE solution (Life Technologies) was added directly into the cells followed by immediately vortexing to ensure uniform labelling. After incubating at room temperature for 5 minutes, the staining was quenched by adding 14 ml of ice-cold cell culture media. The labeled cells were washed three times with ice-cold media. Cells were counted and adjusted to 1E6 cells/ml in RPMI1640+10% FBS supplemented with 100 IU/ml of IL-2 (PeproTech) and seeded on anti CD3 and testing antibodies coated plates. After T cell activation, cells were harvested and washed with PBS+0.5% BSA once before proceeding to multi-color staining step for flow cytometry analysis.

Multi-Color Flow Cytometry

Activated T cells were harvested and washed with PBS. Cells were first stained with LIVE/DEAD Fixable Far Red cell viability dye (Life Technologies) following vendor's protocol. After washing the dye off, detection antibodies conjugated with different colors were incubated with cells at 4° C. for 30 minutes. Stained cells were washed once with ice cold FACS staining buffer (PBS+0.5% BSA) before running on FACS Canto or FACS Canto II flow cytometer. Cytometer performance was checked daily using Cytometer Setup & Tracking beads (BD Biosciences) and PMT voltages and area scaling were set based on unstained cells. Compensations were performed using OneComp or Ultra-Comp beads (eBioscience) that were individually stained with detection antibodies conjugated with each fluorochrome.

MSD Cytokine Analysis

IFN-γ, IL-10, IL-2 and TNF-α cytokine levels in the tissue culture supernatant were determined using MSD human V-Plex customized kit. Samples were first diluted 1:200 in Diluent2. Calibrators were also prepared in Diluent2 following kit manual. Diluted samples and calibrators were added to black MSD plate which was subsequently sealed with an adhesive plate seal and incubated at room temperature with shaking for 2 hours. After adding 25 µL of detection antibody solution which was freshly prepared in Diluent2 to each well, the plate was re-sealed and incubated at room temperature with shaking for another 2 hours. The plates were washed 3 times with 150 µL/well of PBS plus 0.05% Tween-20 before adding 150 µl/well of freshly diluted 2× read buffer and immediately read on MESO QuickPlex reader. Data were analyzed using MSD Workbench software.

Human CD4+ T Cells In Vitro Activation Assay—Bound and Soluble

Freshly isolated human CD4+ T cells were pre-stimulated on 24 well plates coated with anti-CD3 (1 µg/ml) and anti-CD28 (3 µg/ml) for 48 hours. Cells were harvested, washed and mixed with anti-CD3 DynaBeads (Life Technologies) at 1:1 ratio in AIM-V medium supplemented with 100 IU/ml of IL-2 (PeproTech). Cells/beads mixture were then seeded at 100 k per well onto 96 well flat bottom plates either non-coated (for soluble format) or coated with H2L5 hIgG4PE (for bound format). For the soluble format, H2L5 hIgG4PE was added to the wells at the time of cell seeding. After incubating at 37° C. for 3.5 days, cell culture supernatants were collected for multiplex cytokines measurement by MSD.

Soluble Human PBMC In Vitro Activation Assay

Freshly isolated human PBMCs were pre-stimulated on 24 well plates coated with anti-CD3 (1 µg/ml) and anti-CD28 (5 µg/ml) for 48 hours. CFSE stained cells were prepared and mixed with anti-CD3 DynaBeads (Life Technologies) at 1:1 ratio in AIM-V medium supplemented with 100 IU/ml of IL-2 (PeproTech). Cells/beads mixture were then seeded at 200 k per well onto 96 well plates that were pre-coated with 1 µg/ml of anti CD3 antibody. H2L5 hIgG4PE and control antibody was added directly to the wells in their soluble form. After incubating at 37° C. for 3.5 days, cell culture supernatants were collected for multiplex cytokines measurement by MSD, and cells were harvested for proliferation and marker expression analysis by flow cytometry.

Data Analysis

Flow Cytometry Data Analysis

Flow data was analyzed by FlowJo software (FlowJo LLC). Dead cells were first gated out based on LIVE/DEAD cell viability dye staining. Doublets were gated out on FSC-H: FSC-W scatter plot. The resulted live single cells were analyzed for activation marker expression within different T cell sub-populations such as CD4+ or CD8+ T cells and reported as percentage of parent population or Median Fluorescent Intensity (MFI).

CFSE Proliferation Analysis

CFSE data were also analyzed by Flowjo. After excluding the dead cells and the doublets, a "proliferated cell" gate was drawn based on non activated T cells. Any cells fall in this gate in any given sample were counted as proliferated cells. Data were reported as percentage of proliferation.

Cell Depletion Analysis by FACS

Cell depletion was analyzed by FlowJo. First, a live cells gate was determined based on LIVE/DEAD cell viability dye staining. Then the doublets were gated out as previously described. The percentages of live CD4+ or CD8+ T cell sub-population were calculated as an indicator for cell depletion.

Antibody Dose Response Curve Fitting Analysis

The dose response data were imported into GraphPad Prism software and transformed into log scale. Agonist dose response with various slope model was used to curve fit the data and generate EC50 values. The fitting formula is listed below:

$$Y=\text{Bottom}+(\text{Top}-\text{Bottom})/(1+10\hat{}((\text{Log } EC50-X)*\text{HillSlope}))$$

Results

Lead Murine Anti Human ICOS Antibodies Identification

Fourteen murine mAbs were screened for human and cynomolgus ICOS binding and agonist activity. Twelve were able to be re-cloned, sequenced, grown up and purified in sufficient amounts for functional studies. All were tested for binding characteristics using BIAcore. Two were found to be very weak/non-binders. Ten purified mAbs tested by functional "agonism" analysis. The four best agonist mAbs (designated as 422.2, 279.1, 314.8 and 88.2 in Table 5 below), based upon their ability to induce T cell proliferation and IFN-γ cytokine production across multiple healthy human donors, were selected and made as human IgG1 chimeras. The CDR sequences for 314.8, 88.2, 92.17, 145.1, and 53.3 are shown with other ICOS mAbs in PCT/EP2012/055735 (WO 2012/131004).

The heavy chain variable region for clone 88.2 is presented below as SEQ ID NO:13:

(SEQ ID NO:13)
QVQLQQPGAELVRPGASVKLSCKASGYSFTSYWINWVKQRPGQGLEWIGNI

YPSDSYTNYNQMFKDKATLTVDKSSNTAYMQLTSPTSEDSAVYYCTRWNLS

YYFDNNYYLDYWGQGTTLTVSS

The light chain variable region for clone 88.2 is presented below as SEQ ID NO:14:
QAVVTQESALTTSPGETVTLTCRSSTGAVTTSNYAN-WVQEKPDHLFTGLIGGTNNRA PGVPARFSGSLIGD-KAALTITGAQTEDEAIYFCALWYNNHLVFGGGT-KLTVL (SEQ ID NO:14)

TABLE 5

ICOS mAb Binding and Competition

| ICOS mAb Clone # | Biacore human (nM) | Biacore cyno (nM) | CD28/ CTLA4 x-reactive | ICOS-L binding inhibition | Competition against 314.8 | Competition against 121.4 |
|---|---|---|---|---|---|---|
| 53.3 | 30.4 | 19.7 | — | ++ | + | + |
| 88.2 | 31 | 23 | — | + | + | + |
| 92.17 | 27.5 | 18.8 | — | ++ | + | + |
| 145.1 | 49.5 | 43.5 | — | ++ | + | + |
| 314.8 | 17 | 9.3 | — | +++ | + | + |
| 121.4 | 15 | 58 | — | — | −/+ | −/+ |
| 202.24 | 46 | 19 | — | + | + | + |
| 279.1 | 39 | 33 | — | + | + | + |
| 293.1 | 7.6 | 10 | — | ++ | + | + |
| 422.2 | 5.7 | 4.46 | — | ++ | ++ | + |

Eight of the best ICOS binders were tested for IFN-γ production and T cell proliferation using a cell based assay in a dose escalation design against mouse IgG1 and EPR7114 controls. Based on these assays, clone designated as 422.2 was selected for humanization. See FIGS. 1 and 2.

Example 3 Antibody Humanization

Experimental Protocol(s)
Recovery of Antibody Variable Genes from mRNA and Generation of Chimeric Fc Wild-Type Antibody Total RNA was purified from the 422.2 hybridoma cell pellet, reverse transcribed to generate cDNA from which the variable gene products, approximately 400 bp, were isolated by PCR and purified by agarose gel electrophoresis.

The purified variable region fragments were cloned in to pTT5 vectors containing either the human IgG1 constant region or the human Kappa constant region and transformed into DH5a competent cells. Colonies were picked and used to inoculate L-broth containing ampicillin. Plasmid DNA was isolated from the cultures using a QuickLyse mini-prep kit. Variable heavy and light chain genes were sequenced and sequence data was aligned by informatics to identify the variable heavy and light chain gene sequences.

Cloning of Codon Optimised Chimeric 422.2 Antibodies

The mature murine variable region protein sequences were reverse translated to DNA then codon optimised. The $V_H$ and $V_L$ sequences were then modified to include the preferred five prime untranslated region and preferred cloning sites at either end. The adapted $V_H$ sequence was constructed de novo using a PCR-based strategy and overlapping oligonucleotides then grafted onto human IgG1 Fc wild type or Fc disabled hIgG1 (L235A, G237A) or hinge stabilised hIgG4 (S228P, L235E) (IgG4PE) present in pTT vectors. The adapted $V_L$ sequence was constructed de novo using a PCR-based strategy and overlapping oligonucleotides then grafted onto a kappa constant region present in a pTT5 vector.

The resulting pTT plasmids were used in HEK transfections to produce the chimeric antibodies
Humanization of the Variable Domains of 422.2

Human variable (V) gene templates were chosen for humanization of 422.2 by searching appropriate in-house human germline heavy and light chain databases with CDR-masked 422.2 V regions using BLASTP. IGHV1-69 and IGKV3-11 were chosen from the top BLASTP hits as the V gene framework templates for 422.2 humanization. IGHJ6 and IGKJ2 human germline Joining (J) genes were chosen for humanization of 422.2.

Residue differences between the chosen human germline genes and the 422.2 sequence were identified to aid in the selection of back-mutations (mutations made to change the specific human framework residue to the murine residue). Six humanized VH variants and six humanized VL variants were designed, codon optimised and then modified to include preferred 5' and 3' extensions. The adapted variable region sequences were constructed de novo using a PCR-based strategy and overlapping oligonucleotides then respectively cloned into pTT vectors.

The resulting pTT plasmids were used in HEK transfections to produce the humanized antibodies. HEK2936E suspension cells were counted and diluted to $1.5 \times 10^6$ cells/mL to $2 \times 10^6$ cells/mL using Freestyle expression medium 293 supplemented with 0.05% Geneticin and for some experiments supplemented with 1% pluronic F68. DNA and transfection reagent (Gemini or 293-Fectin) were added to OptiMEM and gently homogenised prior to incubation for 20 to 30 minutes at room temperature. The DNA-lipid complexes were then combined with the cell suspensions and the transfected cells were incubated at 37° C., 5% CO2, 125 rpm. For some transfections, a tryptone feed (Freestyle expression medium 293 supplemented with 1% pluronic F68 and 20% w/v casein tryptone) was added to each transfection 24 to 48 hours after transfection. Transfected cell suspensions were incubated for 5 to 8 days until viable cells dropped below 60% then centrifuged (construct dependent). Supernatants were harvested and filtered.

Antibodies were purified by passing supernatants through a 1 mL HiTrap Protein A HP column to enable antibody capture, washing the column through with 10 mL of PBS and eluting with 5 mL of IgG Elute (Pierce, 21009). Purified protein was buffer exchanged into PBS using the Millipore Centricon® Centrifugal Filter Units (30K cut-off) and quantified on the Nandrop spectrophotometer.

Results
Constructed Expression Plasmids

The murine antibody variable gene sequences of hybridoma clone 422.2 were successfully recovered and the sequences are shown below as SEQ ID NOs: 19 and 20, respectively as well as in FIG. 8.

422 HC (SEQ ID NO:19)
QVQLQQSGPELVRPGESVKISCMGSGYTFTDYAMHWVKQSHAKSLEWIGLI

SIYSDHTNYNQKFQGKATMTVDKSSSTAYMELARLTSEDSAIYYCGRNNYG

NYGWYFDVWGAGTTVTVSS

422 LC (SEQ ID NO: 20)
ENVLTQSPAIMSASPGEKVTMTCSASSSVSYMHWYQQKSITSPKLWIYDTS

KLASGVPGRFSGSGSGNSYSLTISSMEAEDVATYYCFQGSGYPYTFGGGTK

LEIKR

Cloning the recovered variable regions into selected pTT5 vectors resulted in generation of plasmids encoding the chimeric light chain sequence of 422.2 and the chimeric heavy chain sequences on hIgG1 Fc wild type, hIgG1 Fc disabled (L235A/G237A, EU numbering) or a hIgG4 PE (S228P/L235E, EU numbering). The chimeric antibodies were used to confirm functionality of the cloned mouse V-regions and to identify the most suitable isotype.

Construction of pTT mammalian expression plasmids encoding the heavy and light chains of the various humanized variants of 422.2 was carried out successfully.
Expression, Purification and Identification of H2L5 hIgG4PE The mature protein sequences of H2L5 hIgG4PE have been included with additional labeling in FIG. 9. The DNA sequences of the coding regions of H2L5 hIgG4PE heavy and light chains have been included in FIGS. 10 and 11.

Example 4: Functional Analysis of H2L5

Fc Receptor Binding

Humanized antibody H2L5 was modified from a human IgG1 isotype to a modified human IgG4 isotype incorporating mutations S228P, L235E (EU numbering) to prevent antigen binding fragment (Fab) arm exchange. Human IgG4PE was selected over human IgG1 as it diminishes binding of the mAb to activating Fcγ receptors and C1q, therefore, reducing the potential of the mAb to induce depletion of ICOS positive cells by antibody-dependent cytotoxicity (ADCC) or complement dependent cytotoxicity (CDC). In addition, human IgG4PE (S228P, L235E) retains binding to FcγRIIb (inhibitory Fcγ receptor). Interaction with FcγRIIb may be critical for the agonistic activity of ICOS antibodies by enabling antibody cross-linking. Interaction with FcγRIIb has been shown to be critical for the agonistic activity of other immunomodulatory antibodies targeting TNF-α family receptors as well as CD28 (Bartholomaeus P et al., "Cell contact-dependent priming and Fc interaction with CD32+ immune cells contribute to the TGN1412-triggered cytokine response." J. Immunol., 192 (5); 2091-8 (2014)).

It was further shown that human IgG4PE diminishes binding of the mAb to activating Fcγ receptors (FcγRI, FcγRIIa and FcγRIIIa) and C1q, therefore reducing the potential of the mAb to induce depletion of ICOS positive cells by antibody-dependent cytotoxicity (ADCC) or complement dependent cytotoxicity (CDC). In addition, human IgG4PE (S228P, L235E) retains binding to FcγRIIb (inhibitory Fcγ receptor) (Table 6).
Table 6 below displays representative binding affinities to human Fcγ receptors of the lead H2L5 as either a hIgG1 or a hIgG4PE antibody.

TABLE 6

Representative Affinities of Lead Humanized ICOS antibody, as either a hIgG1 or a hIgG4PE, to human Fcγreceptors

| Antibodies | FcγR I KD (nM) | Fcγ IIa H131 KD (nM) | Fcγ IIa R131 KD (nM) | FcγR IIb KD (nM) | FcγR IIIa V158 KD (nM) | FcγR IIIa F158 KD (nM) |
|---|---|---|---|---|---|---|
| 422 H2L5 IgG1 WT | 60.8 | 405 | 662 | 1340 | 281 | 862 |
| 422 H2L5 hIgG4PE (H2L5 IgG4PE) | 645 | NB | 2500 | 1470 | NB | NB |

NB = no binding.

Experimental Protocol
Functional Evaluation of 422.2 Humanized Variants

To humanize the four candidate ICOS agonist antibodies, mouse-human chimeras, which are fusions of mouse V region and human IgG1 Fc portion, were generated. These four chimera antibodies were tested in human whole PBMC activation assay as plate bound form. Anti-ICOS chimera 422.2 showed the best agonistic activity in the bound PBMC activation assay. Combined with binding data and biophysical properties, 422.2 clone was chosen for humanization. Four humanized 422.2 variants were selected based on ICOS binding and biophysical characteristics (422.2 H2L0, H2L5, H5L0 and H5L5) and were tested in bound human PBMC activation assays. The H2L5 variant demonstrated comparable or better T cell activation as measured by cytokine production relative to other variants (FIG. 3).

The heavy chain ($V_H$) variable region and mature heavy chain for the H5 variant are presented below as SEQ ID NOs:15 and 16, respectively.
H5 VH (SEQ ID NO:15)
QVQLVQSGAEVKKPGSSVKVSCKASGYTFTDYAMHWVRQAPGQGLEWIGLI

SIYSDHTNYNQKEQGRATMTVDKSTSTAYMELSSURSEDTAVYYCGRNNYG

NYGWYEDVWGQGTTVTVSS

Mature H5 Heavy Chain (SEQ ID NO: 16)
QVQLVQSGAEVKKPGSSVKVSCKASGYTFT<u>DYAMH</u>WVRQAPGQGLEWIG<u>LI</u>

<u>SIYSDHTNYNQKFQG</u>RATMTVDKSTSTAYMELSSLRSEDTAVYYCGR<u>NNYG</u>

<u>NYGWYFDV</u>WGQGTTVTVSSASTKGPSVFPLAPSSKSTSGGTAALGCLVKDY

FPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

The light chain ($V_L$) variable region and mature light chain for the L0 variant are presented below as SEQ ID NOs:17 and 18, respectively.
L0 VL (SEQ ID NO: 17)
EIVLTQSPATLSLSPGERATLSCSASSSVSYMHWYQQKPGQAPRLLIYDTS

KLASGIPARFSGSGSGTDFTLTISSLEPEDFAVYYCFQGSGYPYTFGQGTK

LEIK

Mature L0 Light Chain (SEQ ID NO: 18)
EIVLTQSPATLSLSPGERATLSCSASSSVSYMHWYQQKPGQAPRLLIYDTS

KLASGIPARFSGSGSGTDFTLTISSLEPEDFAVYYCFQGSGYPYTFGQGTK

LEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPV

TKSFNRGEC

Selection of IgG4[PE] as the Isotype

The 422 H2L5 IgG1 was subsequently tested in various whole PBMC activation assays in soluble form. This soluble format is likely to be more relevant to the in vivo condition as the whole PBMC assays contain lymphocytes, monocytes and other immune cells in the same well. However, 422 H2L5 IgG1 mAb consistently showed decreased viability of T cell populations which is reminiscent of T cell depletion. This result was observed to different degrees in 11 healthy donors which were tested and was more prominent in CD4+ T cells than in CD8+ T cells. In contrast, the 422 H2L5 antibody did not show a significant decrease in T cell viability when expressed as either an IgG4[PE] or Fc-disabled isotype, suggesting that the decreased viability may have been due to FcγR-mediated antibody-dependent cellular cytotoxicity (ADCC) (FIG. 4).

Dose Response of H2L5 hIgG4PE in CD4+ T Cell Activation Assay

To quantify the T cell activation effects of H2L5 hIgG4PE, human primary CD4+ T cells were first pre-stimulated by plate bound anti-CD3 (1 µg/ml)/anti-CD28 (3 µg/ml) for 48 hours to induce levels of ICOS receptor on the surface of T effector cell populations, followed by re-stimulation with anti CD3 DynaBeads and H2L5 hIgG4PE. A 10-point dose response curve was generated by treating the pre-simulated CD4+ T cells with serial concentrations of bound or soluble H2L5 hIgG4PE in the presence of anti-CD3 DynaBeads. Results showed that both bound and soluble H2L5 hIgG4PE increased IFN-γ and TNF-α cytokines productions in a dose dependent manner in two separate healthy human donors (FIG. 5). A dose-response curve fitting analysis was performed to generate EC50 values. Interestingly, H2L5 hIgG4PE treatment resulted in a significantly greater magnitude of cytokine induction when the antibody was plate-fixed as opposed to being added as a soluble protein to the supernatant of the T cell cultures.

Functional Testing of H2L5 hIgG4PE in Soluble Human PBMC Activation Assay

In order to test the function of H2L5 hIgG4PE in whole human PBMC ex vivo culture, PBMC from healthy human donors were prepared with plate bound anti-CD3 and anti-CD28 for 48 hours, followed by soluble H2L5 hIgG4PE treatment in the presence of anti CD3 dynabeads (bead:cell=1:1 ratio) for 3.5 days. Cytokine production and T cell Granzyme B expression was examined as functional readouts for T cell function. The results from 3 donors were summarized in FIG. 6, which provide evidence to suggest that H2L5 hIgG4PE induces proliferation, cytokine production and increased cytotoxic potential in activated PBMCs from healthy human donors (FIG. 6).

ICOS mAb Activity Against Pre-Stimulated Human PBMCs

The activity of H2L5 hIgG4PE was evaluated in a PBMC pre-stimulation assay in which the PBMC were pre-stimulated by plate bound anti-CD3 (clone OKT3, 1 µg/ml) and anti CD28 (clone CD28.2, 3 µg/ml) for 48 hours. Next, in order to identify the optimal pre-stimulation conditions, human CD3 Dynabeads and CD3/CD28 Dynabeads (ThermoFisher) at different bead to cell ratios were used to pre-stimulate PBMCs. After 48 hr pre-stimulation, cells were harvested and beads magnetically removed before re-stimulation with anti CD3 Dynabeads (bead to cell ratio=1:1) in the presence or absence of soluble ICOS mAb. H2L5 hIgG4PE ICOS agonist mAb resulted in induction of IFNγ as compared to isotype control in all pre-stimulation conditions tested; however, the magnitude of IFNγ production inversely correlated with strength of the pre-stimulation.

Example 5—T Cell Activation Markers

Methods

Concentration-dependent changes in functional endpoints were assessed by treating healthy human PBMCs with immobilized H2L5 hIgG4PE at concentrations ranging from 0.1 µg/mL to 100 µg/mL concurrently with anti-CD3 antibody treatment at 0.6 µg/mL. Changes in expression of T cell surface activation markers CD69, OX40 and CD25 were evaluated by flow cytometry and considered a measure of T cell activation. Proliferation of T cells was measured by the changes in Ki67 nuclear staining. Change in levels of various Th1, Th2 and Th17 cytokines were evaluated on the MSD platform in response to H2L5 hIgG4PE treatment in the presence of CD3 engagement. The 24- and 48-hours post treatment timepoints were selected to ensure the capture of both early cytokine changes as well as proliferation changes which are predominantly noticed at later time points.

Experimental Preparation(s)

Isolation of Human Peripheral Blood Mononuclear Cells (PBMCs)

Whole blood was collected from healthy donors with syringes coated with liquid sodium heparin (Sagent 10 IU/mL final concentration) and subsequently diluted 1:1 with phosphate buffered saline (PBS). Diluted blood (35 mL) was layered on top of 15 mL Ficoll density gradient medium (GE Healthcare) and centrifuged at 1200×g for 20 minutes at room temperature (RT) without brakes. The white mononucleated cell layer was carefully transferred into a new 50 ml tube. An equal volume of PBS was added to the tube and centrifuged at 400×g for 5 minutes at RT. PBMC were washed once with PBS and centrifuged as previously described. PBMC were resuspended in 50 mL AIM-V media Cells were counted using a Vi-Cell cell counter and viability analyzer (BeckmanCoulter).

Antibody Coating

Anti-human CD3 antibody was diluted in coating buffer to a final concentration of 0.6 µg/mL. 100 µL diluted antibody was coated on 96-well, flat-bottom plate overnight at 4° C. Next day, stock solutions of 10.1 mg H2L5 hIgG4PE and 7.9 mg anti-RSV IgG4 PE isotype control antibody were 1:2 serially diluted in coating buffer to give final antibody concentrations ranging from 100 to 0.1 µg/mL. 100 µL diluted antibodies were coated on anti-CD3 coated plate for 4 hours at room temperature.

Experimental Protocol(s)

Human PBMC Activation Assay

H2L5 hIgG4PE was tested in a human PBMC activation assay where TCR engagement via anti-CD3 antibody and ICOS co-stimulation with H2L5 hIgG4PE occurred concurrently, and the activation effects were monitored at 24 and 48 hours post activation. This experiment was repeated four times (n=4) with blood from four different donors. Two hundred (200) µL PBMCs (1×10⁶ cells/mL) in AIM-V medium were added into anti-CD3 antibody-coated wells with various concentrations of H2L5 hIgG4PE or IgG4 isotype control. Three technical replicates were included for each assay condition. PBMCs were cultured at 37° C. and 5% $CO_2$ for various times as indicated above. Supernatants were collected at 24- and 48-hour time points and then stored at −80° C. for analysis of secreted cytokines on the MSD platform. Cells were transferred into 96-deep well plate at both 24 and 48 hours and washed twice with 1 mL FACS Staining Buffer stained with fluorophore-conjugated antibodies or isotype controls.

Cell Surface Staining

Cells were first stained with 100 µL of fixable viability dye eFluor 506 pre-diluted 1:1000 in PBS for 30 minutes in the dark at 4° C. Cells were washed and then incubated with detection antibodies to cell surface markers conjugated to different fluorophores on ice for 30 minutes. Post-staining with cell surface antibodies, samples not to be stained for internalization markers were washed once with ice cold FACS Staining Buffer before running on FACS Canto II flow cytometer.

Cytometer performance was appropriately evaluated daily using the Cytometer Set-up and Tracking beads. Compensations were performed using AbC anti-mouse Bead kit that were individually stained with detection antibodies conjugated with each fluorochrome. Samples were run and data acquired after proper compensation set up was ascertained with a mix of beads mentioned above.

Intracellular Staining for Foxp3 and Ki67

Following the cell surface staining, the cells were fixed and permeabilized for staining for intracellular markers. Using the Transcription Factor Buffer set, the Fixation/Permeabilization Buffer was prepared by diluting this 1:3 in Diluent Buffer. The Perm Wash Buffer was prepared by diluting the 5× Perm/Wash Buffer stock in deionized water. One (1) mL of Fix/Perm Buffer was added to each sample, and the plates were immediately vortexed on the shaker. The plates were incubated in the dark at 4° C. for 45 minutes. Following centrifugation, 1 mL of Perm/Wash Buffer was added, and the plates were mixed and centrifuged for a total of two washes. The internalization cocktail was prepared with marker antibodies. 100 µL of the internalization antibodies were added to the appropriate samples, and the plates were incubated in the dark at 4° C. for 30 minutes. Samples were washed twice with 1 mL of Perm Wash Buffer, resuspended in 250 µL of flow buffer and run on FACS Canto II flow cytometer.

Human Special Order 9-plex Cytokine Assay

Cytokine levels were measured using the MSD Human Special Order 9-Plex kit. Samples and calibrators were diluted in Diluent 43. Samples were diluted 1:10 for the 9-plex assay and 1:200 for the IFNγ assay described in 0.250 µL of the diluent was added to each of two calibrator panels. After vortexing, the calibrators were incubated on ice for at least 5 minutes. Two hundred (200) µL of each calibrator panel was added to 400 µL of diluent to make the top concentration of calibrator, and a 1:4 serial dilution was used to prepare the 6 additional calibrator dilutions. Diluent 43 was used as the plate background. 50 µL of diluted samples (in triplicate) and calibrators (in duplicate) were added to the MSD plate. Plates were sealed and incubated at RT with shaking for 2 hours. Plates were washed 3 times with 150 µL of diluted MSD Wash Buffer from the kit. For each plate, detection antibody solution was prepared by combining 60 µL of each of the 9 detection antibodies brought up to 3 mL with Diluent 3. Following the addition of 25 µL of detection antibody solution, the plates were sealed and incubated at room temperature, in the dark, with shaking for 2 hours. Plates were washed as above. 150 µL of 2× Read Buffer was added to the plates, and they were read on the QuickPlex.

Human IFNγ Cytokine Assay

Samples and calibrators were diluted in Diluent 2. 1 mL of the diluent was added to the calibrator. After vortexing, the calibrator was incubated on ice for 5 minutes. This is Calibrator 1. A 1:4 serial dilution was used to prepare the 6 additional calibrator dilutions. Diluent 2 was used as the plate background. Fifty (50) µL of diluted samples (in tripicate) and calibrators (in duplicate) were added to the MSD plate. Plates were sealed and incubated at RT with shaking for 2 hours. Plates were washed 3 times with 150 µL of diluted MSD Wash Buffer from the kit. Detection antibody solution prepared in Diluent 3. For each plate, 60 µL of each of the detection antibody was added to the diluent for a total of 3 mL of detection reagent. Following the addition of 25 µL of detection antibodies, the plates were sealed and incubated at room temperature, in the dark, with shaking for 2 hours. Plates were washed 3 times. Read Buffer was added to the plates and they were read on the QuickPlex.

Data Analysis

Cytokine and Flow Cytometry Data Analysis

Results of MSD cytokine assay were analyzed using MSD Discovery Workbench software, version 4.0 (Meso-Scale), Microsoft Excel, and Graphpad Prism. Flow cytometry data were analyzed by DIVA, and numbers were plotted in GraphPad Prism software.

Antibody Dose-Response Curve Fitting Analysis

The dose response data were imported into GraphPad Prism software and transformed into log scale. Agonist dose response with various slope model was used to analyze the data and generate EC50 values. The fitting formula is listed below:

$$Y=\text{Bottom}+(\text{Top}-\text{Bottom})/(1+10^{((\text{Log }EC50-X)*\text{HillSlope})})$$

Statistical Analyses

Differences between H2L5 hIgG4PE and isotype antibody control values in the proliferation study were analyzed for a statistical significance by two-paired Student's t test.

Results

Evaluation of Cytokine Changes with H2L5 hIgG4PE

Treating PBMCs with immobilized H2L5 hIgG4PE in the presence of anti-CD3 induced the secretion, to different degrees, of Th1 cytokines such as IFNγ, TNFα, the Th2 cytokines, IL-6 and IL-10, as well as the Th17 cytokine IL-17a in a concentration-dependent manner. Other cytokines measured such as IL-4, IL-5 and IL-13 also showed a lesser extent of concentration-dependent response to H2L5 hIgG4PE stimulation. The results from four separate donors are summarized in Table 7.

Functional Evaluation of H2L5 hIgG4PE Activity on Cell Surface Markers of T Cell Activation by Flow Cytometry H2L5 hIgG4PE treatment with concurrent CD3 stimulation in unactivated human PBMC (n=4 donors) induced significant changes in T cell activation markers (Table 7 and 8)). Robust increases in CD25 and OX40 positive CD4 and CD8 T cells were observed in H2L5 hIgG4PE treated samples when compared to the human IgG4 isotype control samples. The percent of CD69 positive CD4 and CD8 T cells were also increased at 24- and 48-hour time point in a concentration-dependent manner.

Characterization of the Effect of H2L5 hIgG4PE on T Cell Proliferation

Immobilized H2L5 hIgG4PE treatment with concurrent CD3 activation resulted in a concentration-dependent increase in both CD4 and CD8 T cell proliferation (n=6 donors) as measured by intracellular Ki67 staining (Table 8). H2L5 hIgG4PE also increased CD4+CD25+ Foxp3+ regulatory T cell proliferation in a concentration dependent manner but to a lesser extent than what was observed with total CD4 and CD8 T cells. The enhancement of T cell proliferation by H2L5 hIgG4PE was only observed at the 48 hour time point. The increased proliferation of the regulatory T cells was not significant whereas the concentration-dependent increase in proliferating CD4+ cells (p<0.05 for concentrations greater than 0.4 µg/mL H2L5 hIgG4PE) and CD8+ T cells (p<0.05 for concentrations between 0.2 and 1.6 µg/mL) was significant (see Table 7).

TABLE 7

EC50 values (itg/mL) from all functional endpoints for H2L5 hIgG4PE in human PBMC activation assay.

|  | Donor_1136F50 | | Donor_185M45 | | Donor_1124F36 | | Donor_1149M52 | |
| --- | --- | --- | --- | --- | --- | --- | --- | --- |
|  | 24 hr | 48 hr | 24 hr | 48 hr | 24 hr | 48 hr | 24 hr | 48 hr |
| IL-10 | 1.7 | 1.3 | 0.7 | 0.8 | 0.7 | 0.6 | 0.5 | 0.6 |
| IFN-γ | 0.4 | 1.5 | 0.3 | 0.7 | 0.3 | 0.5 | 0.2 | 0.6 |
| IL-17a | 1.4 | 1.6 | 0.8 | 1.1 | 0.6 | 0.8 | 0.7 | 1.0 |
| IL-6 | 0.7 | 1.1 | 0.7 | 0.8 | NA | NA | 0.2 | 0.3 |
| TNF-α | NA | 0.3 | NA | 0.5 | NA | 0.3 | NA | 0.2 |
| C D4+CD69+ | 0.5 | 0.4 | 0.8 | NA | 1.1 | 1.1 | 0.5 | 0.4 |
| CD4+CD25+ | 0.3 | 0.6 | 2.4 | 0.5 | 0.6 | 0.6 | 0.6 | 0.4 |
| CD4+OX40+ | 0.2 | 0.4 | 1.6 | NA | 0.6 | 1.2 | 0.6 | 0.4 |
| CD8+CD69+ | 0.5 | 0.6 | 1.2 | 0.5 | 0.8 | 1.1 | 0.6 | 0.4 |
| CD8+CD25+ | 0.4 | 0.7 | 2 | 0.5 | 0.6 | 0.5 | 1.0 | 0.4 |
| CD8+OX40+ | 0.3 | 0.5 | 1.6 | NA | 2.4 | 0.5 | 1.5 | 0.3 |
| CD4+Ki67+ | NT | NT | NA | 0.6 | NA | 0.8 | NA | 0.5 |
| CD8+Ki67+ | NT | NT | NA | 0.4 | NA | 0.7 | NA | 0.3 |

NA = no analysis (EC50 values not accurate due to poor curve fitting).
NT = no tested.

TABLE 8

Percent of CD25, Foxp3 and Ki67 positive CD4 or CD8 T cells in human PBMCs after stimulation with H2L5 hIgG4PE in the presence of anti-CD3 for 48 hours

| | Antibody concentration μg/ml | H2LA hIgG4PE (% of CD4 or CD8 T cells) | | | Isotype Control (% of CD4 or CD8 T cells) | | | TTEST (p value) |
| --- | --- | --- | --- | --- | --- | --- | --- | --- |
| | | Donor 185M45 | Donor 1124F36 | Donor 1149M52 | Donor 185M45 | Donor 1124F36 | Donor 1149M52 | |
| % Treg CD4 T cells | 0 | 10.2 | 3.8 | 6.1 | 10.2 | 3.8 | 6.1 | 0.415 |
| | 0.1 | 12.4 | 4.2 | 7.6 | 8.6 | 3.6 | 6.6 | 0.220 |
| | 0.2 | 11.8 | 4.5 | 9.8 | 8.5 | 3.2 | 7.1 | 0.054 |
| | 0.4 | 14.3 | 5.2 | 11.3 | 8.6 | 3.4 | 7.4 | 0.076 |
| | 0.8 | 18.6 | 6.9 | 14.3 | 8.4 | 3.4 | 7.3 | 0.069 |
| | 1.6 | 21.4 | 7.5 | 15.9 | 7.7 | 3.8 | 7.2 | 0.095 |
| | 3.1 | 20.8 | 7.9 | 15.0 | 10.4 | 3.9 | 7.1 | 0.058 |
| | 6.3 | 18.7 | 8.3 | 14.7 | 10.3 | 3.6 | 8.3 | 0.026 |
| | 12.5 | 20.2 | 7.6 | 15.1 | 9.6 | 4.0 | 8.1 | 0.072 |
| | 25 | 19.5 | 7.6 | 13.9 | 11.5 | 5.1 | 8.3 | 0.079 |
| | 50 | 20.0 | 7.9 | 13.3 | 9.6 | 5.0 | 9.7 | 0.143 |
| | 100 | 18.7 | 7.9 | 13.3 | 11.5 | 5.6 | 8.8 | 0.080 |
| % Ki67 + CD4 T cells | 0 | 7.2 | 1.2 | 2.3 | 7.2 | 1.2 | 2.3 | 0.693 |
| | 0.1 | 9.6 | 1.5 | 2.9 | 6.1 | 0.9 | 2.1 | 0.219 |
| | 0.2 | 9.0 | 2.1 | 4.4 | 5.0 | 0.9 | 2.4 | 0.098 |
| | 0.4 | 11.9 | 3.9 | 7.5 | 6.8 | 1.0 | 2.7 | 0.025 |
| | 0.8 | 18.2 | 7.1 | 12.4 | 7.6 | 1.3 | 2.5 | 0.028 |
| | 1.6 | 19.5 | 8.9 | 15.9 | 5.4 | 0.8 | 3.2 | 0.024 |
| | 3.1 | 21.1 | 10.7 | 14.4 | 9.1 | 1.2 | 2.9 | 0.005 |
| | 6.3 | 18.7 | 12.6 | 17.1 | 8.1 | 1.1 | 3.2 | 0.007 |
| | 12.5 | 22.2 | 12.2 | 16.5 | 7.4 | 1.5 | 3.4 | 0.008 |
| | 25 | 20.7 | 11.6 | 16.1 | 9.3 | 1.7 | 5.2 | 0.002 |
| | 50 | 21.2 | 12.8 | 14.3 | 7.5 | 2.4 | 7.3 | 0.034 |
| | 100 | 21.8 | 12.0 | 14.0 | 9.4 | 2.8 | 4.7 | 0.010 |
| % Ki67 + CD8 T cells | 0 | 11.0 | 4.4 | 2.7 | 11.0 | 4.4 | 2.7 | 0.841 |
| | 0.1 | 15.2 | 8.3 | 4.8 | 9.6 | 5.3 | 2.3 | 0.061 |
| | 0.2 | 13.5 | 10.9 | 7.8 | 8.2 | 3.8 | 2.9 | 0.014 |
| | 0.4 | 17.4 | 14.4 | 11.3 | 10.1 | 3.4 | 4.3 | 0.023 |
| | 0.8 | 20.7 | 19.6 | 13.8 | 14.2 | 4.5 | 2.0 | 0.047 |
| | 1.6 | 22.2 | 22.8 | 16.1 | 10.7 | 4.0 | 3.7 | 0.025 |
| | 3.1 | 21.8 | 26.7 | 13.6 | 14.5 | 4.4 | 3.0 | 0.099 |
| | 6.3 | 20.2 | 29.8 | 16.0 | 10.8 | 3.3 | 5.0 | 0.103 |
| | 12.5 | 21.7 | 29.6 | 15.6 | 10.7 | 4.1 | 3.4 | 0.074 |
| | 25 | 20.0 | 28.7 | 14.6 | 10.4 | 6.1 | 5.0 | 0.084 |
| | 50 | 19.0 | 31.4 | 13.5 | 7.6 | 5.1 | 5.5 | 0.114 |
| | 100 | 19.2 | 27.4 | 13.4 | 7.9 | 7.1 | 3.5 | 0.051 |
| % Ki67 + T reg cells | 0 | 29.7 | 10.2 | 11.3 | 29.7 | 10.2 | 11.3 | 0.920 |
| | 0.1 | 32.8 | 12.5 | 14.4 | 32.4 | 10.0 | 12.3 | 0.127 |
| | 0.2 | 33.0 | 14.8 | 19.0 | 30.3 | 8.3 | 13.4 | 0.051 |
| | 0.4 | 33.6 | 22.2 | 22.2 | 28.4 | 10.8 | 14.1 | 0.044 |
| | 0.8 | 37.0 | 26.3 | 26.3 | 36.7 | 8.5 | 14.4 | 0.191 |

TABLE 8-continued

Percent of CD25, Foxp3 and Ki67 positive CD4 or CD8 T cells in human PBMCs after stimulation with H2L5 hIgG4PE in the presence of anti-CD3 for 48 hours

| Antibody concentration µg/ml | H2LA hIgG4PE (% of CD4 or CD8 T cells) | | | Isotype Control (% of CD4 or CD8 T cells) | | | TTEST (p value) |
|---|---|---|---|---|---|---|---|
| | Donor 185M45 | Donor 1124F36 | Donor 1149M52 | Donor 185M45 | Donor 1124F36 | Donor 1149M52 | |
| 1.6 | 35.0 | 27.7 | 28.4 | 26.8 | 7.7 | 16.3 | 0.061 |
| 3.1 | 38.3 | 30.2 | 27.2 | 33.9 | 9.6 | 17.4 | 0.135 |
| 6.3 | 33.9 | 32.5 | 26.1 | 36.7 | 8.7 | 16.5 | 0.315 |
| 12.5 | 37.3 | 36.8 | 26.2 | 31.2 | 15.1 | 17.2 | 0.125 |
| 25 | 36.3 | 33.0 | 28.6 | 33.3 | 13.7 | 28.1 | 0.326 |
| 50 | 37.7 | 33.6 | 24.2 | 32.9 | 21.1 | 29.5 | 0.518 |
| 100 | 40.1 | 35.8 | 28.6 | 36.3 | 21.5 | 26.4 | 0.216 |

Discussion

It is well established that ICOS is important for T cell activation and induction of both Th1 and Th2 cytokines. In this study, the in vitro activity of H2L5 hIgG4PE (anti-ICOS agonist antibody), was demonstrated with various measures of T cell activation and cytokine induction. All measured T cell activation markers, CD25 (IL-2 receptor alpha-chain), CD69 (early activation marker) and OX-40 (co-stimulatory marker) were upregulated upon treatment with H2L5 hIgG4PE in conjunction with CD3 stimulation. Among the activation markers monitored, the percent of T cells expressing CD69 and OX40 were strongly increased by H2L5 hIgG4PE treatment. CD69 is an early activation marker and hence the effects are predominant in the 24-hour samples. CD25, another important T cell activation marker, was increased upon treatment with H2L5 hIgG4PE at both time points, suggesting that H2L5 hIgG4PE plays an important role in maintaining activation of T cells. Ki67 is a nuclear protein associated with cell proliferation. Flow cytometry data with Ki67 intracellular staining indicated that immobilized H2L5 hIgG4PE significantly enhanced both CD4 and CD8 T cell proliferation in the context of TCR engagement. Though proliferation of regulatory T cells was also increased by H2L5 hIgG4PE, the changes were not statistically significant.

Human Th17 cells are a key player in the regulation of anti-tumor immunity [Nunez, S., et al., T helper type 17 cells contribute to anti-tumour immunity and promote the recruitment of T helper type 1 cells to the tumour. *Immunology* 2013; 139: 61-71]. Studies show ICOS is involved in human Th17 development and function [Kimura, A., et al., Regulator of Treg/Th17 balance. *Eur. J. Immunol.* 2010; 40: 1830-1835; Paulos C M et al. The inducible costimulator (ICOS) is critical for the development of human Th17 cells. *Sci Transl Med.* (2010) 2(55); 55ra78; Nelson, M. H., et al. The inducible costimulator augments Tc17 cell responses to self and tumor tissue. *J Immunol*, 2015; 194: 1737-1747]. In the current functional evaluation of H2L5 hIgG4PE, a majority of cytokines related to inflammatory and immune responses were measured in the supernatant of cell cultures after anti-CD3 and H2L5 hIgG4PE stimulation. H2L5 hIgG4PE strongly induces secretion of Th1 cytokines, IFN-γ and TNF-α and Th17 cytokine, IL-17a, in human PBMCs, suggesting that H2L5 hIgG4PE has the potential to play an important role in anti-tumor responses. IL-6, together with TGF-β, is an important cytokine for induction of the Th17 cell development from naive T cells. In contrast, IL-6 inhibits Treg differentiation induced by TGF-β [Kimura, A., 2010; Korn, T., et al., IL-6 controls Th17 immunity in vivo by inhibiting the conversion of conventional T cells into Foxp3+ regulatory T cells. PNAS, 2008; 105: 18460-18465]. In this study, H2L5 hIgG4PE was found to increase the secretion of IL-6 which may further enhance Th17 cell development. Agonist antibodies of T cell receptors such as CD28 and TNF receptor family members have been shown to produce a bell shaped dose response curve [White, A. L., et al., Conformation of the Human Immunoglobulin G2 Hinge Imparts Superagonistic Properties to Immunostimulatory Anticancer Antibodies. *Cancer Cell*, 2015, 27: 138-148; Luhder, F., et al, Topological Requirements and Signaling Properties of T Cell-activating, Anti-CD28 Antibody Superagonists. *J Exp. Med.* 2003: 955-966; Stebbings, R., et al., "Cytokine Storm" in the Phase I Trial of Monoclonal Antibody TGN1412: Better Understanding the Causes to Improve PreClinical Testing of Immunotherapeutics *J Immunol.*, 2007, 179: 3325-3331; Rogers P R and Croft M, CD28, Ox-40, LFA-1, and CD4 Modulation of Th1/Th2 Differentiation Is Directly Dependent on the Dose of Antigen. *J Immunol* 2000 164: 2955-2963; doi: 10.4049/jimmunol.164.6.2955]. H2L5 hIgG4PE also demonstrates a similar hyperbolic functional response curve. This information is an important component in ascertaining the best dose range of the antibody to be used for optimal pharmacodynamic response.

Overall, H2L5 hIgG4PE, in conjunction with CD3 stimulation, was shown to enhance T cell activation, proliferation and proinflammatory cytokine induction in line with its role as a potent activator of a T cell co-stimulatory receptor.

Example 6: Binding of Anti-ICOS Antibodies

The humanization protocol (Example 3) produced 36 heavy and light chain variants which were screened for binding to human and cynomolgus ICOS whilst also ensuring that they did not bind to human CD28 or CTLA-4. The H2L5 variant was identified as the having high affinity for human and cynomolgus ICOS (1.34 and 0.95 nM respectively) whilst containing the minimum number of back mutations.

Changing the isotype of 422 H2L5 from IgG1 to IgG4PE does not affect the antigen binding of the antibody as H2L5 hIgG4PE has an affinity of 1.3 nM to human ICOS. Concentration based inhibition of ICOS/ICOS-L binding by H2L5 hIgG4PE is shown in FIG. 7.

Experimental Protocols
Binding of H2L5 hIgG4PE to Human ICOS

The binding kinetics affinity of the humanized H2L5 hIgG4PE antibody was determined used the BIAcore T200 Anti-human IgG on Fc2 of a CM5 chip Anti-ICOS H2L5 hIgG4PE captured on the surface. Anti-human IgG surface blocked with 0.1 mg/mL hIgG1 control to prevent non-specific binding of rabbit Fc. Human and cyno ICOS (rabbit Fc) passed over the captured antibodies at 256 nM, 64 nM, 16 nM, 4 nM and 1 nM. Buffer alone was used to double reference binding curves. MgCl$_2$ was used to regenerate surface. Run carried out at 25° C. Data fitted to 1:1 model using T200 evaluation software. Antibody concentration: 2.5 μg/mL Results
Binding of H2L5 hIgG4PE to Human and Cynomolgus ICOS The binding kinetics affinity of the humanized H2L5 hIgG4PE antibody was determined using the BIAcore T200.

The ICOS binding data was fitted to a 1:1 kinetics model using the T200 data analysis software.

The binding affinity of H2L5 hIgG4PE for human ICOS is 1.34 nM and cynomolgus ICOS is 0.95 nM (see Table 9). These values are comparable and show, as expected, that a change to the Fc region of the molecule has not affected the binding to the ICOS antigen. Table 9 shows Ka/Kd/KD for humanized 422 (H2L5) IgG4PE to human and cynomolgus ICOS.

TABLE 9

| Binding to human ICOS | | | | |
|---|---|---|---|---|
| Sample | Target | Ka (1/Ms) | Kd (1/s) | KD (M) |
| 422 H2L5 IgG4PE | Human ICOS-Fc | 2.97E+05 | 3.96E-04 | 1.34E-09 |
| 422 H2L5 IgG4PE | Cyno ICOS-Fc | 3.91E+05 | 3.71E-04 | 9.49E-10 |

Discussion

As shown in Example 1 murine clone 422-2 was identified as the lead anti-human ICOS murine antibody. Humanization of this antibody produced 36 heavy and light chain variants which were screened for binding to human and cynomolgus ICOS whilst also ensuring that they did not bind to human CD28 or CTLA-4. The H2L5 variant was identified as the having high affinity for human and cynomolgus ICOS (1.34 and 0.95 nM respectively) whilst containing the minimum number of back mutations.

Changing the isotype from IgG1 to IgG4PE does not affect the binding of the antibody to ICOS.

Example 7: Binding of H2L5 hI2G4PE to Human Activated T Cells

Methods
Experimental Preparation(s)
CD3 Negative Isolation:
CD3+ T Cells were Negatively Isolated by Stemcell Rosette Sep Human T Cell Enrichment Kit
Rosette Sep Human T Cell Enrichment:

100 mL fresh, whole blood was collected with syringes coated in liquid sodium heparin (Sagent 10 IU/mL final concentration). The blood from each collection tube was combined into a flask where 50 μL of Rosette Sep Human T Cell Enrichment cocktail was added per ml of blood. (5 mL/100 mL Donor Blood). The whole blood/Rosette Sep antibody cocktail was incubated for 20 minutes at room temperature (RT). The Blood/Rosette Sep antibody cocktail was then diluted 1:1 with 1× phosphate buffered saline (PBS)+2% FBS (fetal bovine serum). FBS for a final volume of 200 mL. Next, 25 mL of diluted blood/antibody cocktail was then layered over 15 mL of Ficoll gradient in Sepmate tubes (8 tubes in total for each Donor). Loaded Sepmate tubes were then centrifuged at 1200×g for 20 minutes RT with the brakes on. The top layer of plasma down to the peripheral blood mononuclear cells (PBMC) interface was taken off with a pipette and discarded. The remaining plasma and buffy coat interface were decanted from Sepmate tubes into 50 mL conical centrifuge tubes (4 tubes total). The tubes were topped off to 50 mL with PBS+2% FBS. The cells were centrifuged at 400×g for 10 minutes at RT. Supernatants were discarded. The pellets from each donor were then combined into a single 50 mL conical tube, re-suspending the pellets in a total volume of 50 mL PBS+2% FBS. Cells were centrifuged at 400×g for 5 minutes at RT. Supernatants were discarded and the cell pellets were re-suspended in 2 mLs of RPMI Complete Media (RPMI 1640+10% FCS+1 mM sodium pyruvate+2 mM L-glutamine+penicillin 100 U/mL+streptomycin 100 μg/mL). Recovered CD3 Cells were counted on the ViCell instrument and further diluted to 1.2×10$^6$ cells/mL. 1×10$^6$ recovered cells were stained for CD3 PE-Cy7 to confirm the quality of the T cell isolation. CD3+ T cells were negatively isolated by Invitrogen Untouched T cell Isolation Kit PBMC Isolation:

Briefly, 100 mL fresh, whole blood was collected from each donor with syringes coated in liquid sodium heparin (Sagent 10 IU/mL final concentration). Blood was diluted (1:1) to final volume of 200 mL with PBS with 2% FBS. Twenty five (25) mL of diluted blood was layered over 15 mL of Ficoll gradient in Sepmate tubes (8 tubes in total for each donor). Loaded Sepmate tubes were then centrifuged at 1200×g for 20 minutes at RT with the brakes on. The top layer of plasma down to the PBMC interface was taken off with a pipette and discarded. The remaining plasma and buffy coat interface were decanted from Sepmate tubes into 50 mL conical centrifuge tubes (4 tubes total). The tubes were topped off to 50 mL with PBS+2% FBS. The cells were centrifuged at 400×g for 10 minutes at RT. Supernatants were discarded. The pellets from each donor were then combined into a single 50 ml conical tube and re-suspended in a total volume of 50 mL PBS+2% FBS. Cells were centrifuged at 400×g for 5 minutes at RT. Supernatants were discarded, and the cell pellets were re-suspended in an arbitrary volume of Isolation Buffer (dependent upon the size of the cell pellet) provided in the Invitrogen Untouched T cell kit. Isolated PBMC's were then counted on the ViCell instrument and brought to a final concentration of 1×10$^8$ cells/mL in Isolation Buffer.

Invitrogen Dynabead Untouched Human T Cell Isolation:

2×10$^8$ isolated PBMCs (2 mLs), 400 μl of FBS and then 400 μl of Antibody Mix from the Invitrogen Untouched T cell kit were added to each 15 mL tube and incubated for 20 minutes at 4° C. Cells were washed with 10 mLs of Isolation Buffer and centrifuged at 350×g for 8 minutes at 4° C. Supernatants were discarded, and the pellets were re-suspended in 2 mLs of Isolation Buffer. Next, 2 mLs of pre-washed Depletion Dynabeads were added to each tube. Cells were incubated with the beads for 15 minutes at room temperature with gentle tilting and rotation. Following the bead incubation, 10 mLs of Isolation Buffer was added and the cell/bead suspensions were pipeted up and down 10 times. The tubes were placed into a magnet for 2 minutes at room temperature. Without disturbing the magnetized beads, the supernatants containing the untouched T Cells were collected. The beads were washed 1 time with 10 mLs of Isolation Buffer and placed into the magnet again for 2 minutes at room temperature, and the bead-cleared buffer collected. The collected cells were centrifuged at 400×g for 5 minutes at RT. Supernatants were discarded, and the cell pellets were re-suspended in an arbitrary volume of RPMI Complete Media dependent upon cell pellet size (2 to 35 mLs). Recovered CD3+ cells were then counted on the ViCell and brought to a concentration of $1.2\times10^6$ cells/mL in RPMI Complete Media.

CD3 Confirmation Staining:

$1\times10^6$ recovered cells were stained with 5 µl anti-CD3 PE-Cy7 or 5 µl IgG1 Pe-Cy7 Isotype for 40 minutes at 4° C. in the dark. Cells were then washed twice in ice-cold PBS with 0.1% Tween20, centrifuging at 400×g for 5 minutes at 4° C. Stained cells were re-suspended in 1% formaldehyde and incubated at 4° C. for 20 minutes in the dark. Cells were then washed twice in ice-cold PBS with 0.1% Tween20, centrifuging at 400×g for 5 minutes at 4° C., and re-suspended in 275 µl of PBS with 0.1% Tween20. Fixed cells were stored at 4° C. in the dark until Flow Cytometry was performed to confirm the quality of the T cell isolation.

Activation of Isolated Human T Cells:

T75 flasks were coated with 4 mL of 1 µg/ml CD3/CD28 in PBS for 2 hours at 37° C. Flasks were washed twice with 12 mL of PBS. $30\times10^6$ cells in 25 mLs of RPMI Complete Media were added per T75 flask. Cells were incubated for 48 hours at 37° C., 5% $CO_2$ to allow activation to occur.

Binding of Anti-ICOS (H2L5 hIgG4PE):

Binding of H2L5 hIgG4PE was assessed in both naive and activated CD3+ T cells. An 8-point titration from 0.00128 to 100 µg/mL H2L5 hIgG4PE with 5 fold dilutions was employed.

Either naive and/or activated CD3+ T cells were re-suspended in PBS with 0.1% BSA (FACS Buffer) containing Human FcR Blocking Solution at $2\times10^6$ cells/mL (5µl FcR Blocking Solution+950 µl FACS Buffer per 1 mL). At a concentration of $2\times10^5$ cells/well, 100 µl cells were placed into 2 mL 96 well Assay Blocks and incubated at room temperature for 15 minutes. During the incubation, a titration of the binding antibodies, anti-ICOS (H2L5 hIgG4PE) or IgG4 Isotype Control antibody was prepared as a 2× concentration. Following the incubation of FcR block, 100 µl per well of the 2× concentrated binding antibodies were added to the 100 µl of Fc blocked T cells per well to achieve a final 1× concentration of anti ICOS (H2L5 hIgG4PE) or IgG4 Isotype Control antibody from 0.00128 to 100 µg/mL final concentration Cells were incubated with antibodies for 20 minutes at room temperature. Following the binding incubation, cells were washed twice in 1 mL of FACS buffer, centrifuging at 400×g for 5 minutes at room temperature.

Staining of Naive or Activated T Cells Following Anti-ICOS (H2L5 hIgG4PE) Binding:

Cells were stained for flow cytometry with the following cocktails:

| Staining Cocktail: | | |
| --- | --- | --- |
| Antibody | Vol. per well (µl) | Vol. for 110 (µl) |
| PE Mouse anti-Human CD4 | 5 | 550 |
| APC Mouse anti-Human CD8 | 5 | 550 |
| FITC Goat anti-Human IgG Kappa Light Chain | 10 | 1100 |

| Isotype Cocktail: | | |
| --- | --- | --- |
| Antibody | Vol. per well (µl) | Vol. for 110 (µl) |
| PE Mouse anti-Human CD4 | 5 | 550 |
| APC Mouse anti-Human CD8 | 5 | 550 |
| FITC IgG1, Kappa Isotype Control | 10 | 1100 |

Naive or activated, Fc-blocked T cells were re-suspended in 80 µl of FACS Buffer following the binding incubation with H2L5 hIgG4PE or control antibodies. 20 µl per well of either the Staining or Isotype Cocktail was added per well. Cells were stained for 20 minutes at room temperature in the dark. Following the staining incubation, cells were washed twice in 1 mL of FACS Buffer, centrifuging at 400×g for 5 minutes at room temperature.

Fixation of Stained Cells:

Cells were re-suspended in 500 µl of 1% formaldehyde (10 mLs of 16× concentrated Formaldehyde+150 mLs of 1×PBS) and incubated at room temperature for 20 minutes. Cells were then washed twice with 1 mL FACS buffer, centrifuging at 400×g for 5 minutes at room temperature. Pellets were then re-suspended in 265 µl of FACS Buffer and transferred to a 96 well round bottom plate. Cells were stored at 4° C. in the dark until analysis by flow cytometry.

Flow Cytometry:

Flow cytometry was performed on either the FACS Fortessa X20 or the FACS Canto II using FACSDiva software (Version 8.0). Compensation was performed at the time of acquisition using single stained eBioscience Ultracomp beads and the compensation software in FACSDiva.

Data Analysis

Data acquisition and compensation were performed on BD FACS instruments, LSR Fortessa X-20 or FACS Canto II using BD Diva (ver. 8.0) software. Data analysis employed Flow Jo software (ver.10.0.8r1). Results are reported as both MFI (Median Fluorescence Intensity) and Percent of cells positive for human IgG kappa light chain FITC staining out of the total live cells or appropriate parent population. EC50s were determined using Graphpad Prism 5 software (ver. 5.04) with non-linear regression of transformed data (X=(log(X)) using a variable slope with 4 parameters (log(Agonist) vs. response—Variable slope).

Results

Isolation of T cells from fresh, whole human blood, using either Rosette Sep CD3 Enrichment kit or Dynabead Untouched T cell isolation kits was confirmed by staining with anti-CD3 PeCy7. Donors ranged between 68% and 97% positive for CD3 cells. Anti-CD3/anti-CD28 activated CD4+ and CD8+ cell populations generated H2L5 hIgG4PE-concentration-dependent curves when assessed for anti-human IgG1 Kappa light chain FITC staining. H2L5 hIgG4PE binding curves are presented as both percent anti-human IgG1 Kappa light chain FITC positive and FITC median fluorescence intensity (MFI). T cells incubated with the IgG4 Isotype Control antibody did not produce concentration dependent curves when assessed for anti-human IgG1 Kappa light chain FITC staining. Naive CD4+ or CD8+ cells did not produce full curves; however, there were concentration-dependent increases observed from 0.1 µg/mL to 100 µg/mL.

The median (range) EC50 values were 1.04 µg/mL (0.628-1.31 µg/mL) for CD4+ FITC MFI and 0.652 µg/mL (0.27-0.74 µg/mL) for CD8+FITC MFI, respectively. The median (range) EC50 values were 0.834 µg/mL (0.45-0.965 µg/mL) for CD4+ Percent IgG Kappa Light Chain FITC Positive and 0.583 µg/mL (0.371-1.23 µg/mL) for CD8+ Percent IgG Kappa Light Chain FITC. (Table 10)

TABLE 10

Summary of 422 H2L5 hIgG4PE binding EC50 values to activated human T cells

| Donor # | Activated CD4 T cells | | Activated CD8 T cells | |
|---|---|---|---|---|
| | MFI | Percent Positive | MFI | Percent Positive |
| 1124F36 | 0.628 | 0.45 | 0.564 | 0.619 |
| 1149M52 | 1.31 | 0.882 | 0.74 | 0.547 |
| 1173F42 | 0.636 | 0.612 | 0.27 | 0.371 |
| 1123F59 | 1.04 | 0.853 | Not Performed | Not Performed |
| 1141F45 | 1.27 | 0.965 | Not Performed | Not Performed |
| 2100M39 | No Curve Fit | 0.814 | No Curve Fit | 1.23 |
| 191F39 | No Curve Fit | No Curve Fit | No Curve Fit | No Curve Fit |
| 1155F49 | No Curve Fit | No Curve Fit | Not Performed | Not Performed |
| 1156F64 | No Curve Fit | No Curve Fit | Not Performed | Not Performed |
| Median | 1.04 | 0.834 | 0.652 | 0.583 |
| Mean | 0.977 | 0.763 | 0.525 | 0.692 |
| Std. Dev. | 0.331 | 0.193 | 0.237 | 0.374 |

Discussion

This study demonstrated that H2L5 hIgG4PE (anti-ICOS agonist antibody) bound to ICOS receptor on activated T cells from healthy human donors. H2L5 hIgG4PE binding to the cell surface of T cells was detected using an antibody against human IgG kappa light chain labelled with FITC.

The successful isolation of CD3+ T cells was confirmed through flow cytometry with anti-CD3 Pe-Cy7 staining. Nine of ten donors resulted in greater than 89% CD3+ T cells after isolation. However, Donor#2100M39 was only 68.6% CD3+ following isolation. The cause of this decreased purity in Donor#2100M39's T cell isolation is unknown. EC50 values generated from gated CD4+ and CD8+ populations from Donor#2100M39 do not appear to be aberrant and were included in the summarized median values.

Binding EC50s were determined for H2L5 hIgG4PE in negatively isolated human T cells. Binding curves were generated when the isolated T cells were activated by 48 hours exposure to 1 µg/mL plate bound CD3/CD28 antibodies. Both percent IgG kappa light chain FITC positive cells and FITC MFI data from CD4+ and CD8+ activated T cells were considered in the statistical analyses. The median CD4+EC50 values were similar when calculated as percent FITC positive cells or FITC MFI, 1.04 and 0.834 µg/mL, respectively. The median CD8+EC50 values were also similar when calculated as percent FITC positive cells or FITC MFI, 0.652 and 0.583 µg/mL, respectively.

T cells incubated with the IgG4 PE isotype control did not result in concentration-dependent increases in anti-human IgG kappa light chain FITC binding regardless of the analysis method employed, MFI or Percent Positive Cells.

Full curves could not be obtained from naive or unactivated, negatively isolated T cells in the 0.00128 to 100 µg/mL H2L5 hIgG4PE range tested. However, a concentration-dependent increase in binding was observed in donors from 0.1 to 100 µg/mL H2L5 hIgG4PE. EC50s could not be calculated as the curves from naive T cells were incomplete. The inability of H2L5 hIgG4PE to bind at low concentrations to naive or unactivated cells was expected since ICOS is only weakly expressed on resting Th17, T follicular helper (TFH) and regulatory T (Treg) cells. TCR engagement and activation are required to induce ICOS expression. Thus, there was likely very little ICOS receptor expressed on naive or unactivated cells, and consequently minimal binding of H2L5 hIgG4PE.

Example 8: TK/PD Results from Cyno Dose-Range Finding (DRF) Study

To access the in vivo characteristics of H2L5 hIgG4PE in a target-relevant species a dose-range finding study was performed in cynomolgus monkeys. The study tested 3 dose levels (0.3, 3 and 30 mg/kg) in addition to a vehicle control cohort. It was a repeat dose with the second dose administered 14 days after the first. One male and one female were tested per cohort. H2L5 hIgG4PE exhibited a dose-dependent increase in $C_{max}$ (µg/mL) and AUC (µg.h/mL) across the 3 different doses which were tested. At all three dose levels, antibody was detected in the plasma for two weeks following the first dose (FIG. 12A). Anti-H2L5 hIgG4PE antibodies were detected in 3 of the monkeys following a single dose, both of the 0.3 mg/kg dosed animals as well as the female dosed at 3 mg/kg. Anti-H2L5 hIgG4PE antibodies correlated with decreased plasma concentrations following administration of the second dose in these animals (FIG. 12B). Forty-eight hours after the second dose all animals were sacrificed to collect tissue for analysis of pharmacodynamic activity and histopathology analysis.

H2L5 hIgG4PE receptor occupancy (RO) was measured in CD4+ T cells from the spleens and axillary lymph nodes of all animals on study. A dose-dependent increase in H2L5 hIgG4PE binding was observed across the dose levels tested in both tissues (FIG. 13).

Receptor occupancy was also measured on CD4+ T cells from the peripheral blood of monkeys on study. Blood was drawn at 5 time points (Day 1 (pre-dose), day 3, day 8, day 15 (pre-second dose) and day 17). Two different measures were used in this assay to determine RO. The first was a "free-receptor" assay format in that, binding of the anti-ICOS mAb used for flow cytometry detection was determined in the presence or absence H2L5 hIgG4PE which was shown to compete for ICOS binding. Therefore, the absence of anti-ICOS signal by FACS was a surrogate for H2L5 hIgG54PE occupied receptor and conversely, anti-ICOS positivity indicated "free receptor" which was unbound with H2L5 hIgG4PE. FIG. 14-A shows that ICOS free receptor decreased in a dose-dependent, and time dependent manner. Two monkeys (250 and 300) demonstrated "free receptor" signals which could not be explained, and may be due to the production of anti-H2L5 hIgG4PE antibodies in these monkeys. In addition, RO was also measured in peripheral blood CD4+ cells by the same assay used in spleen and lymph nodes described above. As would be expected the 0 mg/kg dose showed no RO by this read out (FIG. 14-B). Interestingly, some monkeys at the 3.0 and 30 mg/kg dose levels showed a time dependent increase in H2L5 hIgG4PE bound CD4+ cell numbers across the treatment time-course. In particular, animal 350 exhibited a (>5-fold) increase in drug-bound circulating CD4+ cells between days 3 and 17 (FIG. 14-B). It is possible that this increase in CD4+ICOS+ cell number could be due to H2L5 hIgG4PE-induced proliferation of this population.

Example 9: H2L5 hI2G4PE Induces Intracellular Signalling Changes in Response to Binding Experimental Preparation(s)
Cell Lines Ba/F3-ICOS cells were obtained from INSERM (Paris, France). Cells were cultured in the appropriate culture medium supplemented with 10% fetal bovine serum (FBS) (Sigma-Aldrich, St. Louis, Mo.), 10 ng/mL recombinant murine IL-3 (R&D Systems, Minneapolis, Minn.), and 1 mg/mL Geneticin (ThermoFisher, Waltham, Mass.) at 37° C. in humidified incubators under 5% $CO_2$.

Experimental Protocol(s)
Intracellular Signalling Antibody Array

Protein lysates were assayed with the PathScan Intracellular Signaling Array Kit (Cell Signaling Technologies) according to the manufacturer's instructions. Briefly, lysates from Ba/F3-ICOS cells treated with IgG4-PE (20 µg/mL) or H2L5 hIgG4PE (0.2, 2, or 20 µg/mL) for 1, 6, 24, and 48 hours were diluted to 1 µg/pt in Array Diluent Buffer and incubated overnight onto the antibody arrays at 4° C. Images of the arrays were captured using the Odyssey imaging software (LI-COR Biosciences, Lincoln, Nebr.).

Phospho-AKT Enzyme-Linked Immunosorbent Assay (ELISA)

Phosphorylation of AKT was measured using the Meso Scale Discovery (MSD) Phospho(Ser473)/Total Akt Whole Cell Lysate Kit and Phospho-Akt (Thr308) Whole Cell Lysate Kit according to the manufacturer's instructions. Cells were seeded at a cell density of $0.25 \times 10^6$ cells/well into 96-well U-bottom plates (BD Falcon) in the appropriate culture media (100 µL/well). Cells were treated for 1, 2, 4, 6, 24, or 48 hours with either the control antibody (IgG4 PE), anti-ICOS IgG1 Fc disabled antibody, or H2L5 hIgG4PE at 7 different concentrations using a 3-fold dilution scheme (dose range: 20.0-0.03 µg/mL) in duplicate wells. For one experiment using the Phospho-AKT (Thr308) Whole Cell Lysate Kit, cells were treated with one concentration of all three antibodies (10 µg/mL) in triplicate wells. The bottom row of each 96-well plate contained a no cells control (two blank duplicate wells) and cells that were left untreated with any antibody. Following treatment, cells were lysed with 30 µL of ice cold lysis buffer containing protease and phosphatase inhibitors, incubated on ice for 30 minutes, and then 25 µL of lysate was transferred to the ELISA plate to incubate overnight at 4° C.

Data Analysis
Densitometry Analysis of Intracellular Signalling Antibody Array

Densitometry analysis was performed to calculate the integrated intensity levels of the spots across the antibody array. The intensities for each spot were normalized to the average of the positive controls on the array (formula=sample well/average of positive controls) and graphed using GraphPad Prism 6.0 (La Jolla, Calif.).

Analysis of MSD ELISA Data

The percent phosphoprotein was calculated for each well using the following calculation: % Phosphoprotein=((2× Phospho-signal)/(Phospho-signal+Total protein signal))×100. This value was then normalized to the untreated cells value at each time point and graphed as "% control" in Microsoft Excel 2007.

Results

Prior studies demonstrated that H2L5 hIgG4PE treatment increased phospho-AKT (S473) levels in Ba/F3-ICOS cells with the maximum response observed between 30-40 minutes after antibody exposure. Here, phospho-AKT levels were measured at later time points to see if increased phosphorylation levels persisted after several days. Additionally, the regulation of other intracellular signalling events by ICOS activation was assessed. In Ba/F3-ICOS cells, phospho-AKT (S473) levels were increased with H2L5 HIGG4PE treatment compared to IgG4-PE isotype control antibody-treated cells after one and six hours of treatment, but this effect was lost after 24 hours (FIG. 15). Interestingly, a similar effect was observed when cells were treated with an anti-ICOS antibody where the Fc region of the antibody is disabled. Increased levels of phospho-AKT (T308) were also observed in H2L5 hIgG4PE and anti-ICOS IgG1 Fc disabled antibody-treated cells compared to IgG4-PE (FIG. 15) isotype control antibody-treated cells after one hour of treatment and persisted up to 48 hours which was the last time point measured. Two other phospho-proteins downstream of AKT, Glycogen Synthase Kinase 3 Alpha (GSK3α) and ribosomal protein S6, were also modestly increased upon ICOS activation, but the effects were not as robust at those seen with phospho-AKT. Protein lysates were also analyzed using an antibody array that measures the phosphorylation or cleavage of 18 proteins involved in intracellular signalling. Using this approach, only three proteins showed slight increases in phosphorylation upon ICOS activation: phospho-AKT (S473), phospho S6 (S235/236), and phospho-SAPK/JNK (T183/Y185).

To measure changes to AKT phosphorylation using an assay format that would allow for direct quantitation, Ba/F3-ICOS cells were treated with a dose range of control antibody (IgG4 PE), anti-ICOS IgG1 Fc disabled antibody, or H2L5 hIgG4PE over time and monitored by ELISA. Increased phospho-AKT (S473) levels were both dose-dependent and time-dependent in anti-ICOS IgG1 Fc disabled antibody-treated or H2L5 hIgG4PE-treated cells. As previously observed, maximal phospho-AKT (S473) activation occurred after 1 hour of treatment. The phospho signal slightly decreased after 2 hours and persisted up to 6 hours but was eventually lost after 24 hours. An ELISA that measures phospho-AKT (T308) levels was also tested here but no reproducible activation could be observed with this ELISA kit.

Discussion

The AKT signalling cascade can be activated by receptor tyrosine kinases, integrins, B and T cell receptors, cytokine receptors, G-protein-coupled receptors and other stimuli that induce production of phosphatidylinositol (3,4,5) trisphosphates (PIP3) by PI3K [Carnero, 2008]. These lipids serve as plasma membrane docking sites for Akt and its upstream activator PDK1. At the membrane, PDK1 phosphorylates AKT at Thr308 leading to partial activation of Akt [Alessi, 1996]. Phosphorylation of Akt at Ser473 by mTORC2 stimulates full enzymatic activity [Sarbassov, 2005].

ICOS plays a key role in the function of activated effector and regulatory CD4+ T cells by promoting T cell survival, proliferation and memory. Due to its role in sustaining T-cell activation and effector functions, targeting ICOS with an agonist antibody could be a plausible approach to enhance antitumor immunity. In this study, we observed that activation of ICOS by H2L5 hIgG4PE caused changes to AKT phosphorylation in Ba/F3-ICOS cells. Subsequently, proteins downstream of AKT, such as GSK3α (a direct substrate of AKT) and ribosomal protein S6 were also phosphorylated. This data is consistent with work performed recently with this model system, and is in-line with data published externally [Fos, 2008].

Example 10: Functional Effects of Soluble H2L5 hIgG4PE Alone and in Combination with Anti-PD1 and Anti-CTLA-4 Antibody in Human PBMC Assay Experimental Preparation(s)
Isolation of Primary Human PBMC Fresh blood was obtained from GSK Health Center blood donors and was diluted 1:1 with phenol red free-10% RPMI1640 media. Diluted blood was layered on top of the density medium in a Uni-Sep Max 50 ml conical tube and centrifuge at 400×g for 20 minutes at room temperature with BREAK OFF. The resulted white mononuclear layer (buffy coat) was carefully extracted into a new 50 mL conical tube through a 100 µM cell strainer. An equal volume of Phenol red free-10% RPMI1640 media was added to the buffy coat and centrifuged at 300×g for 10 minutes at room temperature. The cell pellet was resuspended in 10 ml of red blood cell lysis solution (Sigma Aldrich) and incubated for 5 minutes at room temperature. Cells were washed once with media and centrifuged as previously described. Volume was brought to 40 ml with Phenol red free-10% RPMI1640 media and cells were counted using Vicell cell counter and viability analyzer (Beckman Coulter).

Induction of Monocyte-Derived Immature Dendritic Cells (iDC)

Human monocytes were isolated using the plastic adherence method. Briefly, 20 million freshly isolated PBMC were cultured in a T-75 tissue culture flask in AIM-V media (Thermo Fisher) for 3 hours. Cells that do not bind to plastic were washed off. The adherent monocytes were cultured in a 37° C. 5% $CO_2$ incubator in AIM-V media supplemented with 1000 U/ml of human GM-CSF (Calt#300-03, PeproTech) and 500 U/ml of human IL-4 (cat#200-04). After 7-10 days, the iDC cells were collected for co-culturing with T cells from a different donor in the allogeneic Mixed Lymphocyte Reaction assays.

Isolation of Primary Human T Cells Directly from Blood

Human T cells were isolated directly from fresh human blood using a human T cell enrichment cocktail (Stem Cell Technologies). The RosetteSep Human T Cell Enrichment Cocktail (50 µL/mL) was added to whole blood and mixed well. After 20 minutes of incubation at room temperature, an equal volume of PBS+2% FBS was added with gentle mixing. The diluted sample was layered on top of the density medium and centrifuged for 20 minutes at 1200×g at room temperature with the brake off. The enriched cells from the density medium: plasma interface were carefully poured into a new conical tube. Next, the red blood cells were lysed with Red Blood Cell Lying Buffer (Sigma Aldrich) and the enriched cells were washed with PBS+2% FBS twice. The T cells were then resuspended in 40 ml of PBS+2% FBS and counted with a Vi-Cell cell counter.

Experimental Protocols
Human PBMC Pre-Stimulation Assay

Freshly isolated human PBMCs were pre-stimulated with CD3/CD28 T cell expander DynaBeads at a bead to cell ratio of 1:20 in a T-75 tissue culture flask in AIM-V medium supplemented with 100 ng/ml of MCSF and 100 IU/ml of IL-2 (PeproTech) at 37° C. After 48 hours, the pre-stimulation beads were magnetically removed and cells were washed, counted and re-stimulated with anti-CD3 DynaBeads and therapeutic antibodies in AIM-V medium supplemented with 100 IU/ml of IL-2 (PeproTech) in 96-well non-tissue culture treated round bottom plate. The seeding density was 100 k cells per 100 µl of medium per well. After incubating at 37° C. for 3.5 days, cell culture supernatants were collected for multiplex cytokine measurement by MSD.

Human MLR Activation Assay

Monocyte-derived iDCs from a healthy human volunteer were mixed at a 1:10 ratio (iDC:T) with freshly isolated human T cells from a different donor and pre-incubated at 37° C. in AIM-V media in the presence of 0.02 µg/ml of a CEFT peptide mixture for 24 hours. Different groups of treatment antibodies were added directly to the wells, mixed and further incubated for an additional 4 days. Cell culture supernatants were collected for multiplex cytokine measurement by MSD analysis.

MSD Cytokine Analysis

IFN-γ, IL-10, IL-2 and TNF-α cytokine levels in the tissue culture supernatant were determined using MSD human V-Plex customized kits. Samples were first diluted 1:200 in Diluent 2. Calibrators were also prepared in Diluent 2 following the manufacturer's recommendations. Diluted samples and calibrators were added to black MSD plates which were subsequently sealed with an adhesive plate seal and incubated at room temperature with shaking for 2 hours. After adding 25 µL of the detection antibody solution, which was freshly prepared in Diluent 2 to each well, the plate was re-sealed and incubated at room temperature with shaking for another 2 hours. The plates were washed 3 times with 150 µL/well of PBS plus 0.05% Tween-20 before adding 150 µl/well of freshly diluted 2× read buffer and immediately read on a MESO QuickPlex reader. Data were analyzed using MSD Workbench software.

Data Analysis
MSD Data Analysis

MSD data was analyzed with Discovery Workbench software (MSD, version 4.0.9). Calibrators in the manufacturer's kit were included on each MSD plate to generate plate specific standard curves with $R^2$ value over 0.99 in all cases. The amounts of cytokine detected were back calculated based on the standard curve and the mean and standard deviation from three biological replicates were used to generate the graphs.

Statistical Analysis

One-way ANOVA was performed on log-transformed, fold-change data over each treatment antibody's own isotype control. Dunnett's Multiple Comparison Test was performed to compare both mono-therapies vs. combination across different donors. $P<0.05$ was considered as statistical significant.

Results

PBMC pre-stimulation assay development and test for combinatorial activity of H2L5 hIgG4PE with ipilimumab and pembrolizumab.

In order to determine the optimal conditions for pre-stimulation, human anti-CD3 Dynabeads and anti-CD3/CD28 Dynabeads (Thermo Fisher) were tested at different bead to cell ratios. After 48 hour pre-stimulation, cells were harvested and beads were magnetically removed prior to stimulation with anti-CD3 Dynabeads (bead to cell ratio=1:1) together with anti-ICOS antibody alone or in combination with anti-CTLA-4 or anti-PD1. H2L5 hIgG4PE single agent treatment resulted in induction of IFN-γ as compared to isotype control in all pre-stimulation conditions tested. The magnitude of IFN-γ induced by H2L5 hIgG4PE was inversely correlated with the strength of the pre-stimulation. The combination of H2L5 hIgG4PE together with ipilimumab demonstrated enhanced cytokine production as compared to either H2L5 HIGG4PE or ipilimumab alone in PBMCs that were weakly pre-stimulated. The combination effect was lost under plate-bound anti-CD3/anti-CD28 pre-stimulation conditions, which is considered a stronger pre-stimulation condition. Based upon these results, the pre-stimulation condition using anti-CD3/anti-CD28 beads at a bead to cell ratio of 1:20 was chosen for all future PBMC assays. Results from four individual donors are summarized for anti-CTLA-4 combination in FIG. 16 and combination with anti-PD-1 in FIG. 17.

H2L5 hIgG4PE Results in Dose-Dependent Cytokine Induction in a PBMC Pre-Stimulation Assay The dose-dependent activity of H2L5 hIgG4PE was evaluated in human PBMCs pre-stimulated with anti-CD3/anti-CD28 beads at a pre-determined bead to cell ratio of 1:20. The anti-RSV IgG4PE and anti-ICOS 422.2 IgG1 Fc Disabled were included as controls. Eight concentrations of H2L5 HIGG4PE were tested (100, 30, 10, 3, 1, 0.3, 0.1, and 0.03 µg/ml). IFN-γ, IL-10 and TNF-α were evaluated by MSD in the tissue culture supernatants of PBMC samples. H2L5 hIgG4PE, but not isotype control IgG4 or Fc-Disabled 422.2, induced IFN-γ, IL-10 and TNF-α production in a dose-dependent manner. These results were used to determine the concentration of H2L5 hIgG4PE to be used in combination studies.

Human MLR Assay Development

In an effort to optimize a human MLR assay, in addition to co-culture of human T cells and monocyte-derived immature DCs from a different donor, anti-CD3 beads were also added into the wells to provide a basal TCR stimuli to help prime the cells. Results demonstrated that anti-CD3 beads greatly increased the range of IFN-γ induction. Although ipilimumab alone can induce IFN-γ production in the absence of anti-CD3 beads, H2L5 hIgG4PE alone or the H2L5 HIGG4PE/ipilimumab combination only showed enhanced IFN-γ production over corresponding controls in the presence of anti-CD3 beads.

Combinatorial Activity of H2L5 HIGG4PE and Ipilimumab in a Human MLR Assay

The immunostimulatory activity of H2L5 hIgG4PE alone or in combination with ipilimumab was tested in an allogeneic human MLR assay in which T cells that were pre-incubated with monocyte-derived immature DCs from an unmatched donor in the presence of 0.02 µg/ml CEFT peptides for 1 day. The H2L5 hIgG4PE/ipilimumab combination resulted in a significant enhancement in IFN-γ production as compared to either agent alone. Results were consistent across three donor pairs tested; however, modest variability was observed between donors (FIG. 18).

Combinatorial Activity of H2L5 hIgG4PE and Pembrolizumab in a Human MLR Assay

The combination of H2L5 hIgG4PE and pembrolizumab was also tested in the human allogeneic MLR assay described above. H2L5 hIg G4PE was tested alone and in combination with pembrolizumab at 10 µg/ml. The combination of H2L5 hIg G4PE and pembrolizumab resulted in increased IFN-γ as compared to either agent alone. However, statistical significance was not reached due to high donor variability and significant activity of single agent anti-PD-1 treatment in some donors (FIG. 19).

Discussion

ICOS is a costimulatory receptor that is weakly expressed on naïve T cells and quickly upregulated in activated CD4+ and CD8+ T cells. The ligand for ICOS is ICOS-L (B7h, B7RP-1, CD275), which is expressed by professional APCs and by peripheral epithelial and endothelial cells following TNF-α stimulation. The ICOS:ICOS-L pathway provides a key costimulatory signal for T-cell proliferation and function. Due to its role in sustaining T-cell activation and effector functions, targeting ICOS by agonist antibodies could be a plausible approach to enhance anti-tumor immunity.

Studies have shown an increase the frequency of ICOS' CD4+ effector T cells after CTLA-4 blockade by ipilimumab in several cancer models. In addition, upon CTLA-4 blockade, this cell population produced greater levels of INF-γ than ICOS$^{lo}$ CD4+ T cells. In fact, the increase in the frequency of ICOS+CD4 T cells has been identified as a pharmacodynamic biomarker of ipilimumab treatment in cancer patients. Studies, in wild-type C57BL/6 mice, demonstrated 80 to 90% tumor rejection follow CTLA-4 blockade therapy; however, in ICOS or ICOSL knockout mice the efficacy was decreased to less than 50%. The important role played by ICOS in the effectiveness of CLTA-4 blockade suggests that stimulating the ICOS pathway during anti-CTLA-4 therapy might increase therapeutic efficacy. Therefore, we set out to evaluate the combination activity of H2L5 hIgG4PE and ipilimumab.

Programmed cell death-1 (PD-1) was reported in 2000 to be another immune checkpoint molecule. The expression of PD-L1 (B7-H1), which is one of the ligands of PD-1, can be found on many cell types including T cells, epithelial cells, endothelial cells, and tumor cells. Antibodies targeting the PD-1/PD-L1 axis have also shown clinical responses in multiple tumor types. The FDA recently approved pembrolizumab and nivolumab as second generation of the immune checkpoint blockers for the treatment of cancer. Merck's pembrolizumab was shown to lead to response rates of ~37 to 38% in patients with advanced melanoma, with a subsequent study reporting an overall response rate of 26% in patients who had progressive disease after prior ipilimumab treatment. Nivolumab, the anti-PD-1 antibody from BMS, also showed clinical benefit in patients with metastatic melanoma with a response rate of 40% and an overall survival rate of 72.9% at 1 year. In addition, nivolumab was also FDA-approved for advanced or metastatic non-small cell lung cancer. As the PD-1 checkpoint blockade antibodies become the dominant cancer immune therapy in the clinic, it will be important to evaluate H2L5 hIgG4PE in combination with an anti-PD-1 antibody for their combined anti-tumor activity.

Previously, a PBMC activation assay was developed and used to evaluate the T cell stimulation activity of a panel of anti-ICOS agonist antibodies. The data generated from those studies supported the candidate selection of clone 422.2 with an IgG4PE isotype as H2L5 hIgG4PE. In the previous assay, PBMC cells were pre-stimulated with plate bound anti-CD3 antibody at 1 µg/ml and anti-CD28 antibody at 3 µg/ml for 48 hours before they were harvested and re-stimulated with anti-CD3 and soluble ICOS antibodies that were being investigated. H2L5 hIgG4PE was shown to induce IFN-γ production in a dose-dependent manner. In order to determine the optimal conditions for pre-stimulation, human anti-CD3 Dynabeads and anti-CD3/CD28 Dynabeads (Thermo Fisher) were tested at different bead to cell ratios. Stimulation by beads is considered to be more physiological and the strength of the stimulation can be controlled more easily by constructing different bead to cell ratios. After 48 hours of pre-stimulation, cells were harvested and beads were magnetically removed prior to stimulation with anti-CD3 Dynabeads (bead to cell ratio=1:1) together with anti-ICOS antibody alone or in combination with anti-CTLA-4. The results showed that H2L5 hIgG4PE single agent treatment resulted in IFN-γ induction relative to isotype control in all pre-stimulation conditions tested. The magnitude of IFN-γ induced by H2L5 hIgG4PE was inversely correlated with the strength of the pre-stimulation. The combination of H2L5 hIgG4PE together with ipilimumab demonstrated enhanced cytokine production as compared to either H2L5 hIgG4PE or ipilimumab alone in PBMCs that were weakly pre-stimulated. The combination effect was lost under plate-bound anti-CD3/anti-CD28 pre-stimulation conditions, which is considered a stronger pre-stimulation condition. Based upon these results, the pre-stimulation condition using anti-CD3/anti-CD28 at a bead to cell ratio of 1:20 was chosen for all the future PBMC assays. H2L5 hIgG4PE and ipilimumab combination demonstrated a statistically significant increase in IFN-γ production as compared to either antibody treatment alone.

In the assay optimization effort, with an anti-CD3/anti-CD28 stimulation bead to cell ratio fixed at 1:20, the anti-CD3 beads used during the re-stimulation step were titrated down from bead to cell ratios of 1:1 to 1:3 and 1:10. The results showed that the lower the re-stimulation strength yielded lower the IFN-γ induction by H2L5 hIgG4PE. The combination effect by H2L5 hIgG4PE and ipilimumab was totally lost under re-stimulation at a bead to cell ratio of 1:3 and 1:10. Therefore, the re-stimulation anti-CD3 bead to cell ratio of 1:1 was kept for all future experiments.

With the pre-stimulation and re-stimulation conditions optimized, this assay was used to evaluate the dose response of H2L5 hIgG4PE. A total of 8 antibody concentrations were tested, which were 100, 30, 10, 3, 1, 0.3, 0.1 and 0.03 µg/ml. The anti-RSV IgG4PE and anti-ICOS 422.2 IgG1 Fc Disabled, the Fc Disabled version of H2L5 hIgG4PE, were used as controls. Results showed that H2L5 hIgG4PE, but not isotype control IgG4 or Fc-Disabled 422.2, induced IFN-γ, IL-10 and TNF-α production in a dose-dependent manner. It is interesting that the Fc Disabled version of H2L5 hIg G4PE exhibited a limited cytokine induction response, indicting the Fc receptor engagement is crucial for the T cell agonizing function of H2L5 hIg G4PE. These results were also used to determine the dose of H2L5 hIg G4PE for combination studies.

A mixed lymphocytes reaction (MLR) assay was also developed to evaluate the combination effect of H2L5 hIg G4PE and checkpoint blocking antibodies. MLR assay is an ex vivo cellular immune assay in which primary monocyte-derived immature dendritic cells (iDCs) were mixed with T cells isolated from a different donor. The mismatch of major histocompatibility complex (MHC) molecules on the surface of iDC cells can initiate T cell stimulation in an allogeneic setting. In the clinic, the MLR assay is well-known for identifying the compatibility of tissue transplants between donors and recipients.

In order to develop the MLR assay, fresh human monocytes were cultured in medium supplemented with human recombinant GM-CSF and IL-4 for a week to induce an immature DC phenotype. Then fresh human T cells from a different donor were isolated and mixed with the iDC cells at a 10:1 ratio (T:iDC). H2L5 hIg G4PE and ipilimumab mono-therapy or combinational treatments were added to the T cell/iDC co-culture in the presence or absence of anti-CD3 beads. The purpose of the anti-CD3 beads was to provide a basal TCR stimulus to help prime the T cells. Results showed anti-CD3 beads greatly increased the range of IFN-γ induction in the assay. Although ipilimumab alone can induce IFN-γ production in the absence of anti-CD3 beads, H2L5 hIgG4PE alone or the H2L5 hIgG4PE/ipilimumab combination showed enhanced IFN-γ production over corresponding controls in the presence of anti-CD3 beads. This result suggests that, in this assay, the TCR stimulus by DC cells alone may not be sufficient to induce ICOS expression on the surface of resting T cells that were freshly isolated from PBMCs. In order to improve the situation, a 24 hour iDC and T cells pre-incubation step was added before the addition of therapeutic antibodies. The CEFT peptide mix was also added into the assay procedure to better prime the T cells and to elicit an antigen-specific response. The CEFT peptide pool consists of 27 peptides selected from defined HLA class I and II-restricted T-cell epitopes from human Cytomegalovirus (HHV-5; CMV), Epstein-Barr virus (HHV-4; EBV), Influenza A and *Clostridium tetani*. Considering the high vaccination frequency against Influenza and *Clostridium tetani* and the high prevalence of CMV and EBV in the general population, recall antigen responses were expected for a majority of the human samples. The results showed that increased IFN-γ production was observed when T cells were pre-incubated with iDC cells for 24 hours, and the IFN-γ production further increased when CEFT peptides were added to the co-culture system. The immunostimulatory activity of H2L5 hIgG4PE alone or in combination with ipilimumab was tested in the allogeneic human MLR assay in which T cells that were pre-incubated with monocyte-derived immature DCs from an unmatched donor in the presence of 0.02 µg/ml CEFT peptides for 1 day. The H2L5 hIgG4PE/ipilimumab combination resulted in a significant enhancement in IFN-γ production as compared to either agent alone. The results were consistent across three donor pairs tested; however, modest variability was observed between donors.

Similarly, the combination of H2L5 hIgG4PE and pembrolizumab was also tested in the human allogeneic MLR assay described above. H2L5 hIgG4PE was tested alone and in combination with pembrolizumab at 10 µg/ml. The combination of H2L5 hIgG4PE and pembrolizumab resulted in increased IFN-γ as compared to either agent alone. However, statistical significance was not reached due to high donor variability and significant activity of single agent anti-PD-1 treatment in some donors.

In summary, these studies demonstrated the superior combination activity of H2L5 hIgG4PE with two FDA-approved check point inhibitors, ipilimumab and pembrolizumab, when compared to mono-therapies in two human immune cell based assays. In the studies reported here, H2L5 hIgG4PE was shown to promote T cell activation and TH1 skewing (e.g. IFN-γ production) that is characteristic of productive anti-tumor immune responses.

Example 11: Functional Activity of H2L5 hIgG4PE Alone and in Combination with Anti-PD1 and Anti-CTLA-4 Antibodies In Vivo Human PBMC Mouse Tumor Model
Methods
Experimental Preparations
All procedures on animals were reviewed and approved by the GSK Institutional Animal Care and Use Committee prior to initiation of the studies protocol.
Preparation of Cell Lines:
A2058 were propagated according to ATCC protocol.
Materials:
    A2058 human melanoma cell line: ATCC, Cat# CRL-11147, 1° 059349362
    DPBS: ATCC, Cat #30-2200, Lot#63357436
    Dulbecco's Modified Eagle's Medium: ATCC, Cat #30-2002, Lot#62596471 Expiration: October-2015
    Fetal Bovine Serum: Sigma-Aldrich, Cat#12176c-1000 ml, lot #13G180R0H1, Expiration: July-2018

0.25% (w/v) Trypsin-0.53 mM EDTA: ATCC, Cat #30-2102, Lot#62420300

Antibiotic-Antimycotic (100×): Life Technologies, Cat#15240-062

T175 cell culture flask: Greiner bio-one, Cat#661175

T75 cell culture flask: Greiner bio-one, Cat#658175

Medium:
  A2058 complete growth medium: Dulbecco's Modified Eagle's Medium+10% FBS. Culture conditions: Atmosphere: Air, 95%; 5% carbon dioxide ($CO_2$); Temperature: 37° C.

Upon receipt of the cells:

Pre-warm complete medium at 37° C.

Thaw the cells quickly in 37° C. water bath. Wipe the tube with 70% ethanol and transfer cells to 15 ml tube filled with prewarmed complete medium.

Centrifuge at 1200 rpm for 5 minutes to collect the cell pellet.

Add the cells back to T75 flask filled with prewarmed complete medium and incubate at 37° C.

Subculture of the Cells:
  Volumes are given for a 75 cm² flask (For T175 cm² flask, adjust the amount of dissociation and culture medium needed proportionally).
  Remove and discard culture medium.
  Briefly rinse the cell layer with DPBS to remove all traces of serum that contains trypsin inhibitor.
  Add 2.0 to 3.0 mL of Trypsin-EDTA solution to flask and observe cells under an inverted microscope until cell layer is dispersed (2-3 minutes).
  Note: To avoid clumping do not agitate the cells by hitting or shaking the flask while waiting for the cells to detach. Cells that are difficult to detach may be placed at 37° C. to facilitate dispersal.
  Add 10 mL of complete growth medium and aspirate cells by gently pipetting.
  Centrifuge at 1200 rpm for 5 minutes to collect the cell pellet, add 10 ml of complete growth medium
  Add appropriate aliquots of the cell suspension to new culture vessels. Incubate cultures at 37° C.
  Medium Renewal: Every 2 to 3 days Preparation of Tumor Cells for Mice Inoculation:
  Wash cells with 1×DPBS, add 3 ml 1× Trypsin for 2-3 minutes.
  Add complete growth media and collect the cell suspension in sterile conical centrifuge tube in the tissue culture hood.
  Centrifuge the cells at 1200 rpm for 5 minutes to obtain cell pellet.
  Wash cells with 1×DPBS solution, Centrifuge at 1200 rpm for 5 minutes to obtain cell pellet. Repeat the washing 2 times.
  Count the cells by hemocytometer for cell number and viability.
  Resuspend the cells in ice-cold PBS at concentrations for In Vivo inoculation (A2058, 2.5e7/ml, 2.5e6/100 μl/mouse).

Tumor Cell Line Inoculation to NSG Mice

Materials:
  Mouse: NOD.Cg-Prkdcscid Il2rgtm1Wjl/SzJ. The Jackson Laboratory Stock: 005557 Female Age: 6 weeks
  1 mL Tuberculin Syringes with Attached Needle 25 G 5/8: Becton Dickinson, Cat#305554
  PDI™ Alcohol Prep Pads: Professional Disposables, Cat# B339
  PDI™ Povidone-iodine Prep Pad: Professional Disposables, Cat# B40600

Preparation of mice
  Mice should be 6 weeks old.
  Allow 3-5 days acclimatization period after mice have arrived.
  Shave the mice on right hind flank Preparation of the Injection
  Clean and sterilize the inoculation area of the mice with iodine followed by ethanol pad
  Use 1-cc syringe and a 25-gauge needle
  Pull out the plunger, mix cells and add 100 μl of cells to the back of syringe, carefully insert the plunger.
  Inject cells subcutaneously (s.c.) into the right hind flank of the mouse.

Tumor Growth Assessment
  To measure a tumor, wet fur with 70% ethanol to make it easier to find tumor margins. Measure tumor size and body weight every 2-3 days.
  Tumor size is measured with a digital caliper, and the volume is determined as follow: Tumor volume (mm3) =(length)×(width)²/2

Human PBMC Intravenous Administration
  Human PBMC administration can start 1 week after when the tumors have reached an average volume of approximately 100 mm3.

Materials:
  Fresh Human PBMC: Allcells, cat#C-PB102-3B2
  1 mL Tuberculin Syringes with Attached Needle 25 G 5/8: Becton Dickinson, Cat#305554
  PDI™ Alcohol Prep Pads: Professional Disposables, Cat# B339
  PDI™ Povidone-Iodine: Prep Pad: Professional Disposables, Cat# B40600
  Gauze sponges: Covidien, cat#441211
  Mouse Tail Illuminator Restrainer: Braintree scientific, cat#MTI STD PBMC preparation
  Fresh human PBMC are purchased from Allcells by overnight shipment.
  Centrifuge the cells at 1400 rpm for 5 minutes to obtain cell pellet.
  Wash cells with 1×DPBS solution, Centrifuge at 1400 rpm for 5 minutes to obtain cell pellet.
  Resuspend the cells in ice-cold PBS at concentrations for In Vivo injection (20e7/ml).
  Use 1-cc syringe and a 25-gauge needle.
  Pull out the plunger, mix cells and add 100 μl of cells to the back of syringe, carefully insert the plunger.
  Keep the cells on ice.

Tail Vein injection
  Warm the mice with an incandescent lamp for 5 minutes
  Restrain the mice with tail illuminator restrainer.
  Rotate the tail slightly to visualize vein.
  Clean and sterilize injection site with iodine followed by ethanol pad
  Insert needle into the vein at a slight angle and inject the cells.
  Remove the needle and apply gentle compression with Gauze sponges until bleeding has stopped.
  Return animals to their cage and observe for 5-10 minutes to make sure that bleeding has not resumed.

Therapeutic Antibody Administration
  1-3 days post human PBMC injection, mice are administrated with antibodies by Intraperitoneal injection.

Materials:
Fully human IgG1 isotype control: Eureka therapeutics, cat#ET-901 (preclinical grade) Lot#15-726 Expiration: February 2017
Ipilimumab (Yervoy): Bristol-Myers Squibb NDC 0003-2327-11, lot#921873 Expiration: April 2015; lot#4H69490, Expiration: May 2016
Fully human IgG4 isotype control: Eureka therapeutics, cat#ET-904 (preclinical grade) Lot#15-726 Expiration: February 2017
Anti human ICOS H2L5 hIgG4PE
Pembrolizumab (Keytruda): Merck, NDC 0006-3026-02, lot# L010592, Expiration: Apr. 26, 2016
Intraperitoneal injection:
Draw up, into the syringe and needle, 100 µl of to be administered.
Line the bevel of the needle with the numbers on the syringe.
Sufficiently restrain the animal with your non-dominant hand.
Entry point for the needle: Draw an imaginary line across the abdomen just above the knees, the needle will be inserted along this line on the animal's right side and close to the midline. As this is a female, you can see that the point of entry is cranial to and slightly medial of the last nipple.
Tilt the mouse with its head slightly toward the ground so that its head is lower than its hind end.
Insert the needle into the abdomen at about a 30-degree angle.
The shaft of the needle should enter to a depth of about half a centimeter.
After injection, withdraw the needle and return the mouse to its cage.
Blood and tumor sampling
Materials:
Microvette CB300 (Serum): Braintree Scientific, Cat# MV-CB300 16440
Microvette CB300 (Hematology/Potassium EDTA): Braintree Scientific, Cat# MV-CB300 16444
Blood:
Mice were tail vein bled once a week.
30 µl of blood was collected in Microvette CB300 (Hematology/Potassium EDTA) for flow cytometry analysis.
Another 30 µl of blood was collected in serum Microvette CB300 and incubated for 2 hours at room temperature to allow clotting, followed by centrifugation at 2000×g in order to collect serum. Serum was stored at −20 until further analysis.
Tumor:
Mice were euthanized when tumor size reached 2000 mm$^3$. Tumors were collected and processed in the following procedure.
Experimental Design
All studies were prepared according to procedures listed above.
H2L5 hI2G4PE Dose Response
This study was designed to determine dose-dependent activity of H2L5 hIgG4PE in human PBMC engrafted NSG mice implanted with A2058 melanoma tumors. Nine groups with 10 mice per group and 1 control group (Tumor only no PBMC) with 7 mice were assigned into each study. A summary of the treatment regimen for dose response using human PBMC from donor #7129 is present in Table 11. H2L5 hIgG4PE was dosed at 0.04, 0.4, 1.2 and 4 mg/kg. Ipilimumab was dosed at 3 mg/kg and an Fc-Disabled variant of the anti-ICOS agonist was tested at 1 mg/kg. Test groups were evaluated relative to the vehicle and matched isotype control groups. Survivability analysis concluded on day 49 at termination of the study.

TABLE 11

Summary of Treatment Regimen for H2L5 hIgG4PE Dose Response in Mice

| Groups | Treatment 1 | Treatment 2 | # mice/ group | Dosing |
|---|---|---|---|---|
| 1 | Tumor + huPBMC (donor #7129) | Vehicle | 10 | Twice weekly for 3 weeks |
| 2 | Tumor + huPBMC (donor #7129) | human IgG1 Isotype (3 mg/kg) | 10 | Twice weekly for 3 weeks |
| 3 | Tumor + huPBMC (donor #7129) | Ipilimumab (3 mg/kg) | 10 | Twice weekly for 3 weeks |
| 4 | Tumor + huPBMC (donor #7129) | human IgG4 (4 mg/kg) | 10 | Twice weekly for 3 weeks |
| 5 | Tumor + huPBMC (donor #7129) | H2L5 hIgG4PE (0.04 mg/kg) | 10 | Twice weekly for 3 weeks |
| 6 | Tumor + huPBMC (donor #7129) | H2L5 hIgG4PE (0.4 mg/kg) | 10 | Twice weekly for 3 weeks |
| 7 | Tumor + huPBMC (donor #7129) | H2L5 hIgG4PE (1.2 mg/kg) | 10 | Twice weekly for 3 weeks |
| 8 | Tumor + huPBMC (donor #7129) | H2L5 hIgG4PE (4 mg/kg) | 10 | Twice weekly for 3 weeks |
| 9 | Tumor + huPBMC (donor #7129) | ICOS-Fc-disabled (1 mg/kg) | 10 | Twice weekly for 3 weeks |
| 10 | Tumor (no PBMC) (donor #7129) | Untreated | 7 | Twice weekly for 3 weeks |

Efficacy and Pharmacodynamic (PD) Activity Study with H2L5 hIgG4PE in Combination with Ipilimumab and Pembrolizumab
Study Objectives:
To evaluate the anti-tumor activity of H2L5 hIgG4PE monotherapy dosed at 0.04 mg/kg and 0.4 mg/kg.
To evaluate the anti-tumor activity of H2L5 hIgG4PE dosed in combination with ipilimumab or pembrolizumab with matched isotype controls.
Collection of tissue for future pharmacodynamic activity study of H2L5 hIgG4PE. A total of 22 treatment groups with 10 mice per group were assigned to this study. Groups 1-16 were the efficacy cohorts and 17-22 were pharmacodynamic activity cohorts.
For combination treatments, H2L5 hIgG4PE (0.04 or 0.4 mg/kg) and ipilimumab or IgG1 (3 mg/kg) or H2L5 hIgG4PE (0.04 or 0.4 mg/kg) and pembrolizumab or IgG4 (5 mg/kg) were dosed. H2L5 hIgG4PE and ipilimumab as well as the matched isotype controls were dosed twice weekly for 6 doses, pembrolizumab and isotype control were dosed every 5 days until end of the H2L5 hIgG4PE dose. For the pharmacodynamic tissue collection cohorts, H2L5 hIgG4PE was dosed at 0.004, 0.04, 0.4 and 1.2 mg/kg. Treatment groups were evaluated relative to the vehicle and isotype control groups. Treatment groups for vehicle, isotypes and H2L5 hIgG4PE alone and in combination with ipilimumab and pembrolizumab using human PBMC from donor number #6711 are shown in Table 12. Analysis concluded on day 59 at termination of the study.

TABLE 12

Treatment groups of mice in A2058 melanoma tumor model

| Group | Treatment 1 | Treatment 2 | # mice/ group | Dosing |
|---|---|---|---|---|
| 1 | Tumor + huPBMC (donor #6711) | Vehicle | 10 | Twice a week for 6 doses |
| 2 | Tumor + huPBMC (donor #6711) | Isotype control (IgG1 3 mg/kg + IgG4 5 mg/kg) | 10 | IgG1 Twice a week for 6 doses IgG4 every 5 days until the end of ICOS dose |
| 3 | Tumor + huPBMC (donor #6711) | Ipilimumab 3 mg/kg + IgG4 5 mg/kg | 10 | Twice a week for 6 doses IgG4 every 5 days until the end of ICOS dose |
| 4 | Tumor + huPBMC (donor #6711) | Pembrolizumab 5 mg/kg + IgG1 3 mg/kg | 10 | IgG1 Twice a week for 6 doses Pembrolizumab every 5 days until the end of ICOS dose |
| 5 | Tumor + huPBMC (donor #6711) | H2L5 hIgG4PE 0.04 mg/kg + IgG1 3 mg/kg | 10 | IgG1 and ICOS Twice a week for 6 doses |
| 6 | Tumor + huPBMC (donor #6711) | H2L5 hIgG4PE 0.4 mg/kg + IgG1 3 mg/kg | 10 | IgG1 and ICOS Twice a week for 6 doses |
| 7 | Tumor + huPBMC (donor #6711) | Ipilimumab 3 mg/kg + Pembrolizumab 5 mg/kg | 10 | Ipilimumab Twice a week for 6 doses Pembrolizumab every 5 days until the end of ICOS dose |
| 8 | Tumor + huPBMC (donor #6711) | H2L5 hIgG4PE 0.04 mg/kg + Ipilimumab 3 mg/kg | 10 | Ipilimumab and ICOS Twice a week for 6 doses |
| 9 | Tumor + huPBMC (donor #6711) | H2L5 hIgG4PE 0.4 mg/kg + Ipilimumab 3 mg/kg | 10 | Ipilimumab and ICOS Twice a week for 6 doses |
| 10 | Tumor + huPBMC (donor #6711) | H2L5 hIgG4PE 0.04 mg/kg + Pembrolizumab 5 mg/kg | 10 | ICOS Twice a week for 6 doses Pembrolizumab every 5 days until the end of ICOS dose |
| 11 | Tumor + huPBMC (donor #6711) | H2L5 hIgG4PE 0.4 mg/kg + Pembrolizumab 5 mg/kg | 10 | ICOS Twice a week for 6 doses Pembrolizumab every 5 days until the end of ICOS dose |
| 12 | Tumor + huPBMC (donor #6711) | IgG4 5 mg/kg | 10 | Twice a week for 6 doses |
| 13 | Tumor + huPBMC (donor #6711) | Pembrolizumab 2.5 mg/kg | 10 | Pembrolizumab every 5 days until the end of ICOS dose |
| 14 | Tumor + huPBMC (donor #6711) | Pembrolizumab 5 mg/kg | 10 | Pembrolizumab every 5 days until the end of ICOS dose |
| 15 | Tumor + huPBMC (donor #6711) | H2L5 hIgG4PE 0.4 mg/kg | 10 | ICOS Twice a week for 6 doses |
| 16 | Tumor + huPBMC (donor #6711) | H2L5 hIgG4PE 0.4 mg/kg + Pembrolizumab 5 mg/kg + Ipi | 10 | ICOS Twice a week for 6 doses Pembrolizumab every 5 days until the end of ICOS dose |
| 17 | Tumor + huPBMC (donor #6711) | Vehicle | 10 | Twice a week for pharmacodynamic activity, 5 mice harvested 24 hr post 2nd dose and 5 mice harvested 24 hr post 4nd dose |
| 18 | Tumor + huPBMC (donor #6711) | Isotype Control (IgG4) 1.2 mg/kg | 10 | Twice a week for pharmacodynamic activity, 5 mice harvested 24 hr post 2nd dose and 5 mice harvested 24 hr post 4nd dose |

TABLE 12-continued

Treatment groups of mice in A2058 melanoma tumor model

| Group | Treatment 1 | Treatment 2 | # mice/group | Dosing |
|---|---|---|---|---|
| 19 | Tumor + huPBMC (donor #6711) | H2L5 hIgG4PE 0.004 mg/kg | 10 | Twice a week for pharmacodynamic activity, 5 mice harvested 24 hr post 2nd dose and 5 mice harvested 24 hr post 4nd dose |
| 20 | Tumor + huPBMC (donor #6711) | H2L5 hIgG4PE 0.04 mg/kg | 10 | Twice a week for pharmacodynamic activity, 5 mice harvested 24 hr post 2nd dose and 5 mice harvested 24 hr post 4nd dose |
| 21 | Tumor + huPBMC (donor #6711) | H2L5 hIgG4PE 0.4 mg/kg | 10 | Twice a week for pharmacodynamic activity, 5 mice harvested 24 hr post 2nd dose and 5 mice harvested 24 hr post 4nd dose |
| 22 | Tumor + huPBMC (donor #6711) | H2L5 hIgG4PE 1.2 mg/kg | 10 | Twice a week for pharmacodynamic activity, 5 mice harvested 24 hr post 2nd dose and 5 mice harvested 24 hr post 4nd dose |

Efficacy Study Evaluating H2L5 hIgG4PE Dosed in Combination with Ipilimumab or Pembrolizumab This study was designed to evaluate the anti-tumor efficacy of H2L5 hIgG4PE (dosed at 0.01 and 0.04 mg/kg) in combination with ipilimumab or pembrolizumab with matched isotype controls in the human PBMC engrafted NSG mouse using A2058 melanoma tumor model. A total of 13 groups with 10 mice per group were assigned into the study. Group 2 was the combined isotype control of humanized IgG1 and IgG4. H2L5 hIgG4PE was dosed at 0.01 mg/kg (Group12) and 0.04 mg/kg (Group13) as single agent. For combination treatments, H2L5 hIgG4PE (0.01 and 0.04 mg/kg) and ipilimumab or IgG1 (3 mg/kg) or H2L5 hIgG4PE (0.01 and 0.04 mg/kg) and pembrolizumab or IgG4 (5 mg/kg) was dosed. H2L5 hIgG4PE and ipilimumab as well as the matched isotype controls were dosed twice weekly for 6 doses, pembrolizumab and isotype control was dosed every 5 days until end of the H2L5 hIgG4PE dose. A summary of treatment groups, using human PBMC from donor #4568, is presented in Table 13. Treatment groups were evaluated relative to the vehicle and isotype control groups. Survivability analysis was concluded on day 33 at termination of the study.

TABLE 13

Treatment groups of mice in A2058 melanoma tumor model

| Group | Treatment 1 | Treatment 2 | # mice/group | Dosing |
|---|---|---|---|---|
| 1 | Tumor + huPBMC (donor #4568) | Vehicle | 10 | Twice a week for 6 doses |
| 2 | Tumor + huPBMC (donor #4568) | Isotype control (IgG1 3 mg/kg + IgG4 5 mg/kg) | 10 | IgG1 Twice a week for 6 doses IgG4 every 5 days until the end of ICOS dose |
| 3 | Tumor + huPBMC (donor #4568) | Ipilimumab 3 mg/kg + IgG4 5 mg/kg | 10 | Twice a week for 6 doses IgG4 every 5 days until the end of ICOS dose |
| 4 | Tumor + huPBMC (donor #4568) | Pembrolizumab 5 mg/kg + IgG1 3 mg/kg | 10 | IgG1 Twice a week for 6 doses Pembrolizumab every 5 days until the end of ICOS dose |
| 5 | Tumor + huPBMC (donor #4568) | H2L5 hIgG4PE 0.01 mg/kg + IgG1 3 mg/kg | 10 | IgG1 and ICOS Twice a week for 6 doses |
| 6 | Tumor + huPBMC (donor #4568) | H2L5 hIgG4PE 0.04 mg/kg + IgG1 3 mg/kg | 10 | IgG1 and ICOS Twice a week for 6 doses |
| 7 | Tumor + huPBMC (donor #4568) | Ipilimumab 3mg/kg + Pembrolizumab 5 mg/kg | 10 | Ipilimumab Twice a week for 6 doses Pembrolizumab every 5 days until the end of ICOS dose |
| 8 | Tumor + huPBMC (donor #4568) | H2L5 hIgG4PE 0.01 mg/kg + Ipilimumab 3 mg/kg | 10 | Ipilimumab and ICOS Twice a week for 6 doses |
| 9 | Tumor + huPBMC (donor #4568) | H2L5 hIgG4PE 0.04 mg/kg + Ipilimumab 3 mg/kg | 10 | Ipilimumab and ICOS Twice a week for 6 doses |
| 10 | Tumor + huPBMC (donor #4568) | H2L5 hIgG4PE 0.01 mg/kg + Pembrolizumab 5 mg/kg | 10 | ICOS Twice a week for 6 doses Pembrolizumab every 5 day suntil the end of ICOS dose |
| 11 | Tumor + huPBMC (donor #4568) | H2L5 hIgG4PE 0.04 mg/kg + Pembrolizumab 5 mg/kg | 10 | ICOS Twice a week for 6 doses Pembrolizumab every 5 days until the end of ICOS dose |
| 12 | Tumor + huPBMC (donor #4568) | H2L5 hIgG4PE 0.01 mg/kg | 10 | Twice a week for 6 doses |

TABLE 13-continued

Treatment groups of mice in A2058 melanoma tumor model

| Group | Treatment 1 | Treatment 2 | # mice/ group | Dosing |
|---|---|---|---|---|
| 13 | Tumor + huPBMC (donor #4568) | H2L5 hIgG4PE 0.04 mg/kg | 10 | Twice a week for 6 doses |

Statistical Analysis

The event for survival analysis was tumor volume >2000 mm$^3$, tumor ulceration, mouse body weight loss >20%, moribund or found dead, whichever came first. The exact time to cut-off volume was estimated by fitting a linear line between log tumor volume and day of two observations, the first observation that exceed the cut-off volume and the one observation that immediately preceded the cut-off volume. Kaplan-Meier (KM) method was carried out to estimate the survival probability of different treatment groups at a given time. The median time to endpoint and its corresponding 95% confidence interval was reported. Whether or not KM survival curves are statistically different between any two groups was then tested by log-rank test.

Tumor volume data from the last day in which there were 10 animals per group (i.e. before any animals were euthanized) was utilized to make tumor volume comparisons between the different treatment groups. Prior to the analysis, the tumor volume was natural log transformed due to the inequality of variance in the different treatment groups. ANOVA followed by pair-wise comparison were then carried out on the log transformed data. Graphpad Prism software was used to plot the tumor growth and body weight data.

Results

H2L5 hIgG4PE dose response (FIG. 20A)

Tumor Growth Inhibition:

Control group: Human PBMC (donor 7129) showed no effect on A2058 tumor growth in NSG mice. A2058 tumor bearing mice with or without human PBMC, A2058 tumor bearing mice with human PBMC treated with vehicle and isotype control antibodies developed tumors that progressed as expected (Group#1 vs. Group#10, Group#1 vs. Group#2, Group#1 vs. Group#4, p=1).

Ipilimumab treatment at 3 mg/kg (Group #3) demonstrated significant tumor growth inhibition (p<0.03) as compared to vehicle control Group#1, however the statistical significance was lost (p<0.22) when compared to the isotype control Group #2. This indicated the isotype antibody may affect tumor growth.

H2L5 hIgG4PE treatment at 0.4 mg/kg demonstrated a trend of tumor growth inhibition and increased survivability of mice compared to other doses, although the affects were not statistically significant when compared to either vehicle or isotype control.

Clinical Observations:

Loss of body weight in mice was observed during the study which was approximately 20% at the end of study. It has been reported that both GvHD and tumor burden can result in a drop in mice body weight, though in this study the body weight loss seemed to be more related to A2058 tumor since tumor bearing mice without PBMC engraftment (group #10) showed the same trend. Tumor ulceration was observed in multiple tumors during the study, including the isotype control group.

Mouse Fates:

Most mice were removed upon tumors reaching volumes >2000 mm$^3$. Three mice were euthanized due to tumor ulceration, and three mice were euthanized due to body weight loss of >20%. Nine mice were found dead randomly across the groups, including two in the vehicle, and three total in the isotype control groups. These deaths were attributed to the susceptibility of the model for a Graft-versus-Host Disease state, and not treatment related since no pattern was observed with treatment groups compared to vehicle or isotype control groups.

Efficacy study with H2L5 hIgG4PE in combination with ipilimumab and Pembrolizumab (FIG. 20B)

Tumor Growth Inhibition:

Control group: A2058 tumor bearing mice with human PBMC treated with vehicle or isotype control antibodies developed tumors which grew as expected.

Monotherapy:

Ipilimumab treatment at 3 mg/kg combined with IgG4 (Group#3) resulted in significant tumor growth inhibition (p<0.04) as compared to vehicle control Group#1. However, when compared to isotype control Group#2, the statistical significance was lost (p<0.23).

Pembrolizumab treatment alone at 2.5 or 5 mg/kg (Group#13, 14) showed observable tumor growth inhibition without statistical significance when compared to vehicle or isotype control group#12. Pembrolizumab combined with IgG1 (Group#4), showed observable tumor growth inhibition without statistical significance, however a significant increase in survival was observed (p<0.04) as compared to vehicle control Group#1. Statistical significance was lost (p<0.4) when compared with isotype control Group#2.

H2L5 hIgG4PE treatment alone at 0.4 mg/kg (Group#15) showed observable tumor growth inhibition without statistical significance as compared to vehicle or isotype control group#12. H2L5 hIgG4PE at 0.04 or 0.4 mg/kg combined with IgG1 (Group#5 and 6) showed observable delay in tumor progression and mice survival but didn't reach statistical significance.

Combination Treatment:

Combination of H2L5 hIgG4PE (0.04 or 0.4 mg/kg) with ipilimumab (3 mg/kg). Groups #8 and #9 showed no additional tumor growth inhibition as compared to Ipilimumab alone (Group#3). Combination of H2L5 hIgG4PE (0.04 or 0.4 mg/kg) with pembrolizumab (5 mg/kg) Groups #10 and #11 demonstrated modest but insignificant tumor growth inhibition and mice survival compared to pembrolizumab monotherapy, Group#4, or H2L5 hIgG4PE monotherapy Groups #5 and #6.

Clinical Observations:

Mice body weight loss observed during the study was approximately 20%. Tumor ulceration was apparent in multiple tumors during the study across the majority of group.

Mouse Fates:

A total of 100 out of 160 mice were euthanized when tumor volumes reached >2000 mm$^3$. 29 mice were euthanized due to tumor ulceration, 18 mice were found dead, 12 mice were euthanized due to body weight loss >20%, and one mouse was euthanized as moribund. Mice were found dead across the groups including the isotype control group #2. These deaths were attributed to the susceptibility of the model for a Graft-versus-Host Disease state, and not treatment related since no pattern was observed with treatment groups compared to the isotype control group.

Efficacy study evaluating H2L5 hIgG4PE dosed in combination with ipilimumab or pembrolizumab (FIG. 20C)
Tumor Growth Delay:
Control group: A2058 tumor bearing mice with human PBMC treated with vehicle or isotype control antibodies developed tumors which grew as expected.
Monotherapy:
Ipilimumab treatment at 3 mg/kg combined with IgG4 (Group#3) demonstrated significant tumor growth inhibition (p<0.02) and significant increase in survival (p<0.01) as compared to vehicle control Group#1. Compared to isotype control Group#2 however, the tumor growth inhibition did not reach significance (p<0.13) while significant increase in mice survival remained (p<0.04).
Pembrolizumab treatment at 5 mg/kg combined with IgG1 (Group#4) showed tumor growth inhibition without statistical significance as compared to vehicle or isotype control Group#2.
H2L5 hIgG4PE treatment alone at 0.01 mg/kg or 0.04 mg/kg (Group#12 and #13) demonstrated significant tumor growth inhibition (p<0.03) compared to vehicle control group #1 H2L5 hIgG4PE dosed at 0.04 mg/kg also showed a significant increase in mice survival (p<0.048) as compared to vehicle control group#1. However, as compared to isotype control group#2, tumor growth inhibition and survival did not reach statistical significance for groups #12 and #13. H2L5 hIgG4PE at 0.01 mg/kg combined with IgG1 (Group#5) showed significant tumor growth inhibition (p<0.03) and mice survival (p<0.03) as compared to vehicle control group#1. However, as compared to isotype control group#2, tumor growth delay and survival did not reach statistical significance. H2L5 hIgG4PE at 0.04 mg/kg combined with IgG1 (Group#6) showed observable tumor growth inhibition and mice survival, but did not reach statistical significance.
Combination Treatment:
The combination of H2L5 hIgG4PE with ipilimumab (0.01 mg/kg plus ipilimumab 3 mg/kg; Group#8) showed observable tumor growth inhibition and mice survival but failed to reach statistical significance. H2L5 hIgG4PE combination with ipilimumab (0.04 mg/kg plus ipilimumab 3 mg/kg; Group#9) demonstrated significant tumor growth inhibition (p<0.00) and a significant increase in mice survival (p<0.04) as compared to vehicle control group#1 or isotype control group#2 (p<0.02). However, as compared to isotype control survival failed to reach statistical significance. Combination activity did not reach significance as compared to monotherapy ipilimumab group#3 or H2L5 hIgG4PE monotherapy groups.

H2L5 hIgG4PE (0.01 mg/kg or 0.04 mg/kg) combination with pembrolizumab (5 mg/kg), Groups#10 and #11, showed significant tumor growth inhibition. (p≤0.03) and significant increase of mice survival observed (p<0.03) when comparing to vehicle control group#1. When comparing to isotype control group#2, the tumor growth inhibition significance remained in the 0.04 mg/kg H2L5 hIgG4PE combination with pembrolizumab (p<0.03). The survival benefit failed to reach statistical significance however. The combination failed to reach significance as compared to either monotherapy treatment group pembrolizumab group#3 or H2L5 hIgG4PE group#5 or #6. Thus, H2L5 hIgG4PE combined with pembrolizumab (0.01 or 0.04 mg/kg plus pembrolizumab 5 mg/kg) demonstrated an increase in tumor growth inhibition and mice survival but failed to reach statistical significance versus isotype control or monotherapies.

Clinical Observations:
Mice body weight loss observed during the study was approximately 20%. Tumor ulceration was observed across the majority of groups during the study.
Mouse Fates:
A total of 91 mice were euthanized due to tumor size >2000 mm$^3$, 34 mice were euthanized due to tumor ulcerations, and 5 mice were found dead. These deaths were attributed to the susceptibility of the model for a Graft-versus-Host Disease state.
Discussion Efficacy of H2L5 hIgG4PE as a monotherapy and in combination with pembrolizumab as well as ipilimumab was evaluated in the human PBMC engrafted NSG mouse model with A2058 melanoma tumors. This model where human PBMC are intravenously injected into adult immunodeficient NSG (NOD/SCID/IL-2Rγnull) mice is known as the Hu-PBMC NSG model. It induces a Graft-versus-Host Disease (GvHD) and has been used to study effector and memory T cell activity. The Hu-PBMC NSG model was implanted with human cancer cell line A2058 subcutaneously to investigate the effect of human immunotherapeutic antibodies on tumor growth. The limitations of this model include onset of GvHD symptoms, loss of body weight, and frequent tumor ulcerations which prevent survival monitoring for longer period of time as is possible with syngeneic mouse tumor models.

Initial studies evaluating H2L5 hIgG4PE at doses ranging from 0.04 mg/kg to 4 mg/kg showed that doses in the lower range demonstrated modest tumor growth inhibition. Delay in tumor progression and increased survival of mice was observed in dose groups ranging from 0.04 to 0.4 mg/kg though not statistically significant when compared to the isotype control groups. Based on these studies, H2L5 hIgG4PE doses of 0.04 to 0.4 mg/kg were selected for further evaluation alone and in combination with pembrolizumab and ipilimumab in two studies with PBMC grafts from two different donors (donor numbers 4568 and 6711). Modest responses for H2L5 hIgG4PE monotherapy and combination with pembrolizumab were observed in one of the two combination studies performed. The combination study using PBMC donor 4568 (Table 13, FIG. 20C) demonstrated anti-tumor activity of the monotherapy and combination while the study using PBMC donor 6711 (Table 12, FIG. 20B) did not show significant anti-tumor effect, which likely was a result of donor PBMC differences between studies, which reflect the patient response variability that may be observed in the clinic. In this second combination study with PBMC donor 4568, enhanced tumor growth inhibition and increased survivability of mice was observed in the combination group when compared to either agent alone, although this difference was not statistically significant. Combination synergy was observed however, since the H2L5 hIgG4PE 0.04 mg/kg dose in combination with pembrolizumab 5 mg/kg resulted in a statistically significant decrease in tumor volume ten days post first dose and increased survivability versus the isotype control group (p≤0.05), while the monotherapies did not. In fact, 50% of the mice in the H2L5 hIgG4PE and pembrolizumab combination group remained on study by day 33, but were removed due to tumor ulcerations. Only four mice were removed from study due to tumor volume from this combination group, while 8 to 9 mice were removed from study in the pembrolizumab and isotype groups.

Anti-PD1 therapy did not demonstrate statistically significant activity in this model as seen with the limited change in tumor growth and survival seen with pembrolizumab treated cohort compared to isotope treated cohort. Ipilimumab monotherapy showed a trend of tumor growth inhibition modestly better than pembrolizumab in both studies, and it showed statistically significant increase in survival versus isotype in the second combination study with the responsive PBMC donor 4568 (p≤0.04). The H2L5 hIgG4PE 0.01 mg/kg dose in combination with ipilimumab 3 mg/kg showed a significant increase in survival versus ipilimumab (p≤0.02), but not versus H2L5 hIgG4PE monotherapy. There were no additional significant effects on tumor volume observed with the combination of H2L5 hIgG4PE and ipilimumab in this model compared to either agent alone. Mice from across all treatment groups including vehicle and isotype control groups were found dead as reported in the Fate Tables. These deaths were attributed to the susceptibility of the model for a Graft-versus-Host Disease state, and not treatment related.

Example 12: Functional Activity of Anti-Murine ICOS Agonist Antibody Alone and in Combination with Anti-PD1 and Anti-CTLA-4 Antibodies In Vivo CT26 and EMT6 Syngeneic Mouse Tumor Models
CT26 murine colon carcinoma mouse tumor model
Methods
This study was conducted under a protocol which was approved by the GSK Institutional Animal Care and Use Committee prior to commencement of the study.
Animals
In this study 164 female BALB/c mice from Harlan Sprague Dawley. Mice were 6-8 weeks old at the beginning of the study when they were inoculated.
Cell Culture and Inoculation
One vial of CT-26 cells (ATCC: CRL-2638) ($3 \times 10^6$ cells; P-11) was thawed from $-140°$ C. and plated in RPMI with 10% FBS. Cells were subcultured 3 times over 10 days. Trypsin/EDTA was used to facilitate cell detachment from culture flask during subculturing. Cells were collected, washed twice, and re-suspended in RPMI without FBS at $5 \times 10^5$ cells/ml. Mice were inoculated subcutaneously with 0.1 ml cells ($5 \times 10^4$ cells/mouse) on the right hind flank.
On the day of cell collection and inoculation, cell counts were done on Beckman Coulter Vi-cell XR and checked by hemacytometer. Cells were detached from flask with trypsin/EDTA and washed twice, first with RPMI+10% FBS and second with RPMI only and resuspended in 10 ml RPMI. $178 \times 10^6$ cells were collected in 20 ml RPMI with 98.8% viability. 1.685 ml cell suspension ($15 \times 10^6$ cells total) was added to 28.315 ml RPMI.
$15 \times 10^6$ cells/30 ml media=$5 \times 10^5$ cells/ml. This equates to $5 \times 10^4$ cells/100 µl.
Antibody Formulation and Preparation
Antibodies were diluted from stock source vials to desired concentrations in sterile 0.9% saline on the day of dosing. Anti-ICOS agonist clone C398.4 was tested at 0.05 mg/kg and 0.5 mg/kg. Each dose was also tested with both anti-PD1 10 mg/kg and anti-CTLA-4 1 mg/kg.
Experimental Protocol(s)
Tumor Monitoring and Dosing
Mice were inoculated on day 0. On day 11 body weight and tumor volume were measured. Mice were randomized into the 12 study groups shown in Table 14 with 10 mice/group based on tumor size. Randomization was done using Studylog Study Director software. Mice were dosed based on the study design chart twice weekly starting on randomization day and continuing for 6 total doses. Dosing was interperitoneal (IP) in 100 µl volume of 0.9% saline vehicle. Tumor volume and body weight were measured 3 times per week throughout the study.
Endpoints
Mice were removed from the study for tumor burden when tumor volume was greater than 2000 mm³. Tumor volume was calculated by applying length and width caliper measurements to the following formula: TV=$0.52 * L * W^2$.
Additionally mice were removed from study when tumors developed open ulcerations. Ulcerations were observed throughout the experiment, however scabbed over ulcerations alone were not an endpoint unless they formed open holes.
Although it did not apply to any mice in this study a third endpoint established at the beginning of the study was a decrease of 20% body weight.

| Drugs and Materials | | | | |
|---|---|---|---|---|
| Antibody | Vendor | Catalog # | Lot | Clone |
| ICOS | Biolegend | 93108 | B205973 | C398.4 |
| PD1 | BioXcell | BE0146 | 5792-10/0815B | RMP1-14 |
| CTLA-4 | BioXcell | BE0164 | 5632-4/0715 | 9D9 |
| Mouse IgG2b | BioXcell | BE0086 | 4700/1014 | MCP-11 |
| Rat IgG2a | BioXcell | BE0089 | 5679-6/0815 | 2A3 |
| Hamster IgG | Biolegend | 92257 | B205974 | HTK888 |

All antibodies were diluted to desired concentrations in 0.9% saline and saline was used as a vehicle control.
Data Analysis
The event for survival analysis is tumor volume of 2000 mm³ or tumor ulceration, whichever came first. The exact time to cut-off volume was estimated by fitting a linear line between log tumor volume and day of two observations, the first observation that exceed the cut-off volume and the one observation that immediately preceded the cut-off volume. The Kaplan-Meier (KM) method was carried out to estimate the survival probability of different treatment groups at a given time. The median time to endpoint and its corresponding 95% confidence interval was reported. Whether or not KM survival curves are statistically different between any two groups was then tested by the log-rank test.
Tumor volumes at 17 days after initial dosing between the different treatment groups were compared. Prior to the analysis, the tumor volume was natural log transformed due to the inequality of variance in the different treatment groups. ANOVA followed by pair-wise comparison were then carried out on the log transformed data.

TABLE 14

| Study Groups | |
|---|---|
| Group No. | Treatment |
| 1 | Saline |
| 2 | Mouse IgG2b 20 µg + Hamster IgG 10 µg |
| 3 | Rat IgG2a 200 µg + Hamster IgG 10 µg |
| 4 | Hamster IgG 10 µg |
| 5 | ICOS 1 µg |
| 6 | ICOS 10 µg |
| 7 | CTLA-4 20 µg |
| 8 | PD1 200 µg |
| 9 | ICOS 1 µg + CTLA-4 20 µg |
| 10 | ICOS 10 µg + CTLA-4 20 µg |
| 11 | ICOS 1 µg + PD1 200 µg |
| 12 | ICOS 10 µg + PD1 200 µg |

The raw p-value, as well as the false discovery rate (FDR) adjusted p-values, from the comparisons of days to events by survival analysis and the comparisons of log transformed tumor volume at day 10 between treatment groups are shown in the above table. Comparisons, using FDR adjusted p-values ≤0.05, are declared to be statistically significant.

Results

Mouse fate tracking showed that the number of mice removed from study for tumor burden and tumor ulceration. All remaining mice are tumor free at study day 61 except 1 mouse in G7 which has a tumor volume of 579.16 mm$^3$.

For survival (time to endpoints) groups 9 and 12 showed significant increase in survival compared to the vehicle control group (p=0.008 and p=0.001 respectively). Group 12 showed statistically significant extended survival compared to groups 2, 4, and 5 (p=0.006, 0.001, 0.02). However, no combination group showed statistically significant (p<0.05) increased survival over either monotherapy. (FIG. 21)

Discussion

The combination therapy groups, particularly the high dose anti-ICOS and anti-PD1 combination (Group 12), demonstrated tumor growth inhibition and increased survival over monotherapy and isotype control groups, although statistical significance was not reached at Day 61. The isotype control for group 12 was the Rat IgG2a+ Hamster IgG group 3. The monotherapy groups for comparison are; ICOS 10 μg (group 6) and PD1 200 μg (group 8). A total of 5 mice remained as tumor free in group 12 compared to 1 in group 3, 1 in group 6 and 1 in group 8. The survival benefit was quantified by taking the day each mouse reached any of the pre-determined study endpoints. A number of mice were removed from study for open tumor ulcerations and not due to tumor burden.

In the high dose ICOS+CTLA-4 combination group (group 10) an increased number of mice were removed due to tumor ulceration by day 31 which likely masked the survival and anti-tumor benefit that this combination provided. In this group, 5 mice were removed for tumor ulcerations and only 2 for tumor burden reaching 2000 mm$^3$. All tumors removed due to tumor ulceration where still at modest size when taken off study, and it is expected that tumor ulceration may have been the result of a therapy-induced anti-tumor immune response in these mice. Three mice remained tumor free in this group out to day 61. The 2 mice removed for tumor burden were the lowest number of mice removed for tumor burden of all groups.

EMT6 Mammary Carcinoma Mouse Tumor Model

Experimental Protocol(s)

All procedures and euthanization criteria described in this document are in accordance with IACUC protocol AUP0606. Animals are weighed and inoculated on the right hind quarter with 100 μl of 1×10$^5$ EMT6 tumor cells per mouse. The number of mice inoculated is equal to at least 130% of what was needed for the study. Assuming 30% failure rate (either too big or too small at time of start of study), the goal was to have n=10 for each group. After tumor cell inoculation, tumor growth and total body weight were measured 3 times a week with a Fowler "ProMax" digital caliper for 4 weeks or longer. Antibodies were acquired from a commercial vendor and diluted to desired concentration in 0.9% saline. Dosing (i.p.) occurred biweekly, for a total of 6 doses and initiated on the day of randomization, designated as Day 0, when average tumor volume approximated 100 mm$^3$, approximately 7 to 8 days after inoculation. Randomization was performed using the Studylog Study Director Suite software. Length and width of tumors was measured in order to determine tumor volume using the formula (tumor volume=L*W$^2$*0.52). Tumor measurement of greater than 2,000 mm$^3$ for an individual animal resulted in removal from study. Mice may also be removed from the study due to weight loss (>20%), tumor ulceration, or any other obvious inhibition of normal mouse activity due to morbidity.

In this study, a total of 191 animals were inoculated with EMT6 cells in order to generate enough mice with tumors in the desired size range for 13 groups of 10 mice each as shown in Table 15. Saline vehicle injected mice and isotype control groups served as controls for ICOS, PD1 and CTLA-4 mAb treated mice. The isotype control for ICOS (Hamster IgG) was dosed at 10 μg alone and in combination with the isotype for CTLA-4 (mouse IgG2b) or PD-1 (rat IgG2a). Monotherapy treatment groups for anti-CTLA-4 (9D9) and anti-PD-1 (RMP1-14) were dosed at 20 and 200 μg per mouse, respectively, and evaluated in combination with the ICOS isotype control. The C398.4 clone of ICOS agonist was dosed at 10 and 1 μg per mouse. Efficacy of the ICOS agonist was also evaluated at 10 and 1 μg per mouse dosed in combination with anti-CTLA-4 or anti-PD-1. An additional group of PD-1 and CTLA-4 at predescribed concentrations was included as a positive control comparator group. Statistical analysis of tumor volume was performed on day 13 post randomization. Survivability analysis included mice on study through day 60.

TABLE 15

Study Groups

| Dosing | treatment 1 | treatment 2 | n = |
|---|---|---|---|
| Group 1: 1 × 10$^5$ cells per | saline | | 10 |
| Group 2: 1 × 10$^5$ cells per | Hamster IgG 10 μg | mIgG2b 20 μg | 10 |
| Group 3: 1 × 10$^5$ cells per | Hamster IgG 10 μg | rIgG2a 200 μg | 10 |
| Group 4: 1 × 10$^5$ cells per | Hamster IgG 10 μg | | 10 |
| Group 5: 1 × 10$^5$ cells per | ICOS 10 μg | | 10 |
| Group 6: 1 × 10$^5$ cells per | ICOS 1 μg | | 10 |
| Group 7: 1 × 10$^5$ cells per | CTLA4 20 μg | Hamster IgG 10 μg | 10 |
| Group 8: 1 × 10$^5$ cells per | PD-1 200 μg | Hamster IgG 10 μg | 10 |
| Group 9: 1 × 10$^5$ cells per | ICOS 10 μg | CTLA4 20 μg | 10 |
| Group 10: 1 × 10$^5$ cells per | ICOS 1 μg | CTLA4 20 μg | 10 |
| Group 11: 1 × 10$^5$ cells per | ICOS 10 μg | PD-1 200 μg | 10 |
| Group 12: 1 × 10$^5$ cells per | ICOS 1 μg | PD-1 200 μg | 10 |
| Group 13: 1 × 10$^5$ cells per | CTLA4 20 μg | PD-1 200 μg | 10 |

Drugs and Materials

Animals

Female Balb/c mice from 6 to 8 weeks of age were received from Harlan Sprague Dawley and housed in accordance with IACUC standards.

EMT6 Cells

EMT6 cells were thawed and cultured in cell culture flasks for eight days prior to inoculation. Cells were passed 3 times in this time. On the day of inoculation, the cells are harvested from the flask in complete medium. Cells are centrifuged and resuspended in Weymouth's (with 15% FBS). This step is repeated 3 times in Weymouth's media without FBS. Cell density and viability are checked via trypan blue exclusion. Cells are then diluted to desired density (1×10$^6$ cells per mL).

Immunotherapeutics

All therapeutics were diluted to desired concentrations in 0.9% sodium chloride on the day of dosing and injected i.p. using a 30 G needle. Therapeutic and control dilutions are presented below in Table 16.

TABLE 16

Therapeutic dilutions

| Rx | starting conc. mg/mL | desired conc. mg/mL | dilution 1: | dose/ mouse mg | number of mice | volume needed mL | add stock mL | Total diluent mL | total volume mL |
|---|---|---|---|---|---|---|---|---|---|
| mouse IgG2b | 4.46 | 0.1 | 44.6 | 0.02 | 10 | 2 | 0.10 | 4.36 | 4.46 |
| rat IgG2a | 6.92 | 1 | 6.92 | 0.2 | 10 | 2 | 0.40 | 2.37 | 2.77 |
| Hamster IgG | 1.47 | 0.05 | 29.4 | 0.01 | 50 | 10 | 0.40 | 11.36 | 11.76 |
| CTLA 4 | 6.1 | 0.1 | 61 | 0.02 | 40 | 8 | 0.15 | 9 | 9.15 |
| PD-1 | 7.44 | 1 | 7.44 | 0.2 | 40 | 8 | 1.30 | 8.372 | 9.672 |
| ICOS | 5 | 0.05 | 100 | 0.01 | 30 | 6 | 0.10 | 9.9 | 10 |
| ICOS | 0.05 | 0.005 | 10 | 0.001 | 30 | 6 | 1.00 | 9 | 10 |

Data Analysis
Statistical Analysis

The event for survival analysis was tumor volume of 2000 mm$^3$ or tumor ulceration, whichever came first. The exact time to cut-off volume was estimated by fitting a linear line between log tumor volume and day of two observations, the first observation that exceed the cut-off volume and the one observation that immediately preceded the cut-off volume. The Kaplan-Meier (KM) method was carried out to estimate the survival probability of different treatment groups at a given time. The median time to endpoint and its corresponding 95% confidence interval was reported. Whether or not KM survival curves were statistically different between any two groups was then tested by the log-rank test.

Tumor volumes at 13 days after initial dosing between the different treatment groups were compared. Prior to the analysis, the tumor volume was natural log transformed due to the inequality of variance in the different treatment groups. ANOVA followed by pair-wise comparison were then carried out on the log transformed data. SAS 9.3 and R 3.0.2 Analysis Software was utilized.

Results

Balb/c mice were inoculated and randomized into groups of ten based on treatment regimen 8 days later. Administration of therapeutics or controls began on randomization day (Day 0) and continued twice a week for 3 weeks.

The saline treated group grew tumors at the expected rate relative to previous EMT-6 studies. All mice in the saline vehicle group were euthanized due to tumor size or ulceration by day 30. Treatment with hamster IgG alone or in combination with rat IgG2a or mouse IgG2b, resulted in no statistically significant change in average tumor growth or survival when compared to the saline vehicle group.

Figure 22B:
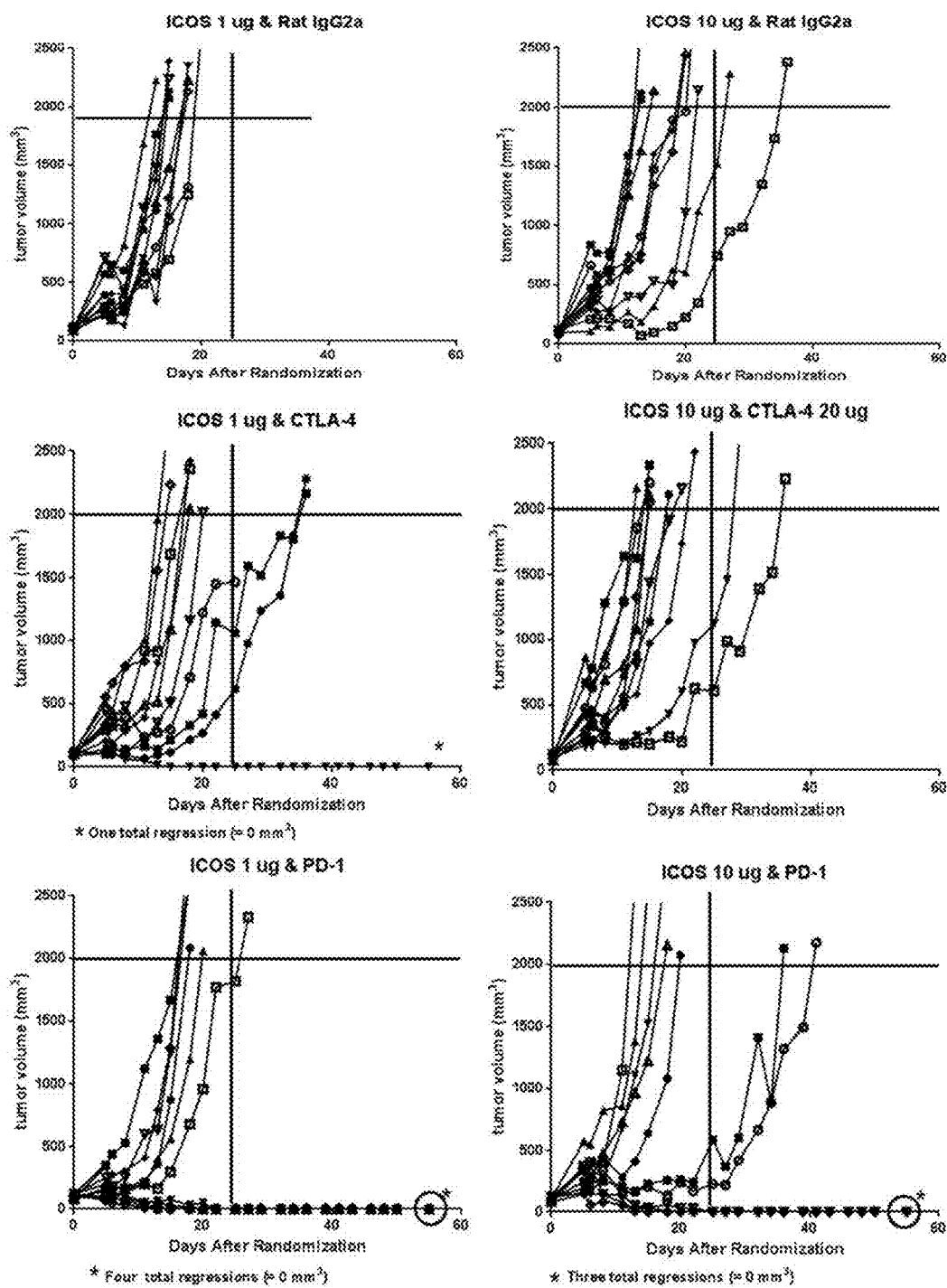
Figure 22C:
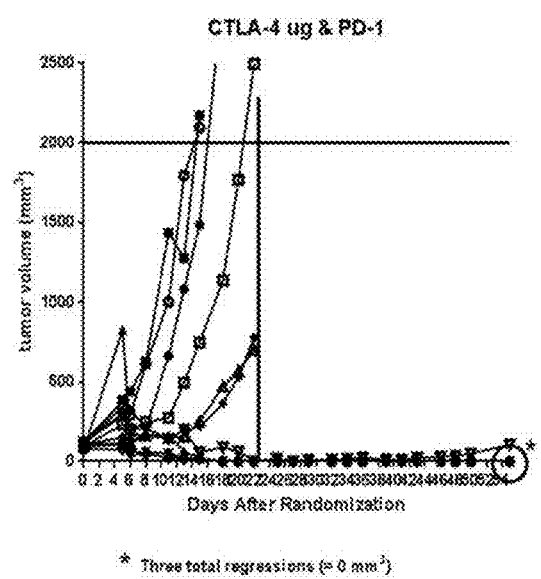

At 13 days post randomization, the ICOS monotherapy groups demonstrated little observable change in average tumor growth as compared to isotype controls. However, the high dose ICOS treatment group (10 μg) demonstrated an apparent trend towards more tumor growth inhibition than the low dose group. An effect that was comparable to the CTLA-4 monotherapy activity was observed. Monotherapy treatment with PD-1 mAb also resulted in some observable, but statistically insignificant reduction in average tumor volume at day 13. However, as with ICOS and CTLA-4 monotherapy, this did not result in increased survival when compared to that of the appropriate isotype groups. Treatment with the combination of anti-PD-1 and anti-ICOS antibody clone C398.4 at the 10 μg dose resulted in considerable tumor growth inhibition as compared to control and monotherapy treatment groups (FIG. 22). Three mice in this combination group achieved complete tumor regression, a considerable improvement over control or monotherapy treatment groups. However, due to the statistical criteria used, statistically significant improvement in survival was not reached. The combination of anti-PD-1 with 1 μg of ICOS agonist antibody clone C398.4 did result in a statistically significant decrease in average tumor growth at day 13 as compared to saline vehicle control (p<0.05) and ICOS monotherapy (p<0.05) groups of 1 and 10 μg. Four mice from this treatment regimen achieved complete tumor regression resulting in significant trend towards increased survival that failed to reach statistical significance.

The ICOS antibody at both doses in combination with anti-CTLA-4 demonstrated little observable benefit in tumor growth inhibition or survival as compared to monotherapy treatment with either antibody.

Discussion

While isotype controls resulted in no obvious change in average tumor volume or overall survival when compared to the saline vehicle group, there were individual animals in the hamster IgG group (group 4) and the hamster IgG and rat IgG2a (group 3) that demonstrated delayed tumor growth. In the hamster IgG & rat IgG2a isotype group, one mouse survived beyond the last saline vehicle mouse, being sacrificed on day 36 due to ulceration with a tumor that measured 1156.56 mm$^3$ in volume. Two mice in the hamster IgG group survived longer than the saline group. One animal was euthanized due to tumor size on day 36, and the second one on day 41 due to ulceration with a measurement of 1899.28 mm$^3$.

The dosing regimen of anti-PD-1 with 10 μg of anti-ICOS agonist led to an observable inhibition of tumor growth resulting in a decrease in tumor volume at day 13 when compared to isotype controls, although this difference was less obvious when compared to anti-PD-1 monotherapy. However, the combination did result in a total of five animals surviving beyond any in the anti-PD-1 monotherapy group, with three mice experiencing complete tumor regression as compared to none in the anti-PD-1 monotherapy group.

Pairing anti-PD-1 with a 1 μg dose of ICOS agonist antibody led to an observable decrease in average tumor size at day 13 when compared to isotype controls and respective monotherapy groups. This decrease was statistically significant when compared to saline vehicle control (p<0.05) and the 1 μg ICOS monotherapy group (p<0.05). Four mice experienced complete tumor regression and survived beyond any in the PD-1 monotherapy group The survival benefit observed with the ICOS+PD1 combination group was not found to reach statistical significance relative to controls by day 60. However, the tumor growth inhibition and survival benefit of the ICOS+PD1 combination treatment groups was comparable to the activity observed with the PD1+CTLA-4 combination group, which was considered a positive control for anti-tumor activity in this study. This suggests that a combination of ICOS and PD1 antibodies may have benefit similar to CTLA-4 and PD1 combinations, which have demonstrated significant clinical activity in some tumor types.

Of the 130 mice enrolled in this study, 12 remained alive at day 60 with 11 having achieved complete tumor regression. Of the 118 mice that met endpoints for study removal, 111 were removed due to reaching a tumor size of 2000 mm$^3$. The remaining seven mice were euthanized due to ulceration on the tumor. Occurrences of ulceration were spread out among the groups. Groups 1 (Saline), 3 (hamster IgG & rat IgG2a), 4 (hamster IgG), 6 (1 µg ICOS), and 10 (CTLA-4 with 1 µg ICOS) all had one animal removed due to ulceration. Group 13 (CTLA-4+PD-1) showed two animals sacrificed due to ulceration. The remaining groups had no animals removed due to ulceration.

The invention claimed is:

1. A method of treating a cancer in a human in need thereof, which method comprises administering an ICOS binding protein or antigen binding portion thereof to said human, wherein the ICOS binding protein or antigen binding portion thereof cross-competes for binding to human ICOS with a reference antibody or antigen binding portion thereof comprising a $V_H$ domain comprising an amino acid sequence set forth in SEQ ID NO:7; and a $V_L$ domain comprising the amino acid sequence set forth in SEQ ID NO:8, and administering an anti-PD-1 antibody to said human.

2. The method of claim 1 wherein the ICOS binding protein or antigen binding portion thereof binds to human ICOS with
   (i) an association rate constant ($k_{on}$) of at least $1 \times 10^5$ $M^{-1}s^{-1}$; and a dissociation rate constant ($k_{off}$) of less than $6 \times 10^{-5}$ $s^{-1}$; or
   (ii) a dissociation constant ($K_D$) of less than about 100 nM,
wherein the affinity is measured by BIAcore.

3. The method of claim 1 wherein the anti-PD-1 antibody is nivolumab.

4. The method of claim 1 wherein the anti-PD-1 antibody is pembrolizumab.

5. The method of claim 1 wherein the ICOS binding protein is a monoclonal antibody.

6. The method of claim 5 wherein the monoclonal antibody is humanized or fully human.

7. The method of claim 1 wherein said cancer is colorectal cancer (CRC).

8. The method of claim 1 wherein said cancer is esophageal cancer.

9. The method of claim 1 wherein said cancer is cervical cancer.

10. The method of claim 1 wherein said cancer is bladder cancer.

11. The method of claim 1 wherein said cancer is breast cancer.

12. The method of claim 1 wherein said cancer is head and neck cancer.

13. The method of claim 1 wherein said cancer is ovarian cancer.

14. The method of claim 1 wherein said cancer is melanoma.

15. The method of claim 1 wherein said cancer is renal cell carcinoma (RCC).

16. The method of claim 1 wherein said cancer is EC squamous cell.

17. The method of claim 1 wherein said cancer is non-small cell lung carcinoma.

18. The method of claim 1 wherein said cancer is mesothelioma.

19. The method of claim 1 wherein said cancer is prostate cancer.

20. The method of claim 1 wherein said cancer is gastric cancer.

* * * * *

SEQUENCE LISTING

```
<160> NUMBER OF SEQ ID NOS: 24

<210> SEQ ID NO 1
<211> LENGTH: 5
<212> TYPE: PRT
<213> ORGANISM: Murine

<400> SEQUENCE: 1

Asp Tyr Ala Met His
1               5

<210> SEQ ID NO 2
<211> LENGTH: 17
<212> TYPE: PRT
<213> ORGANISM: Murine

<400> SEQUENCE: 2

Leu Ile Ser Ile Tyr Ser Asp His Thr Asn Tyr Asn Gln Lys Phe Gln
1               5                   10                  15

Gly

<210> SEQ ID NO 3
<211> LENGTH: 12
<212> TYPE: PRT
<213> ORGANISM: Murine

<400> SEQUENCE: 3

Asn Asn Tyr Gly Asn Tyr Gly Trp Tyr Phe Asp Val
1               5                   10

<210> SEQ ID NO 4
<211> LENGTH: 10
<212> TYPE: PRT
<213> ORGANISM: Murine

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Murine

<400> SEQUENCE: 5

Asp Thr Ser Lys Leu Ala Ser
1               5

<210> SEQ ID NO 6
<211> LENGTH: 9
```

<212> TYPE: PRT
<213> ORGANISM: Murine

<400> SEQUENCE: 6

Phe Gln Gly Ser Gly Tyr Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Artificially Synthesized Sequence

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Ala Met His Trp Val Arg Gln Ala Pro Gly Gln Gly Leu Glu Trp Met
            35                  40                  45

Gly Leu Ile Ser Ile Tyr Ser Asp His Thr Asn Tyr Asn Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Asn Asn Tyr Gly Asn Tyr Gly Trp Tyr Phe Asp Val Trp Gly
            100                 105                 110

Gln Gly Thr Thr Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Artificially Synthesized Sequence

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
                20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Phe Gln Gly Ser Gly Tyr Pro Tyr Thr
                85                  90                  95

Phe Gly Gln Gly Thr Lys Leu Glu Ile Lys
            100                 105

<210> SEQ ID NO 9
<211> LENGTH: 467
<212> TYPE: PRT
<213> ORGANISM: Artificial Sequence
<220> FEATURE:

<223> OTHER INFORMATION: Artificially Synthesized Sequence

<400> SEQUENCE: 9

```
Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
             20                  25                  30

Pro Gly Ser Ser Val Lys Val Ser Cys Lys Ala Ser Gly Tyr Thr Phe
         35                  40                  45

Thr Asp Tyr Ala Met His Trp Val Arg Gln Ala Pro Gly Gln Gly Leu
     50                  55                  60

Glu Trp Met Gly Leu Ile Ser Ile Tyr Ser Asp His Thr Asn Tyr Asn
 65                  70                  75                  80

Gln Lys Phe Gln Gly Arg Val Thr Ile Thr Ala Asp Lys Ser Thr Ser
             85                  90                  95

Thr Ala Tyr Met Glu Leu Ser Ser Leu Arg Ser Glu Asp Thr Ala Val
            100                 105                 110

Tyr Tyr Cys Gly Arg Asn Asn Tyr Gly Asn Tyr Gly Trp Tyr Phe Asp
        115                 120                 125

Val Trp Gly Gln Gly Thr Thr Val Thr Val Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Glu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465
```

```
<210> SEQ ID NO 10
<211> LENGTH: 168
<212> TYPE: PRT
<213> ORGANISM: Homo Sapien

<400> SEQUENCE: 10

Met Lys Ser Gly Leu Trp Tyr Phe Phe Leu Phe Cys Leu Arg Ile Lys
  1               5                  10                  15

Val Leu Thr Gly Glu Ile Asn Gly Ser Ala Asn Tyr Glu Met Phe Ile
             20                  25                  30

Phe His Asn Gly Gly Val Gln Ile Leu Cys Lys Tyr Pro Asp Ile Val
         35                  40                  45

Gln Gln Phe Lys Met Gln Leu Leu Lys Gly Gly Gln Ile Leu Cys Asp
     50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
                100                 105                 110

Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Val Cys Ile Leu Gly Cys Ile Leu
145                 150                 155                 160

Ile Cys Trp Leu Thr Lys Lys Met
                165
```

```
<210> SEQ ID NO 11
<211> LENGTH: 19
<212> TYPE: PRT
<213> ORGANISM: Homo Sapien

<400> SEQUENCE: 11

Met Gly Trp Ser Cys Ile Ile Leu Phe Leu Val Ala Thr Ala Thr Gly
  1               5                  10                  15

Val His Ser
```

```
<210> SEQ ID NO 12
<211> LENGTH: 232
<212> TYPE: PRT
<213> ORGANISM: Artificial Sequence
<220> FEATURE:
<223> OTHER INFORMATION: Artificially Synthesized Sequence

<400> SEQUENCE: 12
```

```
Met Gly Trp Ser Cys Ile Ile Leu Phe Leu Val Ala Thr Ala Thr Gly
 1               5                  10                  15

Val His Ser Glu Ile Val Leu Thr Gln Ser Pro Ala Thr Leu Ser Leu
             20                  25                  30

Ser Pro Gly Glu Arg Ala Thr Leu Ser Cys Ser Ala Ser Ser Ser Val
         35                  40                  45

Ser Tyr Met His Trp Tyr Gln Gln Lys Pro Gly Gln Ala Pro Arg Leu
     50                  55                  60

Leu Ile Tyr Asp Thr Ser Lys Leu Ala Ser Gly Ile Pro Ala Arg Phe
65                  70                  75                  80

Ser Gly Ser Gly Ser Gly Thr Asp Tyr Thr Leu Thr Ile Ser Ser Leu
                 85                  90                  95

Glu Pro Glu Asp Phe Ala Val Tyr Tyr Cys Phe Gln Gly Ser Gly Tyr
             100                 105                 110

Pro Tyr Thr Phe Gly Gln Gly Thr Lys Leu Glu Ile Lys Arg Thr Val
         115                 120                 125

Ala Ala Pro Ser Val Phe Ile Phe Pro Pro Ser Asp Glu Gln Leu Lys
     130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                 165                 170                 175

Ser Gln Glu Ser Val Thr Glu Gln Asp Ser Lys Asp Ser Thr Tyr Ser
             180                 185                 190

Leu Ser Ser Thr Leu Thr Leu Ser Lys Ala Asp Tyr Glu Lys His Lys
         195                 200                 205

Val Tyr Ala Cys Glu Val Thr His Gln Gly Leu Ser Ser Pro Val Thr
     210                 215                 220

Lys Ser Phe Asn Arg Gly Glu Cys
225                 230

<210> SEQ ID NO 13
<211> LENGTH: 124
<212> TYPE: PRT
<213> ORGANISM: Murine

<400> SEQUENCE: 13

Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Ser Phe Thr Ser Tyr
             20                  25                  30

Trp Ile Asn Trp Val Lys Gln Arg Pro Gly Gln Gly Leu Glu Trp Ile
         35                  40                  45

Gly Asn Ile Tyr Pro Ser Asp Ser Tyr Thr Asn Tyr Asn Gln Met Phe
     50                  55                  60

Lys Asp Lys Ala Thr Leu Thr Val Asp Lys Ser Ser Asn Thr Ala Tyr
65                  70                  75                  80

Met Gln Leu Thr Ser Pro Thr Ser Glu Asp Ser Ala Val Tyr Tyr Cys
                 85                  90                  95

Thr Arg Trp Asn Leu Ser Tyr Tyr Phe Asp Asn Asn Tyr Tyr Leu Asp
             100                 105                 110

Tyr Trp Gly Gln Gly Thr Thr Leu Thr Val Ser Ser
         115                 120

<210> SEQ ID NO 14
```

```
<211> LENGTH: 109
<212> TYPE: PRT
<213> ORGANISM: Murine

<400> SEQUENCE: 14

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

His Leu Val Phe Gly Gly Gly Thr Lys Leu Thr Val Leu
            100                 105

<210> SEQ ID NO 15
<211> LENGTH: 121
<212> TYPE: PRT
<213> ORGANISM: Artificial Sequence
<220> FEATURE:
<223> OTHER INFORMATION: Artificially Synthesized Sequence

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Leu Ile Ser Ile Tyr Ser Asp His Thr Asn Tyr Asn Gln Lys Phe
    50                  55                  60

Gln Gly Arg Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Asn Asn Tyr Gly Asn Tyr Gly Trp Tyr Phe Asp Val Trp Gly
            100                 105                 110

Gln Gly Thr Thr Val Thr Val Ser Ser
        115                 120

<210> SEQ ID NO 16
<211> LENGTH: 451
<212> TYPE: PRT
<213> ORGANISM: Artificial Sequence
<220> FEATURE:
<223> OTHER INFORMATION: Artificially Synthesized Sequence

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45
```

-continued

Gly Leu Ile Ser Ile Tyr Ser Asp His Thr Asn Tyr Asn Gln Lys Phe
    50                  55                  60

Gln Gly Arg Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Asn Asn Tyr Gly Asn Tyr Gly Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

```
<210> SEQ ID NO 17
<211> LENGTH: 106
<212> TYPE: PRT
<213> ORGANISM: Artificial Sequence
<220> FEATURE:
<223> OTHER INFORMATION: Artificially Synthesized Sequence

<400> SEQUENCE: 17

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Ser Tyr Met
             20                  25                  30

His Trp Tyr Gln Gln Lys Pro Gly Gln Ala Pro Arg Leu Leu Ile Tyr
         35                  40                  45

Asp Thr Ser Lys Leu Ala Ser Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Phe Gln Gly Ser Gly Tyr Pro Tyr Thr
                 85                  90                  95

Phe Gly Gln Gly Thr Lys Leu Glu Ile Lys
            100                 105

<210> SEQ ID NO 18
<211> LENGTH: 213
<212> TYPE: PRT
<213> ORGANISM: Artificial Sequence
<220> FEATURE:
<223> OTHER INFORMATION: Artificially Synthesized Sequence

<400> SEQUENCE: 18

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Ser Tyr Met
             20                  25                  30

His Trp Tyr Gln Gln Lys Pro Gly Gln Ala Pro Arg Leu Leu Ile Tyr
         35                  40                  45

Asp Thr Ser Lys Leu Ala Ser Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Phe Gln Gly Ser Gly Tyr Pro Tyr Thr
                 85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 19
<211> LENGTH: 121
<212> TYPE: PRT
<213> ORGANISM: Murine

<400> SEQUENCE: 19

Gln Val Gln Leu Gln Gln Ser Gly Pro Glu Leu Val Arg Pro Gly Glu
1               5                   10                  15

Ser Val Lys Ile Ser Cys Met Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Ile Tyr Ser Asp His Thr Asn Tyr Asn Gln Lys Phe
    50                  55                  60

Gln Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Gly Arg Asn Asn Tyr Gly Asn Tyr Gly Trp Tyr Phe Asp Val Trp Gly
            100                 105                 110

Ala Gly Thr Thr Val Thr Val Ser Ser
        115                 120

<210> SEQ ID NO 20
<211> LENGTH: 107
<212> TYPE: PRT
<213> ORGANISM: Murine

<400> SEQUENCE: 20

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ile Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Tyr Thr
                85                  90                  95

Phe Gly Gly Gly Thr Lys Leu Glu Ile Lys Arg
            100                 105

<210> SEQ ID NO 21
<211> LENGTH: 1401
<212> TYPE: DNA
<213> ORGANISM: Artificial Sequence
<220> FEATURE:
<223> OTHER INFORMATION: Artificially Synthesized Sequence

<400> SEQUENCE: 21
atgggctggt cctgcatcat cctgtttctg gtggccaccg ccaccggcgt gcacagccag     60
gtgcagctgg tgcagagcgg agccgaggtg aaaaagcccg gctcaagcgt gaaggtgagc    120

| | |
|---|---|
| tgcaaggcca gcggctacac cttcaccgac tacgctatgc actgggtgag gcaggccccc | 180 |
| ggccagggcc tggagtggat gggcctgatc agcatctaca gcgaccacac caactacaac | 240 |
| cagaagttcc agggcagggt gaccatcacc gccgataaga gcaccagcac agcctacatg | 300 |
| gagctgagca gcctgaggag cgaagacacc gccgtgtact attgcggcag gaacaactac | 360 |
| ggcaactacg gctggtactt cgacgtgtgg ggccagggaa ccactgtcac cgtgagcagc | 420 |
| gccagcacca agggccccag cgtgttcccc ctggccccct gcagcagaag caccagcgag | 480 |
| agcacagccg ccctgggctg cctggtgaag gactacttcc ccgagcccgt gaccgtgagc | 540 |
| tggaacagcg gagccctgac cagcggcgtg cacaccttcc ccgccgtgct gcagagcagc | 600 |
| ggcctgtaca gcctgagcag cgtggtgacc gtgcccagca gcagcctggg caccaagacc | 660 |
| tacacctgca acgtggacca caagcccagc aacaccaagg tggacaagcg ggtggagagc | 720 |
| aagtacggcc ctccctgccc ccctgccct gccccgagt tcgagggcgg accctccgtg | 780 |
| ttcctgttcc ccccaagcc caaggacacc ctgatgatca gccggacccc cgaggtgacc | 840 |
| tgcgtggtgg tggacgtgag ccaggaagat cccgaggtcc agttcaattg gtacgtggac | 900 |
| ggcgtggagg tgcacaacgc caagaccaag ccccgggagg aacagttcaa cagcacctac | 960 |
| cgggtggtgt ccgtgctgac cgtgctgcac caggactggc tgaacggcaa agaatacaag | 1020 |
| tgcaaggtgt ccaacaaggg cctgcccagc tccatcgaga aaaccatcag caaggccaag | 1080 |
| ggccagcctc gggagcccca ggtgtacacc ctgcccccat cccaggaaga gatgaccaag | 1140 |
| aaccaggtgt ccctgacctg tctggtgaag ggcttctacc ccagcgacat cgccgtggag | 1200 |
| tgggagagca acggccagcc cgagaacaac tacaagacca cccccctgt gctggacagc | 1260 |
| gacggcagct tcttcctgta cagcaggctg accgtggaca agagccggtg gcaggaaggc | 1320 |
| aacgtctttta ctgcagcgt gatgcacgag gccctgcaca accactacac ccagaagagc | 1380 |
| ctgagcctgt ccctgggcaa g | 1401 |

<210> SEQ ID NO 22
<211> LENGTH: 696
<212> TYPE: DNA
<213> ORGANISM: Artificial Sequence
<220> FEATURE:
<223> OTHER INFORMATION: Artificially Synthesized Sequence

<400> SEQUENCE: 22

| | |
|---|---|
| atgggctggt cctgcatcat cctgtttctg gtggccaccg ccaccggcgt gcacagcgag | 60 |
| attgtgctga cccagagccc cgccaccctg agcctgagcc ccggcgaaag gcaaccctc | 120 |
| agctgcagcg ccagcagcag cgtgagctac atgcactggt accagcagaa gcccggccag | 180 |
| gccctaggc tgctgatcta cgacacctcc aagctggcca gcggcatccc agccaggttc | 240 |
| tcaggcagcg gcagcggcac cgactatact ctgaccatca gcagcctgga gcccgaggac | 300 |
| ttcgccgtgt actactgctt ccagggaagc ggctaccct acaccttcgg ccagggcacc | 360 |
| aagctggaga tcaagcgtac ggtggccgcc cccagcgtgt tcatcttccc cccagcgat | 420 |
| gagcagctga agagcggcac cgccagcgtg gtgtgtctgc tgaacaactt ctaccccgg | 480 |
| gaggccaagg tgcagtggaa ggtggacaat gccctgcaga gcggcaacag ccaggagagc | 540 |
| gtgaccgagc aggacagcaa ggactccacc tacagcctga gcagcaccct gaccctgagc | 600 |
| aaggccgact acgagaagca caaggtgtac gcctgtgagg tgacccacca gggcctgtcc | 660 |
| agccccgtga ccaagagctt caaccggggc gagtgc | 696 |

```
<210> SEQ ID NO 23
<211> LENGTH: 448
<212> TYPE: PRT
<213> ORGANISM: Artificial Sequence
<220> FEATURE:
<223> OTHER INFORMATION: Artificially Synthesized Sequence

<400> SEQUENCE: 23
```

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Leu Ile Ser Ile Tyr Ser Asp His Thr Asn Tyr Asn Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Asn Asn Tyr Gly Asn Tyr Gly Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

```
Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 24
<211> LENGTH: 213
<212> TYPE: PRT
<213> ORGANISM: Artificial Sequence
<220> FEATURE:
<223> OTHER INFORMATION: Artificially Synthesized Sequence

<400> SEQUENCE: 24

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Phe Gln Gly Ser Gly Tyr Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```